US009127044B2

(12) United States Patent
Krastel et al.

(10) Patent No.: US 9,127,044 B2
(45) Date of Patent: *Sep. 8, 2015

(54) CYCLIC DEPSIPEPTIDES

(75) Inventors: Philipp Krastel, Grenzach-Wyhlen (DE); Brigitta-Maria Liechty, Basel (CH); Josef Gottfried Meingassner, Vienna (AT); Esther Schmitt, Lörrach (DE); Erwin Paul Schreiner, Vienna (AT)

(73) Assignee: NOVARTIS AG, Basel (CH)

( * ) Notice: Subject to any disclaimer, the term of this patent is extended or adjusted under 35 U.S.C. 154(b) by 113 days.

This patent is subject to a terminal disclaimer.

(21) Appl. No.: 13/372,758

(22) Filed: Feb. 14, 2012

(65) Prior Publication Data

US 2012/0196790 A1 Aug. 2, 2012

Related U.S. Application Data

(63) Continuation of application No. 12/193,338, filed on Aug. 18, 2008, now Pat. No. 8,178,650.

(30) Foreign Application Priority Data

Aug. 17, 2007 (EP) ..................... 07114507

(51) Int. Cl.
*C07K 7/50* (2006.01)
*C07K 11/02* (2006.01)
*A61K 38/00* (2006.01)

(52) U.S. Cl.
CPC . *C07K 7/50* (2013.01); *C07K 11/02* (2013.01); *A61K 38/00* (2013.01)

(58) Field of Classification Search
CPC ........................................ C07K 7/50
USPC .......................... 530/317; 514/20.1
See application file for complete search history.

(56) References Cited

U.S. PATENT DOCUMENTS

| 4,424,370 | A | 1/1984 | Kleemann et al. |
| 5,595,756 | A | 1/1997 | Bally et al. |
| 6,630,569 | B1 | 10/2003 | Jeschke et al. |
| 8,178,650 | B2 | 5/2012 | Krastel et al. |
| 8,415,305 | B2 | 4/2013 | Krastel et al. |
| 8,614,289 | B2 | 12/2013 | Acemoglu et al. |
| 8,680,054 | B2 | 3/2014 | Haug |
| 2004/0110228 | A1 | 6/2004 | McAlpine et al. |
| 2005/0014684 | A1 | 1/2005 | Palomera et al. |
| 2009/0036487 | A1 | 2/2009 | Field et al. |
| 2009/0186042 | A1* | 7/2009 | Johnston et al. ......... 424/185.1 |
| 2011/0112121 | A1 | 5/2011 | Berghausen et al. |
| 2012/0064013 | A1 | 3/2012 | Marcos et al. |
| 2012/0064136 | A1 | 3/2012 | Baker, Jr. et al. |
| 2012/0122977 | A1 | 5/2012 | Coppola et al. |
| 2012/0277406 | A1 | 11/2012 | Acemoglu et al. |
| 2012/0328701 | A1 | 12/2012 | Edelson et al. |
| 2012/0328702 | A1 | 12/2012 | Edelson et al. |
| 2013/0017226 | A1 | 1/2013 | Park et al. |
| 2014/0100353 | A1 | 4/2014 | Acemoglu et al. |
| 2014/0100355 | A1 | 4/2014 | Acemoglu et al. |
| 2014/0162959 | A1 | 6/2014 | Haug |

FOREIGN PATENT DOCUMENTS

| EP | 0 052 200 A1 | 9/1981 |
| JP | 20000154198 A | 6/2000 |
| WO | 95/34558 A1 | 12/1995 |
| WO | 2004108139 A2 | 12/2004 |
| WO | 2005/075667 A1 | 8/2005 |
| WO | 2009024528 A1 | 2/2009 |
| WO | 2011003858 A2 | 1/2011 |
| WO | 2012035468 A2 | 3/2012 |
| WO | 2012103035 A1 | 8/2012 |
| WO | 2012103038 A2 | 8/2012 |

OTHER PUBLICATIONS

Abstract of Matsuda, H., Tennen Yuki Kagobutsu Toronkai Koen Yoshishu (1993), 35th, 654-661.*
Hiemstra, P.S., "Novel roles of protease inhibitors in infection and inflammation," Biochemical Society Transactions 30(2):116-120 (2002).
Kunze et al., "Chondramides A-D, New Antifungal and Cytostatic Depsipeptides from *Chondromyces crocatus* (Myxobacteria) Production, Physico-chemical and Biological Properties," The Journal of Antibiotics 48(11)1262-1266 (Nov. 1995).
Hachem et al.; "Serine Protease Activity and Residual LEKTI Expression Determine Phenotype in Netherton Syndrome"; Journal of Investigative Dermatology; 126:1609-1621 (2006).
Hansson et al.; "Epidermal Overexpression of Stratum Corneum Chymotryptic Enzyme in Mice: A Model for Chronic Itchy Dermatitis"; J. Invest. Dermatol.; 118(3):444-449 (2002).
Vasilopoulos et al.; "Genetic Association Between an AACC Insertion in the 3'UTR of the Stratum Corneum Chymotryptic Enzyme Gene and Atopic Dermatitis"; J. Invest. Dermatol.; 123:62-66 (2004).
Von Elert et al., "Cyanopeptolin 954, a Chlorine-Containing Chymotrypsin Inhibitor of Microcystis aeruginosa NIVA Cya 43," J. Nat. Prod. 68(9):1324-1327 (2005).
Franzke et al., "Antileukoprotease Inhibits Stratum Corneum Chymotryptic Enzyme," The Journal of Biological Chemistry 271(36):21886-21890 (Sep. 6, 1996).
McDonough et al., "New Structural Insights into the Inhibition of Serine Protease by Cyclic Peptides from Bacteria," Chem & Biol 10(10):898-900 (Oct. 2003).
Namikoshi et al., "Bioactive compounds produced by cyanobacteria," J Ind Microbiol 17(5-6):373-384(1996).
Itou et al, "Oscillapeptins A to F, Serine Protease Inhibitors from the Three Strains of Oscillatoria agardhii," Tetrahedron 55(22):6871-6882 (1999).
Harada et al., "Co-production of Microcystins and Aeruginopeptins by Natural Cyanobacterial Bloom," Environ Toxicol 16(4):298-305 (2001).
Grach et al., "Protease inhibitors from a Slovenian Lake Bled toxic waterbloom of the cyanobacterium Planktothrix rubescens," Tetrahedron 59(42):8329-8336 (2003).
Matern et al., "Binding Structure of Elastase Inhibitor Scyptolin A," Chemistry & Biology 10(10):997-1001 (2003).

(Continued)

*Primary Examiner* — David Lukton
(74) *Attorney, Agent, or Firm* — Sophie Binet Cross

(57) ABSTRACT

The present application relates to cyclic depsipeptides, or derivatives thereof, having the structure of formula (I), and uses thereof, e.g. as inhibitors of kallikrein 7 and human neutrophil elastase.

17 Claims, 12 Drawing Sheets

(56) References Cited

OTHER PUBLICATIONS

Nakanishi et al., "Structure of Porcine Pancreatic Elastase Complexed with FR901277, a Novel Macrocyclic Inhibitor of Elastases, at 1.6A Resolution" Biopolymers 53(5):434-445 (2000).
Banker R et al., "Inhibitors of Serine Proteases from a Waterbloom of the Cyanobacterium Microcystis sp," Tetrahedron 55(35):10835-10844 (Aug. 27, 1999).
Bonjouklian R et al., "A90720A, A Serine Protease Inhibitor Isolated From A Terrestrial Blue-Green Alga Microchaete loktakensis," Tetrahedron 52(2):395-404 (Jan. 8, 1996).
Reshef V et al., "Protease inhibitors from a water bloom of the cyanobacterium Microcystis aeruginosa," Tetrahedron 57(14):2885-2894 (Apr. 2, 2001).
Fairlie D P et al., "Conformational Selection of Inhibitors and Substrates by Proteolytic Enzymes: Implications for Drug Design and Polypeptide Processing," J. Med. Chem. 43(7):1271-1281 (2000).
Matthew Susan et al., "Lyngbyastatin 4, a dolastatin 13 analogue with elastase and chymotrypsin inhibitory activity from the marine cyanobacterium Lyngbya confervoides," J. Nat. Prod. 70(1):124-127 (Jan. 2007).
Matsuda H., "Structures of serine protease inhibitors from freshwater blue-green algae," Tennen Yuki Kagobutsu Toronkai Koen Yoshishu 35:654-661 (1993).
Radau G., "Serine proteases inhibiting cyanopeptides," Pharmazie 55(8):555-560 (Aug. 2000).
Egelrud T., "Purification and preliminary Characterization of Stratum Corneum Chymotryptic Enzyme: A Proteinase that may be involved in desquamation," J. Invest. Dermatol.101(2):200-204 (1993).
Fujii et al., "Development of a Method for Determining the Absolute Configuration of Constituent Amino Acids in Peptides Using LC/MS," Tennen Yuki Kagobutsu Toronkai Koen Yoshishu 39:223-228 (1997).
Yokokawa et. al., 'Synthetic studies towards 3-Amino-6-hydroxy-2-piperidone (Ahp)-Containing Cyclic Depsipeptides', Peptide Science 38:33-36 (2001).
Pearce et al., "Failure modes in anticancer drug discovery and development," Cancer Drug Design and Discovery 424-435 (2008).
Custom Peptide Synthesis, "Designing Custom Peptides," SIGMA Genosys, 1-2, (Dec. 16, 2004).
Residue Definition, http://dictionary.reference.com/browse/residue, (2009), pp. 1-4.
Matsuda et al., Tennen Yuki Kagobutsu Toronkai Koen Yoshishu 35:654-661.
Johannesson et al, "Angiotensin II Analogues Encompassing 5, 9- and 5,10-Fused Thiazabicycloalkane Tripeptide Mimetics, Journal of Medicinal Chemistry 42(22)" 4524-4537 (Nov. 1999).
Lautenschläger, "Fettstoffe—die Basis der Hautpflege" Kosmetische Praxis, 6:6-8 (2003).
Stawikowski et al., "A novel strategy for the solid-phase synthesis of cyclic lipodepsipeptides", Tetrahedron Letters 47 (2006) 8587-8590.
Bourel-Bonnet et al., "Solid-Phase Total Synthesis of Kahalalide A and Related Analogues", Journal of Medicinal Chemistry 2005, 48, 1330-1335.
Stolze et al., "Development of a Solid-Phase Approach to the Natural Product Class of Ahp-Containing Cyclodepsipeptides", European Journal of Organic Chemistry 2012, 1616-1625.
Rudinger, J., "Characteristics of the amino acids as components of a peptide hormone sequence," Peptide Hormones, JA Parsons Edition, University Park Press, Jun. 1-7, 1976.
Schinzel and Drueckes, "The phosphate recognition site of *Escherichia coli* maltodextrin phosphorylase," FEBS 286 (1,2)125-128 (Jul. 1991).
Berendsen, Herman J.C., "A Glimpse of the Holy Grail?" Science 282(5389):642-643 (Oct. 23, 1998).
Voet and Voet, Biochemistry Second Edition John Wiley & Sons, Inc. 1995 235-241.

Ngo et al., "Computational Complexity, Protein Structure Prediction, and the Levinthal Paradox," The Protein Folding Problem and Tertiary Structure Prediction, K. Merc Jr. and S. Le Grand Edition, 491-495 (1994).
Bradley and Barrick ,"Limits of Cooperativity in a Structurally Modular Protein: Response of the Notch Ankyrin Domain to Analogous Alanine Substitutions in Each Repeat," J. Mol. Biol. 324:373-386 (2002).
Sporn and Suh, "Chemoprevention of cancer" Carcinogenesis 21(3):525-530 (2000).
Auerbach et al., "Angiogenesis assays: Problems and pitfalls," Cancer and Metastasis Reviews 19:167-172 (2000).
Gura, Trisha, "Systems for Identifying New Drugs Are Often Faulty," Science 278(5340):1041-1042 (Nov. 1997).
Jain, Rakesh K., "Barriers to Drug Deliver in Solid Tumors," Scientific American 58-65 (Jul. 1994).
Cancer Drug Design and Discovery Neidle Stephen, ed. (Elsevier Academic Press, 2008) pp. 427-431.
Tsukamoto et.al., 'MicrocystilideA: A Novel Cell-Differentiation-Prompting Depsipeptide from Microcystis aeruginosa NO-15-1840', J. Am. Chem. Soc. 115:11046-11047 (1993).
Stolze et al., "Solid phase total synthesis of the 3-amino-6-hydroxy-2-piperidone (Ahp) cyclodepsipeptide and protease inhibitor Symplocamide A", Chemical Communications 46:8857-8859 (2010.
Yoshiya et al., "O-Acyl isopeptide method" for peptide synthesis: synthesis of forty kinds of "O-acyl isodipeptide unit" Boc-Ser/Thr(Fmoc-Xaa)-OH, Organic & Biomolecular Chemistry, 2007, 5, 1720-1730.
Olsen et al.,'Synthesis of Nalpha, Nbeta-protected Ndelta-Hydroxy-L-ornitine from L-Glutamic Acid', J. Org. Chem. 1994, 49, 3527-3534.
Zainuddin et. al., 'Cyclic Depsipeptides, Ichthyopeptins A and B, from Microcystis ichthyoblabe', J. Nat. Prod., 2007, 70, 7 1084-1088.
Ishida et. al., 'Micropeptins 88-A to 88-F, Chymotrypsin Inhibitors from the Cyanobacterium Microcystis aeruginosa (NIES-88)', Tetrahedron, 54, 21, 1998, 5545-5556.
Okumura et. al., 'Homotyrosine-Containing Cyanopeptolins 880 and 960 and Anabaenopeptins 908 and 915 from Planktothrix agardhii CYA 126/8', Journal of Natural Products 2009, 72, 1, 172-176.
Seo et.al., 'Total Synthesis of Halicylindramide A', Journal of Organic Chemistry 2009, 74, 2, 906-909.
Cochrane et. al., 'Total Synthesis and Assignment of the Side Chain Stereochemistry of Li-F04a: An Antimicrobial Cyclic Depsipeptide', Organic letters 2010, 12, 15, 3394-3397.
Yokokawa et al. , 'Synthetic studies of the cyclic depsipeptides bearing the 3-amino-6-hydroxy-2-piperidone (Ahp) unit. Total synthesis of the proposed structure of micropeptin T-20', Tetrahedron 61:1459-1480 (2005).
Yokokawa et. al., 'Synthetic studies towards 3-Amino-6-hydroxy-2-piperidone (Ahp)-Containing Cyclic Depsipeptides', The Japanese Peptide Science 38:33-36 (2002).
Yokokawa et. al., 'Synthetic studies of micropeptin T-20, a novel 3-amino-6-hydroxy-2-piperidone (Ahp)-containing cyclic depsipeptide', Tetrahedron Letters 42:5903-5908 (2001).
Tennen Yuki Kagobutsu Toronkai Koen Yoshishu 39:223-228 (1997). (Japanese article).
Harada et al., Application of D,L-FDLA Derivatization to Determine of Absolute Configuration of Constituent Amino Acids in Peptide by Advanced Marfey's Method,Tetrahedron Letters 37(17):3001-3004 (1996).
Ekholm and Egelrud "Stratum corneum chymotryptic enzyme in psoriasis," Arch of Dermatol Res 291:195-200 (1999).
Itou et.al., "Oscillapeptins A to F, Serine Protease Inhibitors from the Three Strains of Oscillatoria agardhii", Tetrahedron 55(22):6871-6882 (1999).
Yokokawa and Shioiri, 'Total synthesis of somamide A, an Ahp (3-amino-6-hydroxy-2-piperidone)-containing cyclic depsipeptide', Tetrahedron Letters 43(48):8673-8677 (2002).
Benson and Namjoshi "Proteins and Peptides: Strategies for Delivery to and Across the Skin", Journal of Pharmaceutical Sciences 97(9):3591-3610 (Sep. 2008).

(56) References Cited

OTHER PUBLICATIONS

Pena et. al., "Structural Rheology of a Model Ointment", Pharmaceutical Research 11(6):875-881 (1994).

Bos and Meinardi, "The 500 Dalton rule for the skin penetration of chemical compounds and drugs", Experimental Dermatology 9:165-169 (2000).

* cited by examiner

CYCLIC DEPSIPEPTIDES

FIELD OF THE INVENTION

The present invention relates to cyclic depsipeptides, or a derivatives thereof.

BACKGROUND OF THE INVENTION

Kallikrein 7 is a S1 serine protease of the kallikrein gene family displaying a chymotrypsin like activity. Human kallikrein 7 (hK7, KLK7 or stratum corneum chymotryptic enzyme (SCCE), Swissprot P49862) plays an important role in skin physiology (1, 2, 3). It is mainly expressed in the skin and has been reported to play an important role in skin physiology. hK7 is involved in the degradation of the intercellular cohesive structures in cornified squamous epithelia in the process of desquamation. The desquamation process is well regulated and delicately balanced with the de novo production of corneocytes to maintain a constant thickness of the stratum corneum, the outermost layer of the skin critically involved in skin barrier function. In this regard, hK7 is reported to be able to cleave the corneodesmosomal proteins corneodesmosin and desmocollin 1 (4, 5, 6). The degradation of both corneodesmosomes is required for desquamation. In addition, very recently it has been shown that the two lipid processing enzymes β-glucocerebrosidase and acidic sphingomyelinase can be degraded by hK7 (7). Both lipid processing enzymes are co-secreted with their substrates glucosylceramides and sphingomyelin and process these polar lipid precursors into their more non-polar products e.g. ceramides, which are subsequently incorporated into the extracellular lamellar membranes. The lamellar membrane architecture is critical for a functional skin barrier. Finally, hK7 has been shown to activate Interleukin-1β (IL-1β) precursor to its active form in vitro (8). Since keratinocytes express IL-1β but not the active form of the specific IL-1β converting enzyme (ICE or caspase 1), it is proposed that IL-1β activation in human epidermis occurs via another protease, a potential candidate being hK7.

Recent studies link an increased activity of hK7 to inflammatory skin diseases like atopic dermatitis, psoriasis or Netherton's syndrome. This might lead to an uncontrolled degradation of corneodesmosomes resulting in a miss-regulated desquamation, an enhanced degradation of lipid processing enzymes resulting in a disturbed lamellar membrane architecture or an uncontrolled activation of the proinflammatory cytokine IL-1β. The net result would be an impaired skin barrier function and inflammation (see also WO-A-20041108139).

Due to the fact that the hK7 activity is controlled at several levels, various factors might be responsible for an increased hK7 activity in inflammatory skin diseases. Firstly, the amount of protease being expressed might be influenced by genetic factors. Such a genetic link, a polymorphism in the 3'-UTR in the hK7 gene, was recently described (9). The authors hypothesise that the described 4 base pair insertion in the 3'-UTR of the kallikrein 7 gene stabilizes the hK7 mRNA and results in an overexpression of hK7. Secondly, since hK7 is secreted via lamellar bodies to the stratum corneum extracellular space as zymogen and it is not able to autoactivate, it needs to be activated by another protease e.g. hK5 (5). Uncontrolled activity of such an activating enzyme might result in an overactivation of hK7. Thirdly, activated hK7 can be inhibited by natural inhibitors like LEKTI, ALP or elafin (10, 11). The decreased expression or the lack of such inhibitors might result in an enhanced activity of hK7. Recently it was found, that mutations in the spink5 gene, coding for LEKTI, are causative for Netherton's syndrome (12) and a single point mutation in the gene is linked to atopic dermatitis (13, 14). Finally, another level of controlling the activity of hK7 is the pH. hK7 has a neutral to slightly alkaline pH optimum (2) and there is a pH gradient from neutral to acidic from the innermost to the outermost layers in the skin. Environmental factors like soap might result in a pH increase in the outermost layers of the stratum corneum towards the pH optimum of hK7 thereby increasing the hK7 activity.

The hypothesis that an increased activity of hK7 is linked to skin diseases with an impaired skin barrier including inflammatory and hyperpoliferative skin diseases is supported by the following studies: Firstly, Netherton's syndrome patients show a phenotype dependent increase in serine protease activity, a decrease in corneodesmosomes, a decrease in the lipid processing enzymes β-glucocerebrosidase and acidic sphingomyelinase, and an impaired barrier function (15, 16). Secondly, a transgenic mice overexpressing human kallikrein 7 shows a skin phenotype similar to that found in patients with atopic dermatitis (17, 18, 19). Thirdly, in the skin of atopic dermatitis and psoriasis patients elevated levels of hK7 were described (17, 20). Furthermore, increased activity of $K_7$ and thus epithelial barrier dysfunction may also play an important role in the pathology of other epithelial diseases such as inflammatory bowel disease and Crohn's disease.

Therefore, hK7 is considered to be a potential target for the treatment of diseases involved with epithelial dysfunction such as inflammatory and/or hyperpoliferative and pruritic skin diseases like atopic dermatitis, psoriasis, Netherton's syndrome or other pruritic dermatoses such as prurigo nodularis, unspecified itch of the elderly as well as other diseases with epithelial barrier dysfunction such as inflammatory bowel disease and Crohn's disease and there is a need for specific modulators (agonists or inhibitors) thereof.

Human neutrophil elastase (HNE, also know as human leukocyte elastase, HLE) belongs to the chymotrypsin family of serine proteinases. Its catalytic activity is optimal around pH 7, and the catalytic site is composed of three hydrogen-bonded amino acid residues: His57, Asp102, and Ser195 (in chymotrypsin numbering), which form the so-called catalytic triad. The enzyme is composed of a single peptide chain of 218 amino acid residues and four disulfide bridges. It shows 30 to 40% sequence identity with other elastinolytic or non-elastinolytic serine proteinases. HNE preferentially cleaves the oxidized insulin B chain with Val at the P1 position, but it also hydrolyzes bonds with Ala, Ser, or Cys in the P1 position.

HNE is located in the azurophilic granules of polymorphonuclear leukocytes (PMNLs), where the HNE concentration is rather high (3 µg of enzyme/106 cells). The major physiological function is to digest bacteria and immune complexes and to take part in the host defense process. HNE aids in the migration of neutrophils from blood to various tissues such as the airways in response to chemotactic factors. HNE also takes part in wound healing, tissue repair, and in the apoptosis of PMNLs.

In addition to elastin (highly flexible and highly hydrophobic component of lung connective tissue, arteries, skin, and ligaments), HNE cleaves many proteins with important biological functions, including different types of collagens, membrane proteins, and cartilage proteoglycans. HNE also indirectly favours the breakdown of extracellular matrix proteins by activating procollagenase, prostromelysin, and progelatinase. HNE inactivates a number of endogenous proteinase inhibitors such as α2-antiplasmin, α1-antichymotrypsin, antithrombin, and tissue inhibitor of metalloproteinases.

Extracellular elastase activity is tightly controlled in the pulmonary system by α1-protease inhibitor (α1PI), responsible for protection of the lower airways from elastolytic damage, whereas the secretory leukocyte proteinase inhibitor protects mainly the upper airways. In a number of pulmonary pathophysiological states, e.g., pulmonary emphysema, chronic bronchitis, and cystic fibrosis, endogenous elastase inhibitors are inefficient in regulating HNE activity.

HNE is considered to be the primary source of tissue damage associated with inflammatory diseases such as pulmonary emphysema, adult respiratory distress syndrome (ARDS), chronic bronchitis, chronic obstructive pulmonary disease (COPD), pulmonary hypertension, and other inflammatory diseases as well as bronchopulmonary dysplasia in premature neonates. HNE is involved in the pathogenesis of increased and abnormal airway secretions commonly associated with airway inflammatory diseases. Thus, bronchoalveolar lavage (BAL) fluid from patients with chronic bronchitis and cystic fibrosis has increased HNE activity. Furthermore, excessive elastase has been proposed to contribute not only to these chronic inflammatory diseases but also to acute inflammatory diseases such as ARDS and septic shock.

Therefore, HNE is considered to be a potential target for the treatment of diseases involved with HNE activity such as inflammatory diseases such as pulmonary emphysema, adult respiratory distress syndrome (ARDS), chronic bronchitis, chronic obstructive pulmonary disease (COPD), pulmonary hypertension, and other inflammatory diseases as well as bronchopulmonary dysplasia in premature neonates, and diseases involved with increased and abnormal airway secretions as well as acute inflammatory diseases. Thus there is a need for specific modulators (agonists or inhibitors) if HNE.

Treatment can be by local or systemic application such a creams, ointments and suppositories or by oral or sc or iv application or by inhalation, respectively.

*Chondromyces* is a genus in the family Polyangiaceae, which belongs to the order Myxococcales within the Delta-proteobacteria. Bacteria of the order Myxococcales, also called myxobacteria, are gram-negative rod-shaped bacteria with two characteristics distinguishing them from most other bacteria. They swarm on solid surfaces using an active gliding mechanism and aggregate to form fruiting bodies upon starvation (Kaiser (2003)). The present inventors have identified cyclic depsipeptide produced by *Chondromyces* that are able to specifically modulate kallikrein 7.

SUMMARY OF THE INVENTION

In one aspect the present invention relates to cyclic depsipeptides, or derivatives thereof, having the structure of formula (I):

$$\begin{array}{c} A_3-A_4-A_5-A_6 \\ | \quad\quad\quad | \\ X-A_1-A_2\text{------}O\text{------}A_7 \end{array}$$

wherein the ester bond is found between the carboxy group of A7 and the hydroxy group of A2, wherein X and $A_1$ are each independently optional, and wherein X is any chemical residue, wherein $A_1$ is a standard amino acid which is not aspartic acid or a derivative of said standard amino acid, wherein $A_2$ is threonine or serine, wherein $A_3$ is a non-basic standard amino acid or a non-basic derivative thereof, wherein $A_4$ is Ahp, dehydro-AHP, proline or a derivative thereof, wherein $A_5$ is isoleucine or valine, wherein $A_6$ is tyrosine or a derivative thereof and wherein $A_7$ is leucine, isoleucine or valine.

Alternatively, the cyclic depsipeptides of the invention, or derivatives thereof, can be depicted according to Formula (I'):

wherein X and $A_1$ are as defined in the embodiments, and wherein
R2 is H or methyl
R3 the side chain of a non-basic amino acid or a non-basic derivative thereof
R5 is the side chain of the amino acid isoleucine or valine
R6 is the side chain of tyrosine or a derivative thereof
R7 is the side chain of the amino acid leucine, isoleucine or valine
Y is either hydrogen or a methylgroup,
and wherein Ahp can be substituted by dehydro-AHP, Ahp-I, Ahp-II, proline or a derivative thereof.

The present invention also relates to a pharmaceutically acceptable salt of such a cyclic depsipeptide or a derivative thereof.

In the cyclic depsipeptides of the invention X can be H or an acyl residue, for instance $CH_3CH_2CH(CH_3)CO$, $(CH_3)_2CHCH_2CO$ or $(CH_3)_2CHCO$.

In the cyclic depsipeptides of the invention A1 can be glutamine, glutamic acid, or a derivative thereof, e.g. a glutamic nitrile or a glutamic acid ester.

In the cyclic depsipeptides of the invention A2 can be threonine or a derivative thereof.

In the cyclic depsipeptides of the invention A3 can be leucine.

In the cyclic depsipeptides of the invention A6 can be tyrosine.

In some embodiments of the cyclic depsipeptides of the invention A4 can be the Ahp derivative 3-amino-piperidin-2-one, Ahp-I or Ahp-H.

In some embodiments of the cyclic depsipeptides, or derivatives thereof, of the invention, X is $(CH_3)_2CHCO$, $A_1$ is glutamine, glutamic acid or a derivative thereof, $A_2$ is threonine, $A_3$ is leucine, $A_4$ is Ahp or a derivative thereof, $A_5$ is isoleucine or valine, $A_6$ is tyrosine or a derivative thereof and $A_7$ is isoleucine or valine.

In other embodiments of cyclic depsipeptide, or derivatives thereof of the invention X is $CH_3CH_2CH(CH_3)CO$ $A_1$ is glutamine, glutamic acid or a derivative thereof $A_2$ is threonine, $A_3$ is leucine, $A_4$ is Ahp or a derivative thereof, $A_5$ is isoleucine, $A_6$ is tyrosine or a derivative thereof and $A_7$ is isoleucine.

In yet other embodiments of cyclic depsipeptide, or derivative thereof, of the invention X is $CH_3CH_2CH(CH_3)CO$, $A_1$ is glutamine, glutamic acid or a derivative thereof, $A_2$ is threonine, A₃ is leucine, A₄ is dehydro-AHP or a derivative thereof, A₅ is isoleucine, A₆ is tyrosine or a derivative thereof, and A₇ is isoleucine.

In further embodiments of cyclic depsipeptide, or derivative thereof, of the invention X is $(CH_3)_2CHCH_2CO$, $A_1$ is glutamine, glutamic acid or a derivative thereof, $A_2$ is threonine, $A_3$ is leucine, $A_4$ is dehydro-AHP, Ahp or a derivative thereof, $A_5$ is isoleucine, $A_6$ is tyrosine or a derivative thereof, and $A_7$ is isoleucine.

The present invention moreover also relates to cyclic depsipeptides, or derivatives thereof, having the structure of formula (I)

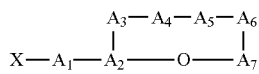

wherein the ester bond is found between the carboxy group of A7 and the hydroxy group of A2, wherein X is $(CH_3)_2CHCH_2CO$, wherein $A_1$ is glutamine, glutamic acid or a derivative thereof, wherein $A_2$ is threonine, wherein $A_3$ is leucine, wherein $A_4$ is Ahp or proline, or a derivative thereof, wherein $A_5$ is phenylalanine, wherein $A_6$ is tyrosine or a derivative thereof, and wherein $A_7$ is valine.

In particular embodiments thereof, X is $(CH_3)_2CHCH_2CO$, $A_1$ is glutamine, glutamic acid or a derivative thereof, $A_2$ is threonine, $A_3$ is leucine, $A_4$ is Ahp, or a derivative thereof, $A_5$ is phenylalanine, $A_6$ is tyrosine or a derivative thereof, and $A_7$ is valine.

In other embodiments thereof, X is $(CH_3)_2CH\,CH_2CO$, $A_1$ is glutamine, glutamic acid or a derivative thereof $A_2$ is threonine, $A_3$ is leucine, $A_4$ is proline, or a derivative thereof, $A_5$ is phenylalanine, $A_6$ is tyrosine or a derivative thereof, and $A_7$ is valine. In there embodiments, the nitrogen atom of the amid bond between A5 and A6 can be substituted with a methyl.

In the cyclic depsipeptide, or derivative thereof, of the invention A1, A2, A3, A5, A6 and A7 can be L-amino acids. Moreover, A4 can 3S,6R Ahp.

The present invention also relates to the use of the above-described depsipeptides, and derivatives thereof, as a medicament. For instance for the treatment of cancer, in particular ovarian cancer, or for the treatment of inflammatory and/or hyperpoliferative and pruritic skin diseases such as keloids, hypertrophic scars, acne, atopic dermatitis, psoriasis, pustular psoriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer, cystic fibrosis (CF), chronic obstructive pulmonary disease (COPD), pulmonary fibrosis, adult respiratory distress syndrome, chronic bronchitis, hereditary emphysema, rheumatoid arthritis, IBD, psoriasis, asthma.

In one embodiment the present invention relates to the use of the above-described depsipeptides, and derivatives thereof, as a medicament for the treatment of inflammatory and/or hyperpoliferative and pruritic skin diseases such as keloids, hypertrophic scars, acne, atopic dermatitis, psoriasis, pustular psoriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer.

In another embodiment the present invention relates to the use of the above-described depsipeptides, and derivatives thereof, as a medicament for the treatment of cystic fibrosis (CF), chronic obstructive pulmonary disease (COPD), pulmonary fibrosis, adult respiratory distress syndrome, chronic bronchitis, hereditary emphysema, rheumatoid arthritis, IBD, psoriasis, asthma.

In yet another embodiment the present invention relates to the use of the above-described depsipeptides, and derivatives thereof, as a medicament for the treatment of inflammatory and/or hyperpoliferative and pruritic skin diseases such as keloids, hypertrophic scars, acne, atopic dermatitis, psoriasis, pustular psoriasis, rosacea, Netherton's syndrome or other pruritic dermatoses such as prurigo nodularis, unspecified itch of the elderly.

The present invention also encompasses processes for producing the cyclic depsipeptide, or derivative thereof, of the invention, for instance by cultivation of a *Chondromyces* strain, a variant or a mutant thereof, in a suitable medium, and optionally chemical derivation of the so-produced cyclic depsipeptide, or by expression of the biosynthesis genes of a *Chondromyces* strain, a variant or a mutant thereof, in a heterologous microbial host strain, and optionally chemical derivation of the so-produced cyclic depsipeptide.

These processes of the invention can be performed with the strains *Chondromyces crocatus* (DSM 19329) or *Chondromyces robustus* (DSM 19330) or *Chondromyces apiculatus* (DSM 21595).

The present invention hence also relates to isolated *Chondromyces* microorganisms deposited under the accession number DSM 19329 or DSM 19330 or DSM 21595 and to cyclic depsipeptides, or derivative thereof, produced by these isolated *Chondromyces* microorganisms.

DETAILED DESCRIPTION OF THE INVENTION

Figure 1:
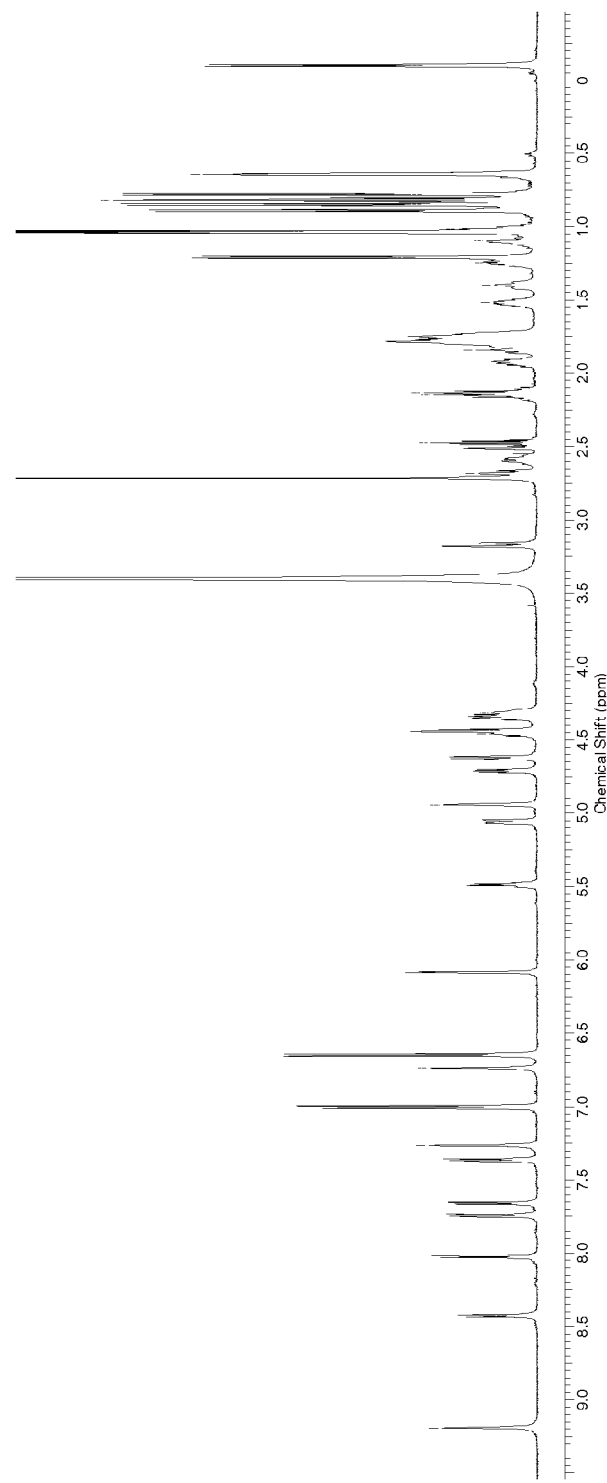
FIG. 1: ¹H-NMR spectrum of the compound of formula (II) (600 MHz, d₆-DMSO)
Figure 2:
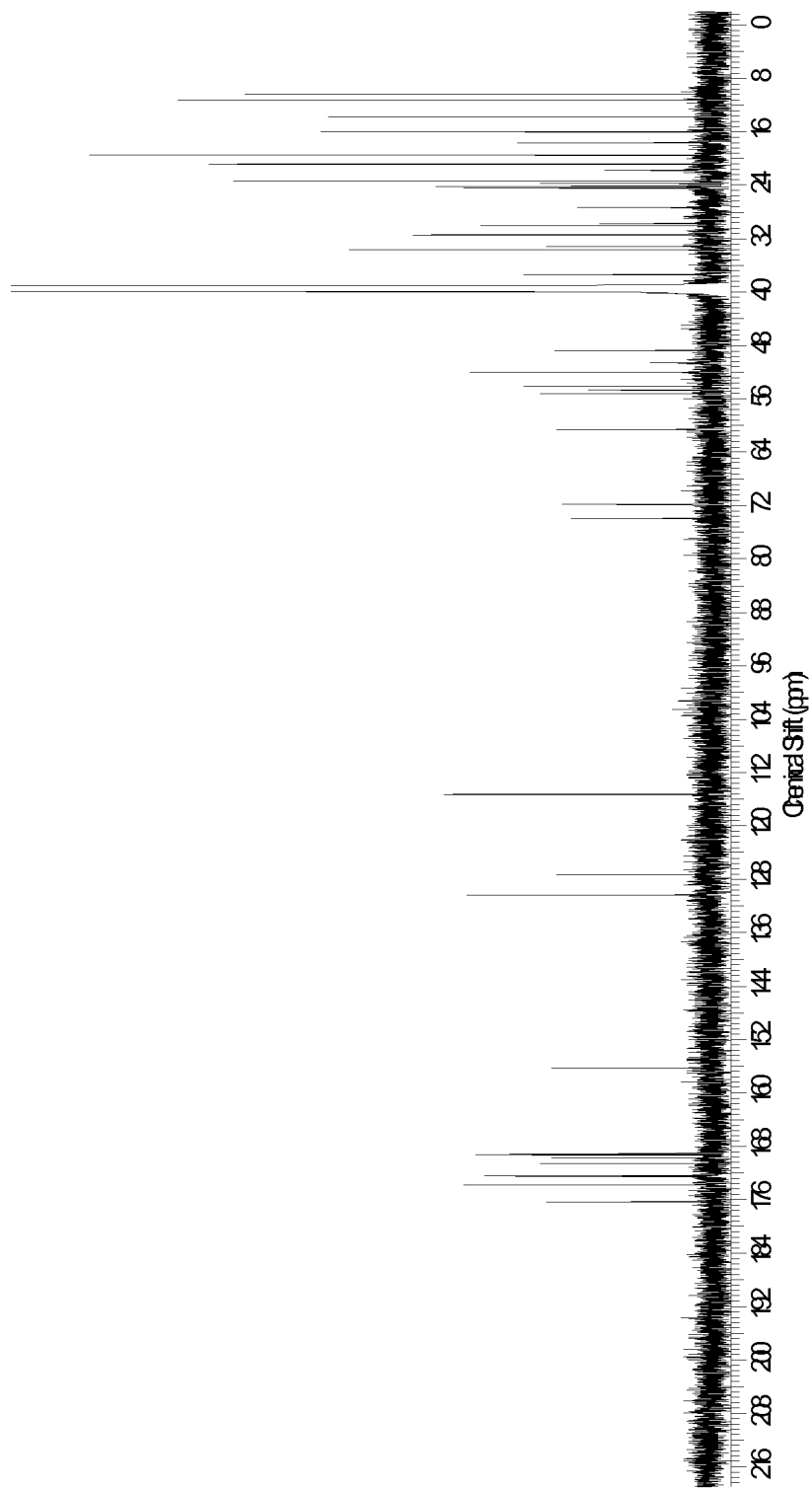
FIG. 2: ¹³C-NMR spectrum of the compound of formula (II) (150 MHz, d₆-DMSO)
Figure 3:
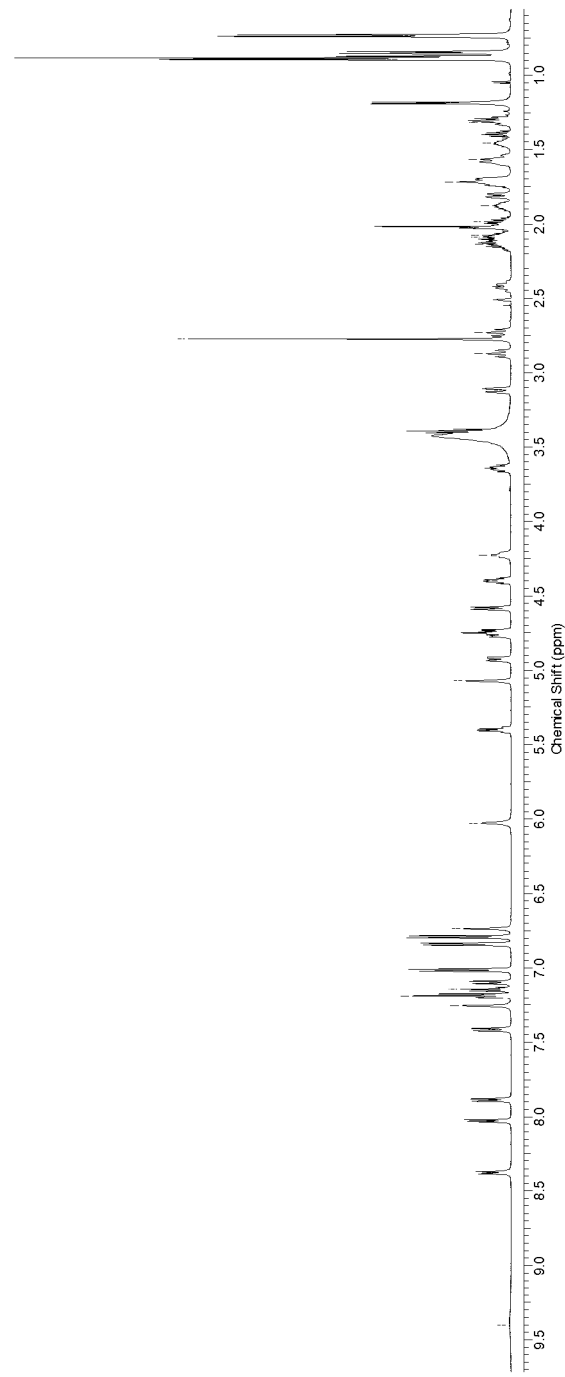
FIG. 3: ¹H-NMR spectrum of the compound of formula (VIII) (600 MHz, d₆-DMSO)
Figure 4:
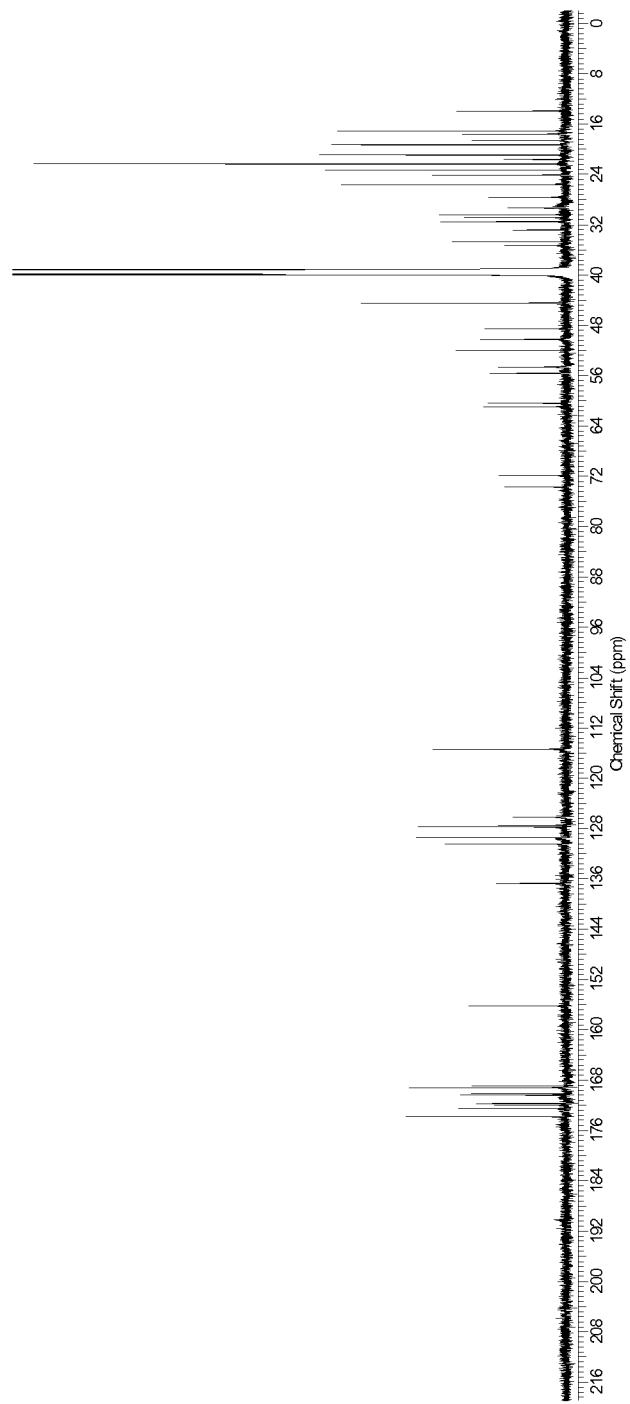
FIG. 4: ¹³C-NMR spectrum of the compound of formula (VIII) (150 MHz, d₆-DMSO).
Figure 5:
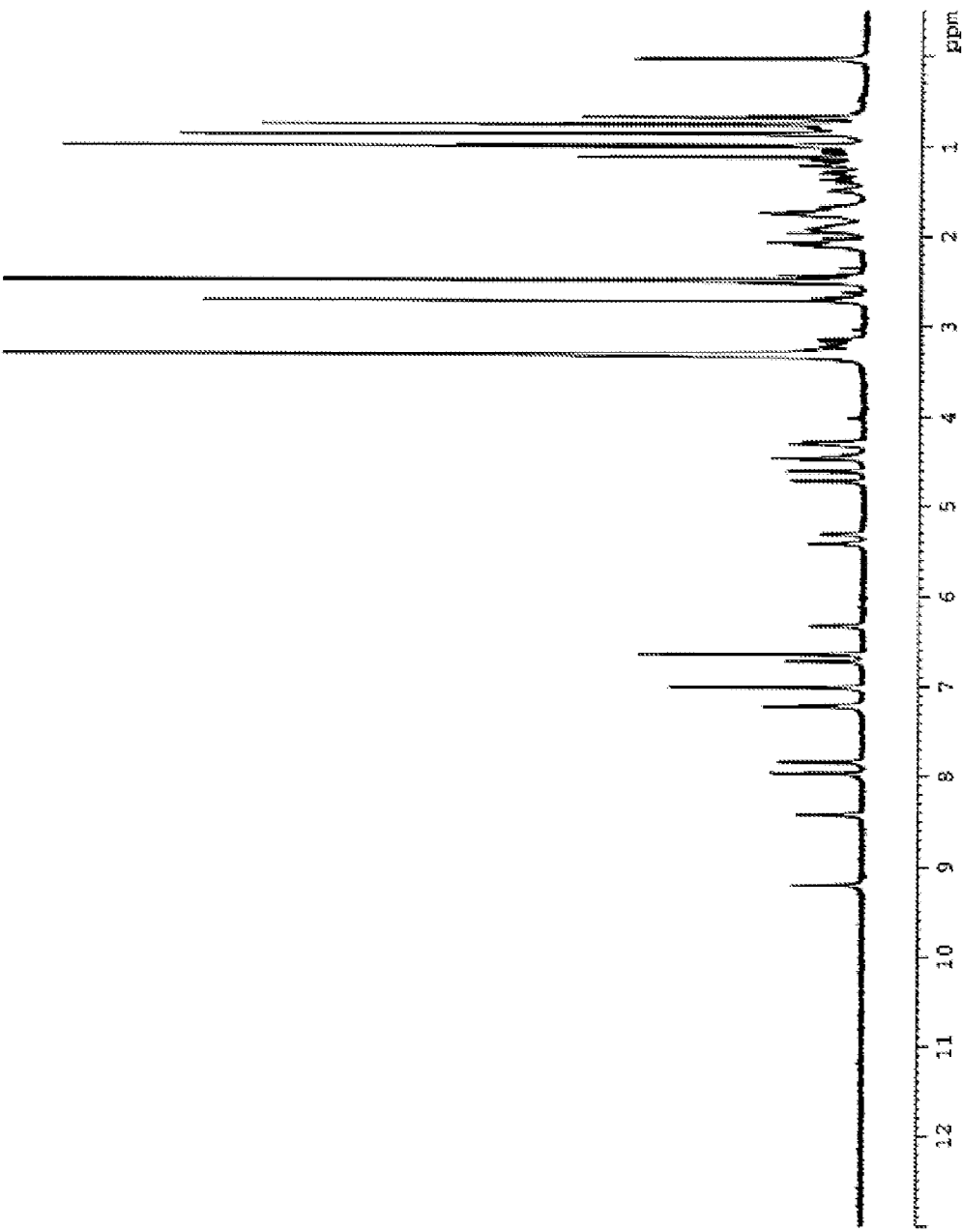
FIG. 5: ¹H-NMR spectrum of a. derivative of the cyclic depsipeptide according to formula (II) wherein the Ahp has been converted into 3-amino-piperidin-2-one (Example 4).
Figure 6:
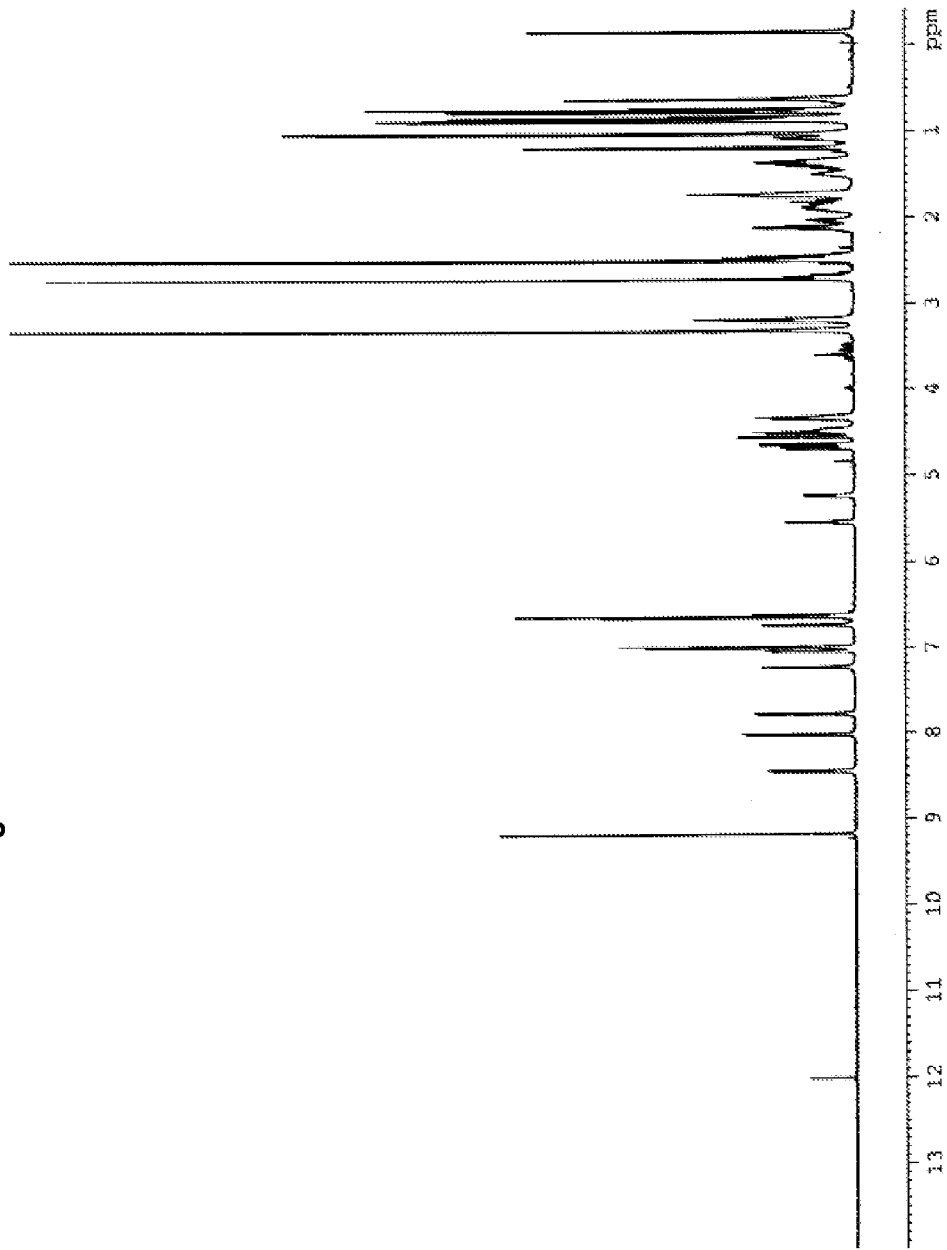
FIG. 6: ¹H NMR spectrum of a. derivative of the cyclic depsipeptide according to Example 5. (500 MHz, d₆-DMSO)
Figure 7:
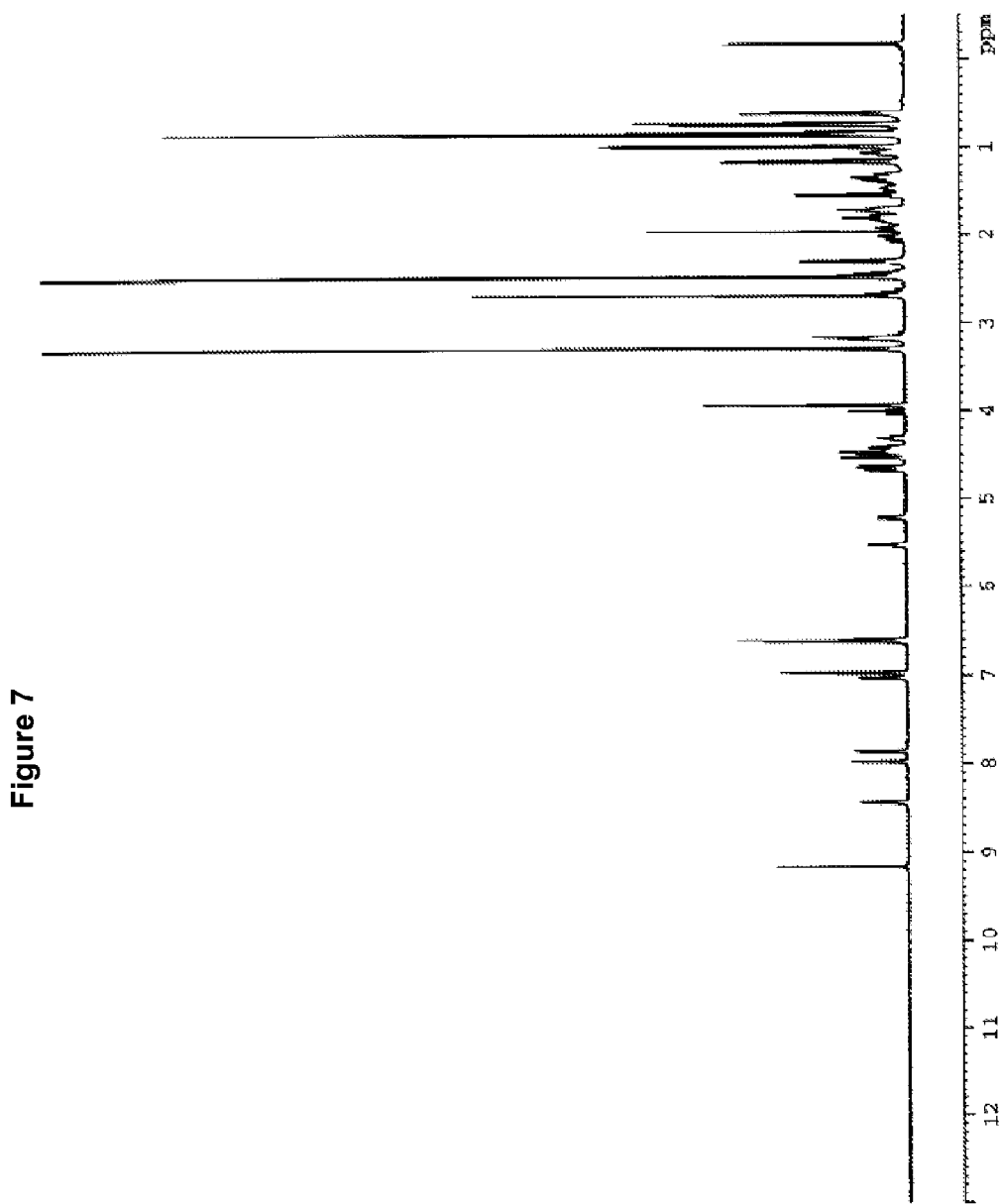
FIG. 7: ¹H-NMR spectrum of a. derivative of the cyclic depsipeptide according to Example 19. (500 MHz, d₆-DMSO)
Figure 8:
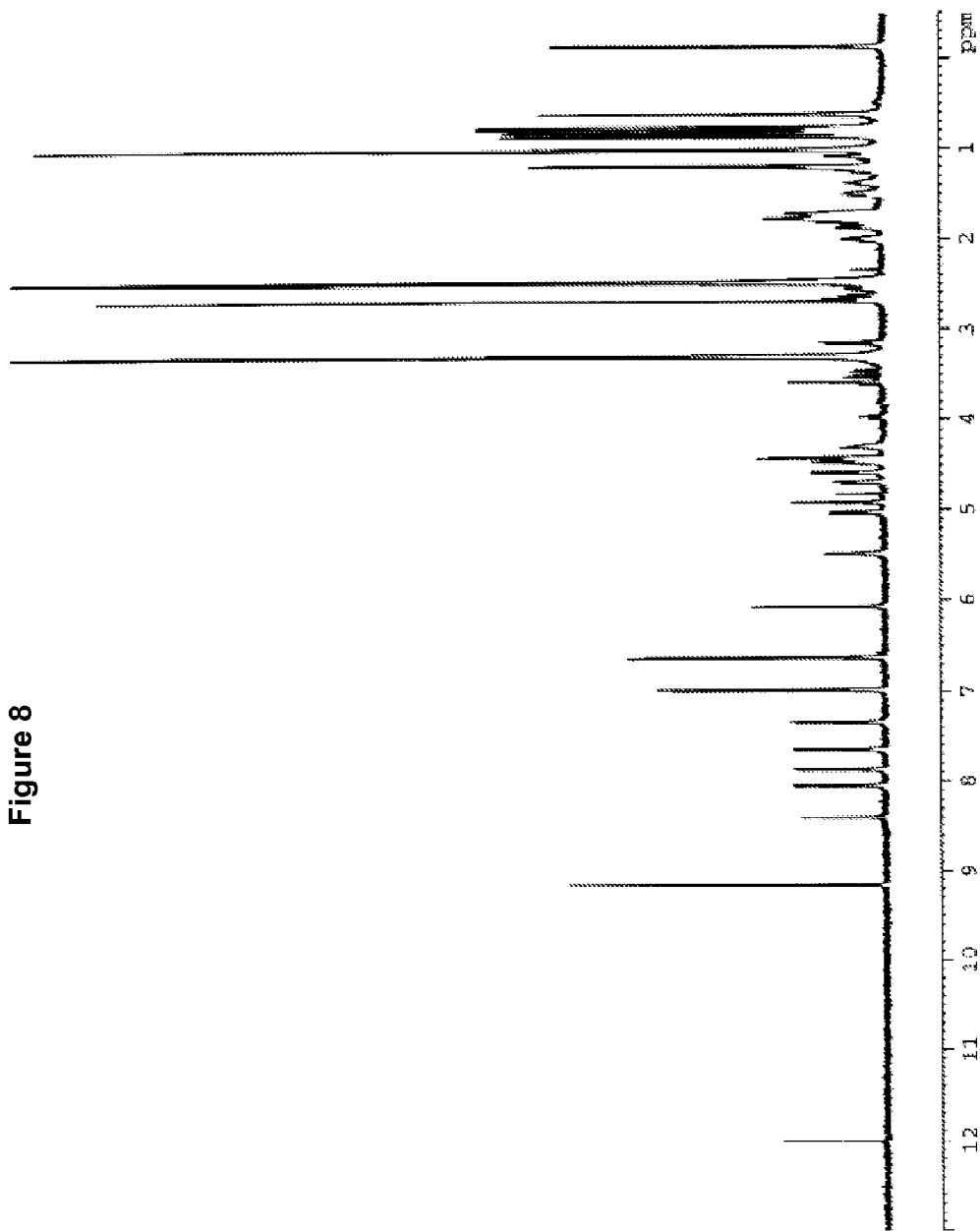
FIG. 8: ¹H-NMR spectrum of a. derivative of the cyclic depsipeptide according to Example 21. (500 MHz, d₆-DMSO)
Figure 9:
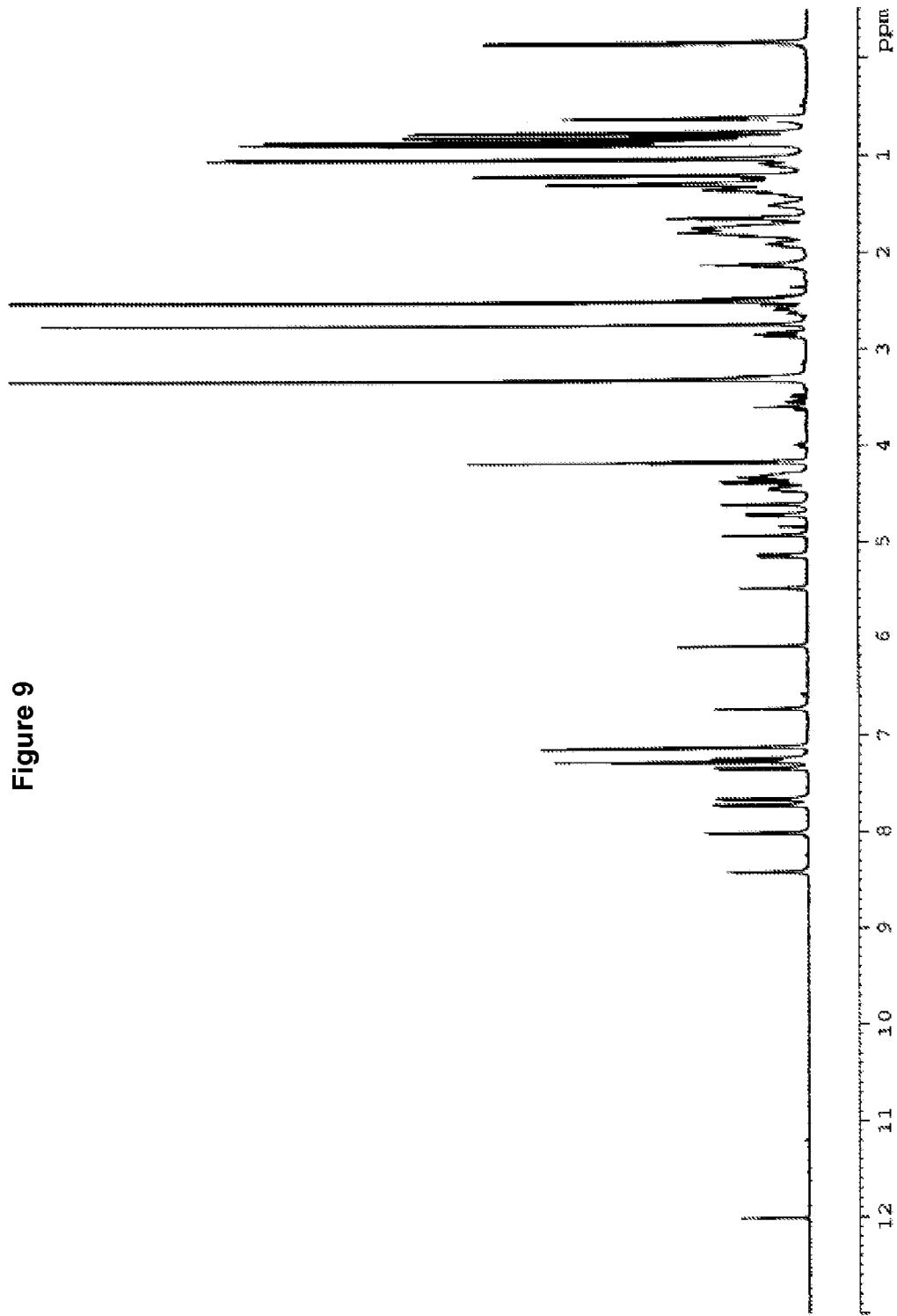
FIG. 9: ¹H NMR spectrum of a. derivative of the cyclic depsipeptide according to Example 26. (500 MHz, d₆-DMSO)
Figure 10:
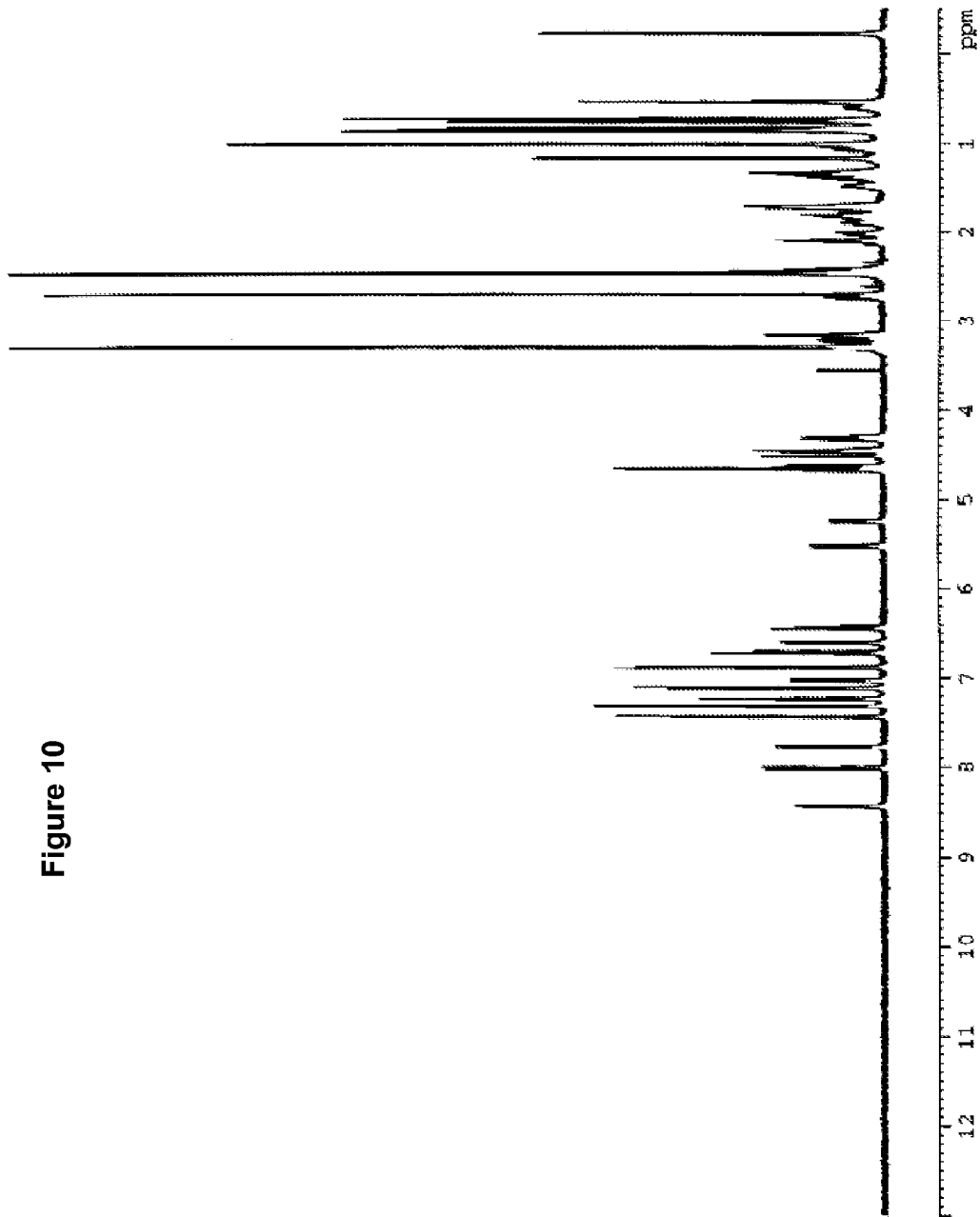
FIG. 10: ¹H-NMR spectrum of a. derivative of the cyclic depsipeptide according to Example 32. (500 MHz, d₆-DMSO)
Figure 11:
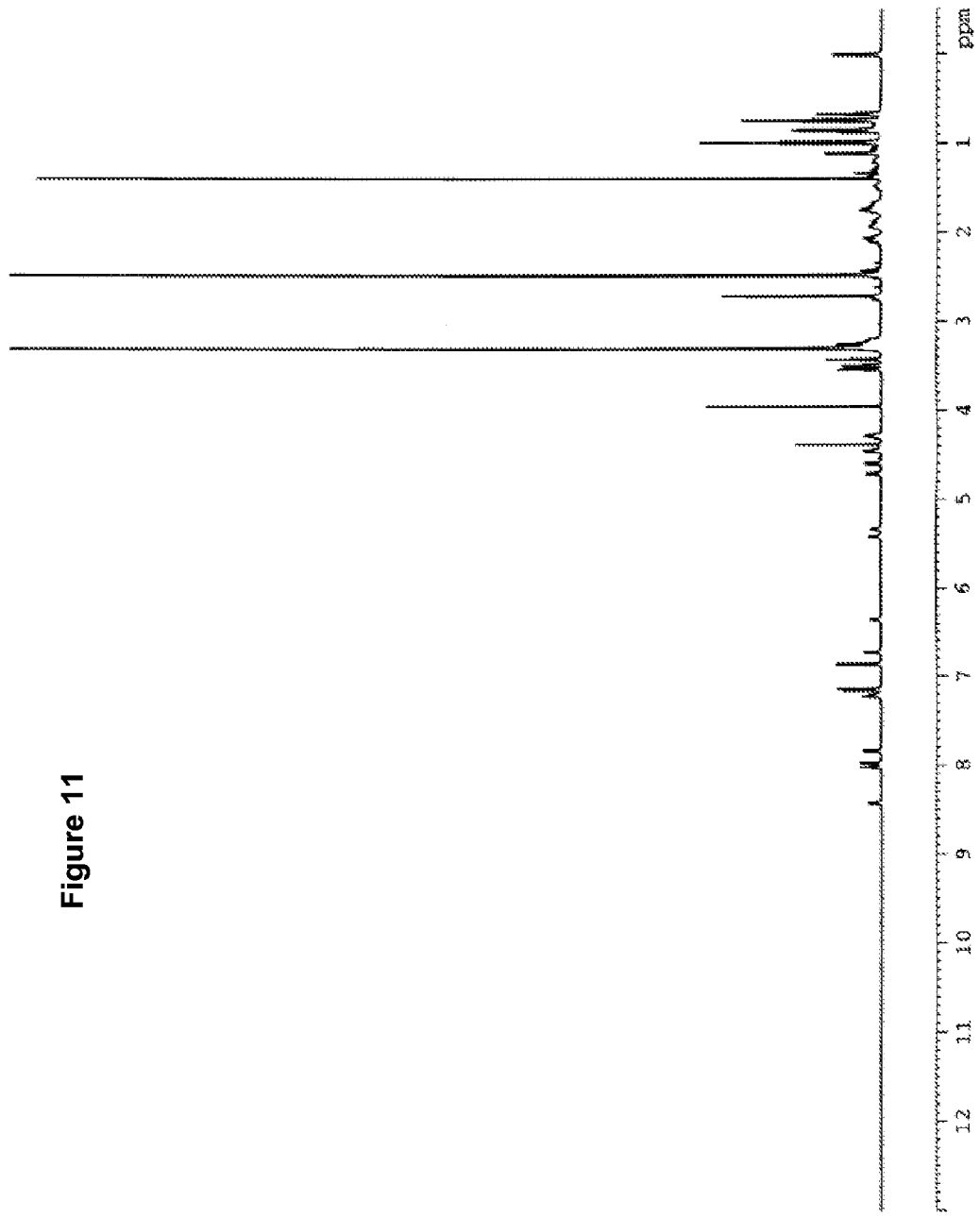
FIG. 11: ¹H-NMR spectrum of a. derivative of the cyclic depsipeptide according to Example 44. (500 MHz, d₆-DMSO)
Figure 12:
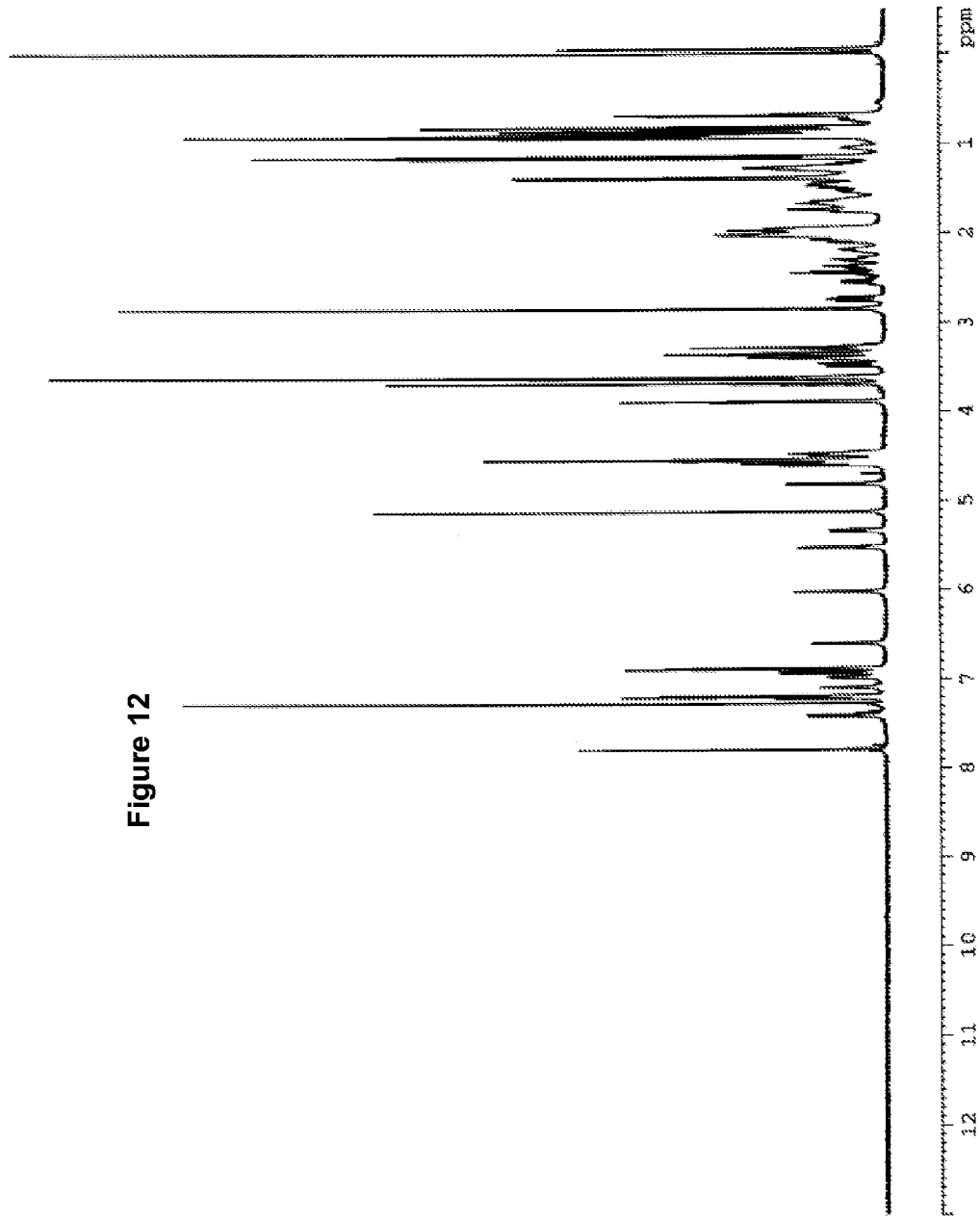
FIG. 12: ¹H-NMR spectrum of a. derivative of the cyclic depsipeptide according to Example 45 (500 MHz, d₆-DMSO)

As described herein-above and in the embodiments, the present invention relates in one aspect to cyclic depsipeptides, or a derivatives thereof, having the structure of formula (I):

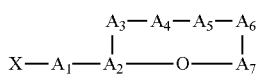

wherein the ester bond is found between the carboxy group of A7 and the hydroxy group of A2, wherein X and $A_1$ are each independently optional, and wherein X is any chemical residue, wherein $A_1$ is a standard amino acid which is not aspartic acid, wherein $A_2$ is threonine or serine, wherein $A_3$ is a non-basic standard amino acid or a non-basic derivative thereof, wherein $A_4$ is Ahp, dehydro-AHP, proline or a derivative thereof, wherein $A_5$ is isoleucine or valine, wherein $A_6$ is tyrosine or a derivative thereof and wherein $A_7$ is leucine, isoleucine or valine.

Alternatively, the cyclic depsipeptides of the invention, or a derivative thereof, can be depicted according to Formula (I'):

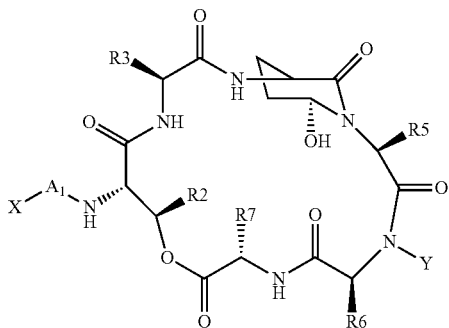

wherein X and $A_1$ are as defined in the embodiments, and wherein
R2 the side chain of the amino acid threonine or serine
R3 the side chain of a non-basic amino acid or a non-basic derivative thereof
R5 is the side chain of the amino acid isoleucine or valine
R6 is the side chain of tyrosine or a derivative thereof
R7 is the side chain of the amino acid leucine, isoleucine or valine
Y is either hydrogen or a methylgroup,
and wherein Ahp can be substituted by dehydro-AHP, Ahp-I, Ahp-II, proline or a derivative thereof.

The present invention also relates to a pharmaceutically acceptable salt of such a cyclic depsipeptide or a derivative thereof.

In the cyclic depsipeptides of the invention the nitrogen atom of the amid bond between A5 and A6 can be substituted with a methyl.

In the cyclic depsipeptides of the invention X can be H or an acyl residue, for instance $CH_3CH_2CH(CH_3)CO$, $(CH_3)_2CHCH_2CO$ or $(CH_3)_2CHCO$.

In the cyclic depsipeptides of the invention A1 can be glutamine, glutamic acid or a derivative thereof.

In the cyclic depsipeptides of the invention A2 can be threonine.

In the cyclic depsipeptides of the invention A3 can be leucine.

In the cyclic depsipeptides of the invention A6 can be tyrosine or a derivative thereof.

In some embodiments of the cyclic depsipeptides of the invention A4 can be the Ahp derivative 3-amino-piperidin-2-one, Ahp-I or Ahp-II.

In some embodiments of cyclic depsipeptide, or derivative thereof, of the invention, X is $(CH_3)_2CHCO$, $A_1$ is glutamine, glutamic acid or a derivative thereof, $A_2$ is threonine, $A_3$ is leucine, $A_4$ is Ahp or a derivative thereof, $A_5$ is isoleucine or valine, $A_6$ is tyrosine or a derivative thereof and $A_7$ is isoleucine or valine.

In other embodiments of cyclic depsipeptide, or derivative thereof, of the invention X is $CH_3CH_2CH(CH_3)CO$ $A_1$ is glutamine, glutamic acid or a derivative thereof, $A_2$ is threonine, $A_3$ is leucine, $A_4$ is Ahp or a derivative thereof, $A_5$ is isoleucine, $A_6$ is tyrosine or a derivative thereof, and $A_7$ is isoleucine.

In yet other embodiments of cyclic depsipeptide, or derivative thereof, of the invention X is $CH_3CH_2CH(CH_3)CO$, $A_1$ is glutamine, glutamic acid or a derivative thereof, $A_2$ is threonine, $A_3$ is leucine, $A_4$ is dehydro-AHP or a derivative thereof, $A_5$ is isoleucine, $A_6$ is tyrosine or a derivative thereof, and $A_7$ is isoleucine.

In further embodiments of cyclic depsipeptide, or derivative thereof, of the invention X is $(CH_3)_2CHCH_2CO$, $A_1$ is glutamine, glutamic acid or a derivative thereof, $A_2$ is threonine, $A_3$ is leucine, $A_4$ is dehydro-AHP or a derivative thereof, $A_5$ is isoleucine, $A_6$ is tyrosine or a derivative thereof, and $A_7$ is isoleucine.

The present invention moreover also relates to cyclic depsipeptides, or derivatives thereof, having the structure of formula (I)

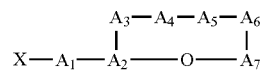

wherein the ester bond is found between the carboxy group of A7 and the hydroxy group of A2, wherein X is $(CH_3)_2CHCH_2CO$, wherein $A_1$ is glutamine, glutamic acid or a derivative thereof, wherein $A_2$ is threonine, wherein $A_3$ is leucine, wherein $A_4$ is Ahp or proline, or a derivative thereof, wherein $A_5$ is phenylalanine, wherein $A_6$ is tyrosine or a derivative thereof, and wherein $A_7$ is valine.

In particular embodiments thereof, X is $(CH_3)_2CHCH_2CO$, $A_1$ is glutamine, glutamic acid or a derivative thereof, $A_2$ is threonine, $A_3$ is leucine, $A_4$ is Ahp, or a derivative thereof, $A_5$ is phenylalanine, $A_6$ is tyrosine or a derivative thereof, and $A_7$ is valine.

In other embodiments thereof, X is $(CH_3)_2CHCH_2CO$, $A_1$ is glutamine, glutamic acid or a derivative thereof $A_2$ is threonine, $A_3$ is leucine, $A_4$ is proline, or a derivative thereof, $A_5$ is phenylalanine, $A_6$ is tyrosine or a derivative thereof, and $A_7$ is valine. In there embodiments, the nitrogen atom of the amid bond between A5 and A6 can be substituted with a methyl.

In the cyclic depsipeptide, or derivative thereof, of the invention A1, A2, A3, A5, A6 and A7 can be L-amino acids. Moreover, A4 can be 3S,6R Ahp.

A5 stands for isoleucine, phenylalanine or valine. A5 is in particular isoleucine or valine, and preferably isoleucine.

In another embodiment, A5 may be phenylalanine in particular when A4 is not Ahp, and the remaining variables are as defined in embodiment 1.

In another embodiment, A4 is 5-hydroxyproline and A5 is isoleucine, and the remaining variables are as defined in embodiment 1.

In another embodiment, A4 is Ahp and A5 is isoleucine, and the remaining variables are as defined in embodiment 1.

In another embodiment, A4 is Ahp-I and A5 is isoleucine, and the remaining variables are as defined in embodiment 1.

In another embodiment, A4 is Ahp-II and A5 is isoleucine, and the remaining variables are as defined in embodiment 1.

In another embodiment, A4 is Ahp, A5 and A7 is isoleucine, and the remaining variables are as defined in embodiment 1.

In another embodiment, A4 is Ahp-I, A5 and A7 is isoleucine, and the remaining variables are as defined in embodiment 1.

In another embodiment, A4 is Ahp-II, A5 and A7 is isoleucine, and the remaining variables are as defined in embodiment 1.

In another embodiment, A4 is 5-hydroxyproline, A5 and A7 is isoleucine, and the remaining variables are as defined in embodiment 1.

As used herein, A1 is a glutamine, glutamic acid, ornithine, or a glutamine derivative such as for example glutamic nitrile, glutamic acid ester such as $C_{1-12}$alkyl ester (e.g. glutamic acid methyl ester) or such as $C_{6-24}$aryl ester (e.g. glutamic acid phenyl or benzyl ester).

The present invention also relates to the use of the above-described depsipeptides, and derivatives thereof, as a medicament. For instance for the treatment of cancer, in particular ovarian cancer, or for the treatment of inflammatory and/or hyperpoliferative and pruritic skin diseases such as keloids, hypertrophic scars, acne, atopic dermatitis, psoriasis, Netherton's syndrome or other pruritic dermatoses such as prurigo nodularis, unspecified itch of the elderly as well as other diseases with epithelial barrier dysfunction such as inflammatory bowel disease and Crohn's disease, as well as pancreatitis.

In one embodiment the present invention relates to the use of the above-described depsipeptides, and derivatives thereof, as a medicament for the treatment of inflammatory and/or hyperpoliferative and pruritic skin diseases such as keloids, hypertrophic scars, acne, atopic dermatitis, psoriasis, pustular psoriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer.

In another embodiment the present invention relates to the use of the above-described depsipeptides, and derivatives thereof, as a medicament for the treatment of cystic fibrosis (CF), chronic obstructive pulmonary disease (COPD), pulmonary fibrosis, adult respiratory distress syndrome, chronic bronchitis, hereditary emphysema, rheumatoid arthritis, IBD, psoriasis, asthma. In yet another embodiment the present invention relates to the use of the above-described depsipeptides, and derivatives thereof, as a medicament for the treatment of inflammatory and/or hyperpoliferative and pruritic skin diseases such as keloids, hypertrophic scars, acne, atopic dermatitis, psoriasis, pustular psoriasis, rosacea, Netherton's syndrome or other pruritic dermatoses such as prurigo nodularis, unspecified itch of the elderly.

The present invention also encompasses processes for producing the cyclic depsipeptide, or derivative thereof, of the invention, for instance by cultivation of a *Chondromyces* strain, a variant or a mutant thereof, in a suitable medium, and optionally chemical derivation of the so-produced cyclic depsipeptide, or by expression of the biosynthesis genes of a *Chondromyces* strain, a variant or a mutant thereof, in a heterologous microbial host strain, and optionally chemical derivation of the so-produced cyclic depsipeptide.

These processes of the invention can be performed with the strains *Chondromyces crocatus* (DSM 19329) or *Chondromyces robustus* (DSM 19330) or *Chondromyces apiculatus* (DSM 21595).

The present invention hence also relates to isolated *Chondromyces* microorganisms deposited under the accession number DSM 19329 or DSM 19330 or DSM 21595 and to cyclic depsipeptides, or derivative thereof, produced by these isolated *Chondromyces* microorganisms.

The present invention provides:

In embodiment 1, the invention pertains to a cyclic depsipeptide, or a derivative thereof, having the structure of formula (I):

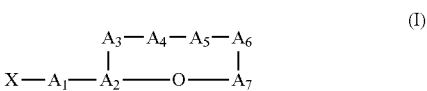

wherein an ester bond is formed between the carboxy group of A7 and the hydroxy group of A2, wherein X and $A_1$ are each independently optional, and wherein X is H or an amino group modifying moiety and may be typically selected from an aryl carbonyl residue or from an acyl residue, $A_1$ is glutamine, ornithine, glutamic acid or a derivative thereof;

$A_2$ is threonine or serine, $A_3$ is leucine, $A_4$ is Ahp, 3-amino-piperidine-2-one, dehydro-AHP, Ahp-I, Ahp-II, proline, 5-hydroxy-proline or a derivative thereof, wherein the point of fusion (with $A_3$ and $A_5$) are at the nitrogen atom and the carboxyl oxygen (by virtue of the replacement of a hydrogen atom by a bond) of the proline, and 5-hydroxyproline, wherein Ahp, 3-amino-piperidine-2-one, dehydro-AHP, Ahp-I, and Ahp-II, are as defined below, and wherein the point of fusion (with $A_3$ and $A_5$) are at the nitrogen atoms of the said compounds (by virtue of the replacement of a hydrogen atom by a bond):

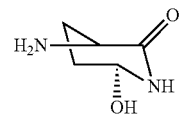

3-amino-6-hydroxy-piperidin-2-one (Ahp)

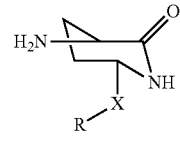

X = O or bond

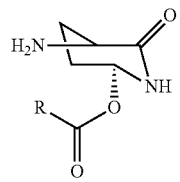

-continued

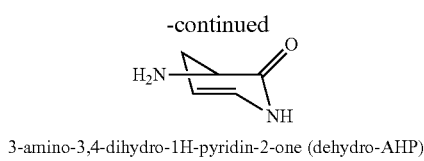
3-amino-3,4-dihydro-1H-pyridin-2-one (dehydro-AHP)

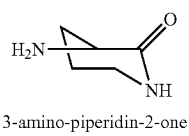
3-amino-piperidin-2-one wherein X is O or a bond, and R is an organic moiety or is a radical as defined in embodiment 3, A₅ is isoleucine, phenylalanine or valine,
A₆ is tyrosine, N-Me-tyrosine or a derivative thereof,
A₇ is leucine, isoleucine or valine,
or a pharmaceutically acceptable salt thereof In embodiment 2, the invention pertains to the depsipeptide of embodiment 1 wherein X is CH₃CH₂CH(CH₃)CO, (CH₃)₂CHCH₂CO, (CH₃)₂CHCO, CH₃CO or Phenyl-CO.

In embodiment 3, the invention pertains to the depsipeptide of embodiment 1 wherein the nitrogen atom of the amid bond between A5 and A6 is substituted with a methyl and the OH group of the tyrosine is OR, wherein R is selected from the group consisting of hydrogen, (C$_{1-12}$)alkyl, (C$_{2-12}$)alkenyl, (C$_{2-12}$)alkynyl, halo(C$_{1-12}$)alkyl, halo(C$_{2-12}$)alkenyl, halo (C$_{2-12}$)alkynyl, (C$_{1-42}$)alkoxycarbonyl, (C$_{1-12}$)alkoxy-carbonyl(C$_{1-12}$)alkyl, (C$_{1-12}$)alkylaminocarbonyl, unsubstituted or further substituted by aryl, arylalkyl, arylalkenyl or arylalkynyl, heterocyclyl and heterocyclylalkyl.

In embodiment 4, the invention pertains to the depsipeptide of embodiment 1 wherein A4 is the Ahp derivative 3-amino-piperidin-2-one, Ahp-I or Ahp-II, wherein R is selected from the group consisting of (C$_{1-12}$)alkyl, (C$_{2-12}$)al-kenyl, (C$_{2-12}$)alkynyl, halo(C$_{1-12}$)alkyl, (C$_{1-12}$)alkoxy(C$_{1-12}$)alkyl, (C$_{1-12}$)alkoxy(C$_{1-12}$)alkoxy(C$_{1-12}$)alkyl, hydroxy(C$_{1-12}$)alkyl, phenyl and phenyl(C$_{1-6}$)alkyl.

In embodiment 5, the invention pertains to the depsipeptide of embodiment 1 wherein the acyl residue X is CH₃CH₂CH (CH₃)CO or (CH₃)₂CHCO, A₁ is glutamine, glutamic acid, or a derivative thereof,
A₂ is threonine,
A₃ is leucine,
A₄ is Ahp, 3-amino-piperidine-2-one, proline, 5-hydroxy-proline or a derivative thereof,
A₅ is isoleucine,
A₆ is tyrosine, N-Me-tyrosine or a derivative thereof,
A₇ is isoleucine or valine, preferably isoleucine.

In embodiment 6, the invention pertains to the depsipeptide of any of the previous embodiments wherein A₄ is Ahp, Ahp-I, 3-amino-piperidine-2-one, proline, or 5-hydroxy-proline, preferably Ahp, Ahp-I, 3-amino-piperidine-2-one, or 5-hydroxy-proline, also preferably Ahp, Ahp-I or 5-hydroxy-proline, more preferably Ahp.

In embodiment 7, the invention pertains to a depsipeptide of embodiment 1, which is a compound in accordance to formulae A or B,

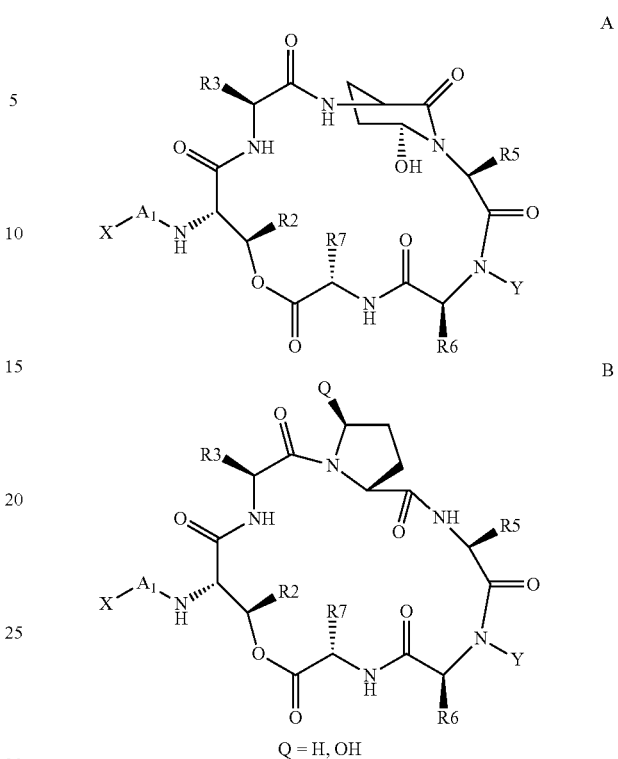

wherein X and A₁ are as defined in embodiment 1, and wherein
R2 the side chain of the amino acid threonine or serine,
R3 the side chain of leucine,
R5 is the side chain of the amino acid isoleucine or valine, in particular R5 stands for isoleucine,
R6 is the side chain of tyrosine optionally derivatized, in particular optionally derivatized on its hydroxyl group as defined in embodiment 3,
R7 is the side chain of the amino acid leucine, isoleucine or valine, in particular R7 stands for isoleucine,
Y is either hydrogen or a methyl, and Y is in particular methyl.

In embodiment 8, the invention pertains to the cyclic depsipeptide of any of the previous embodiments wherein A1, A2, A3, A5, A6 and A7 are L-amino acids.

In embodiment 9, the invention pertains to the cyclic depsipeptide of any of the previous embodiments wherein A4 is 3S,6R Ahp.

In embodiment 10, the invention pertains to the cyclic depsipeptide of any of the previous embodiments wherein A1 is a glutamine, ornithine, or a glutamine derivative as described in any of the examples of the description, and is for example selected from glutamic nitrile, glutamic acid ester such as C$_{1-12}$alkyl ester (e.g. glutamic acid methyl ester) or such as C$_{6-24}$aryl ester (e.g. glutamic acid phenyl or benzyl ester).

In embodiment 11, the invention pertains to a pharmaceutical composition comprising a cyclic depsipeptide of any of the previous embodiments in conjunction with a pharmaceutical acceptable carrier and/or ingredient.

In embodiment 12, the invention pertains to the cyclic depsipeptide of any of the previous embodiments for use as a medicament, in particular for use as described in the methods for treating a patient, such as embodiments 13-15, and the use of the said depsipeptides in the manufacture of a medicament for the treatment in a disease or disorder as described in the said method embodiments.

In embodiments 13, the invention pertains to a method of treating a subject suffering from inflammatory and/or hyperpoliferative and pruritic skin diseases such as keloids, hypertrophic scars, acne, atopic dermatitis, psoriasis, pustular psioriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer, cystic fibrosis (CF), chronic obstructive pulmonary disease (COPD), pulmonary fibrosis, adult respiratory distress syndrome, chronic bronchitis, hereditary emphysema, rheumatoid arthritis, IBD, psoriasis, asthma, comprising administering to said subject a therapeutically effective amount of a cyclic depsipeptide, or derivative thereof, of any of embodiments 1-10.

In embodiment 14, the invention pertains to a method of treating a subject according to embodiment 13, wherein the subject suffers from keloids, hypertrophic scars, acne, atopic dermatitis, psoriasis, pustular psioriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer.

In embodiment 15, the invention pertains to a method of treating a subject according to embodiment 14, wherein the subject suffers from keloids, hypertrophic scars, acne, atopic dermatitis, psoriasis, pustular psioriasis, rosacea, Netherton's syndrome or other pruritic dermatoses such as prurigo nodularis, unspecified itch of the elderly as well as other diseases with epithelial barrier dysfunction such as aged skin.

In embodiment 16, the invention pertains to a method of treating a subject according to embodiment 13, wherein the subject suffers from cystic fibrosis (CF), chronic obstructive pulmonary disease (COPD), pulmonary fibrosis, adult respiratory distress syndrome, chronic bronchitis, hereditary emphysema, rheumatoid arthritis, IBD, psoriasis, asthma.

In embodiment 17, the invention pertains to a process for producing the cyclic depsipeptide, or derivative thereof, of any of embodiments 1-10 comprising cultivation of a *Chondromyces* strain, a variant or a mutant thereof, in a suitable medium, and optionally chemical derivation of the so-produced cyclic depsipeptide.

In embodiment 18, the invention pertains to a process for producing the cyclic depsipeptide, or derivative thereof, of any of embodiments 1-10 comprising expressing the biosynthesis genes of a *Chondromyces* strain, a variant or a mutant thereof, in a heterologous microbial host strain, and optionally chemical derivation of the so-produced cyclic depsipeptide.

In embodiment 19, the invention pertains to the process of embodiment 17 or 18 wherein the strain is *Chondromyces crocatus* (DSM 19329) or *Chondromyces robustus* (DSM 19330) or *Chondromyces apiculatus* (DSM 21595).

In embodiment 20, the invention pertains to an isolated *Chondromyces* microorganism producing the cyclic depsipeptide, or derivative thereof, of any of embodiments 1-10, deposited under the accession number DSM 19329 or DSM 19330 or DSM 21595.

In embodiment 21, the invention pertains to a cyclic depsipeptide, or derivative thereof, produced by the isolated *Chondromyces* microorganism of embodiment 20 or obtained by a process according to claims 17-18.

In embodiment 22, the invention pertains to a process for the preparation of a derivative of a cyclic depsipeptide, or derivative thereof, according to embodiment 1 which comprises alternatively a)—the preparation of a derivative of a cyclic depsipeptide, or derivative thereof, according to embodiment 1 wherein A4 is

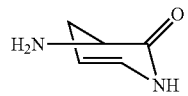

by treatment of a compound wherein A4 is

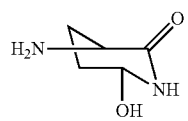

with an organic or inorganic acid, or a Lewis acid at a temperature between −78° C. and 150° C.;

b)—the preparation of a derivative of a cyclic depsipeptide, or derivative thereof, according to embodiment 1 wherein A4 is

by treatment of a compound wherein A4 is

with molecular hydrogen or source thereof in presence of a catalyst in a solvent at a temperature between −50 and 100° C.;

c)—the preparation of a derivative of a cyclic depsipeptide, or derivative thereof, according to embodiment 1 wherein A4 is

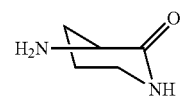

by treatment of a compound wherein A4 is

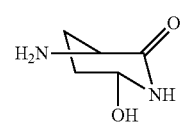

with an organic or inorganic acid or a Lewis acid, in presence of an reducing agent at a temperature between −78° C. and 150° C.; or d)—the preparation of a derivative of a cyclic depsipeptide, or derivative thereof, according to embodiment 1 wherein A4 is

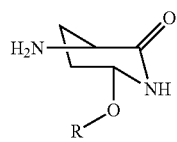

by treatment of a compound wherein A4 is

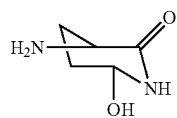

with a substituted or unsubstituted alkanol and an organic or inorganic acid, or a Lewis acid, at a temperature between −78° C. and 150° C.;
e)—the preparation of compounds wherein A1 is

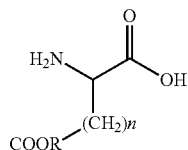

wherein n=1,2 and A4 is

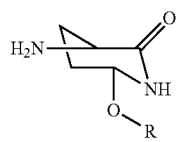

wherein R preferentially is H, alkyl, substituted alkyl, by treatment of a compound wherein A1 is Gln or Asn and A4 is

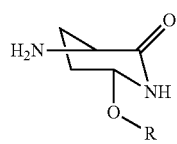

wherein R preferably is H, alkyl, substituted alkyl, with an substituted or unsubstituted alkanol and an organic or inorganic acid or a Lewis acid in a solvent or without a solvent at a temperature between −78° C. and 150° C.;
f)—the preparation of compounds wherein A1 is

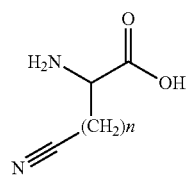

wherein R preferably is H, OH, O-alkyl, substituted O-alkyl, O-acyl, by treatment of a compound wherein A1 is Gln or Asn and A4 is

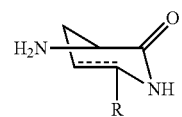

with an dehydrating agent in a solvent or without a solvent at a temperature between −78° C. and 150° C.;
g)—the preparation of compounds wherein A4 is

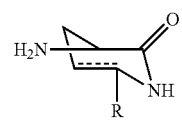

and A6 is

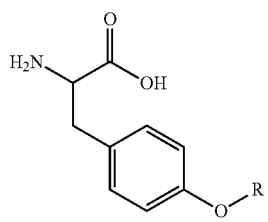

wherein R preferably is alkyl, substituted alkyl, acyl, alkoxycarbonyl by treatment of a compound wherein A4 is

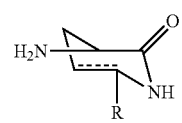

and A6 is Tyr, with an alkylating agent or an acylating agent in a solvent or without a solvent at a temperature between −78° C. and 150° C.

In embodiment 23, the invention pertains to a cyclic depsipeptide, or a derivative thereof, or a pharmaceutically acceptable salt thereof, in particular and essentially as described in the description and/or the working examples.

Specific embodiments of cyclic depsipeptides of the invention are:

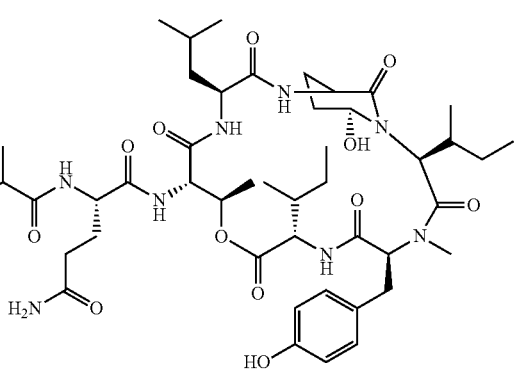

Formula (II)

Formula (III)
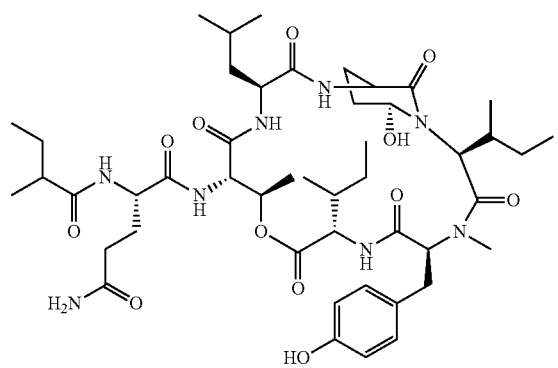
Formula (IV)
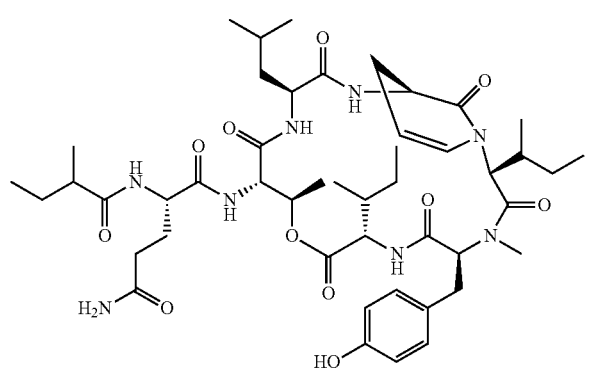
Formula (V)
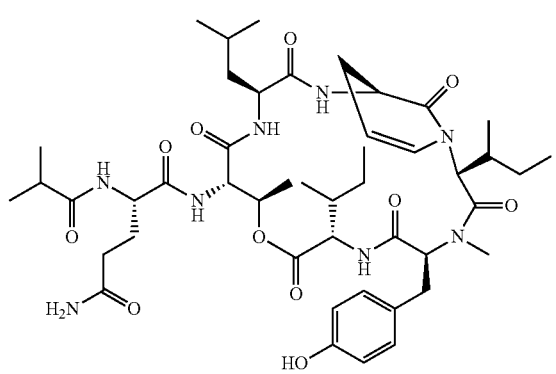
Formula (VI)
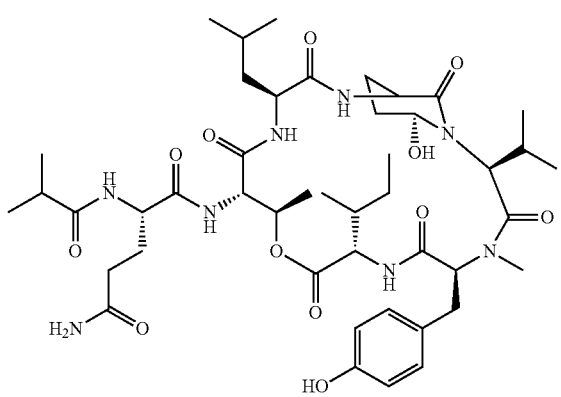
Formula (VII)
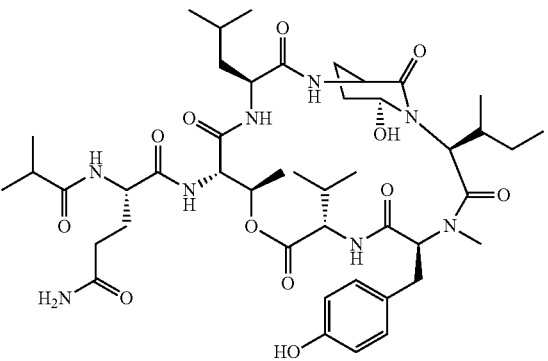
Formula (XI)
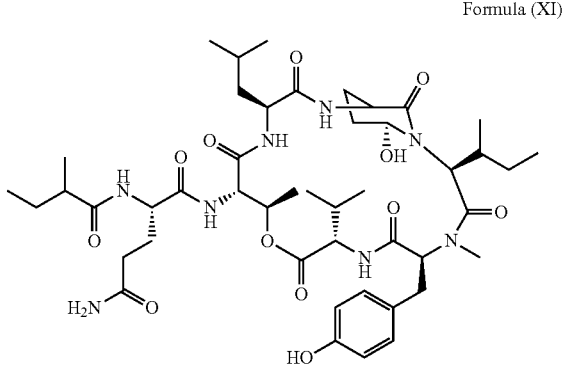
Formula (XII)
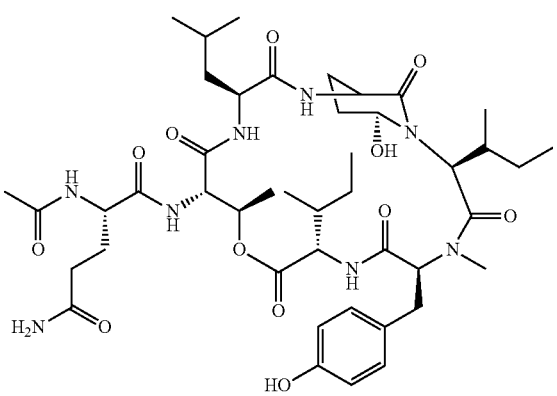
Formula (XIII)
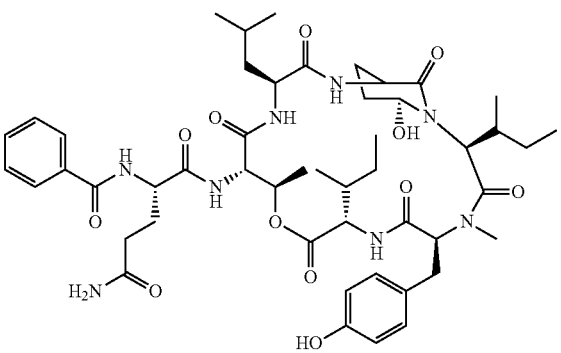

Formula (XIV)

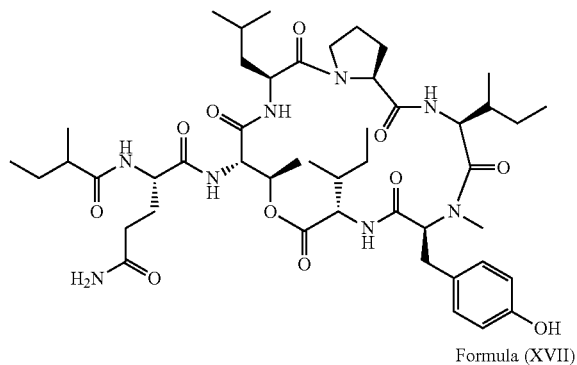

Formula (XVII)

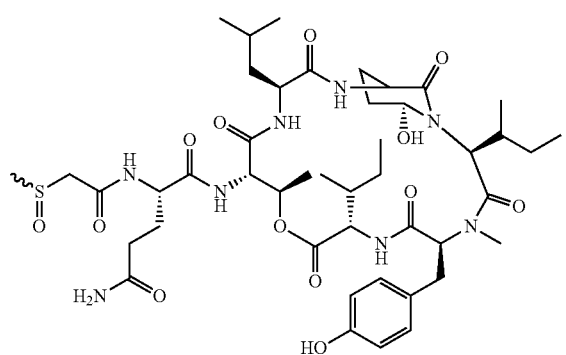

The cyclic depsipeptides of formula (II)-(VII), (XI)-(XIV) and (XVII) can be produced by the *Chondromyces crocatus* strain of the invention (DSM 19329).

Other specific embodiments of cyclic depsipeptides of the invention are:

Formula (VIII)

Formula (IX)

Formula (X)

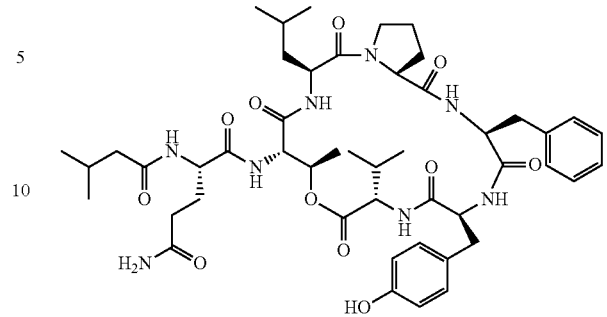

The cyclic depsipeptides of formula (VIII)-(X) can be produced by the *Chondromyces robustus* of the invention (DSM 19330).

Other specific embodiments of cyclic depsipeptides of the invention are:

Formula (XV)

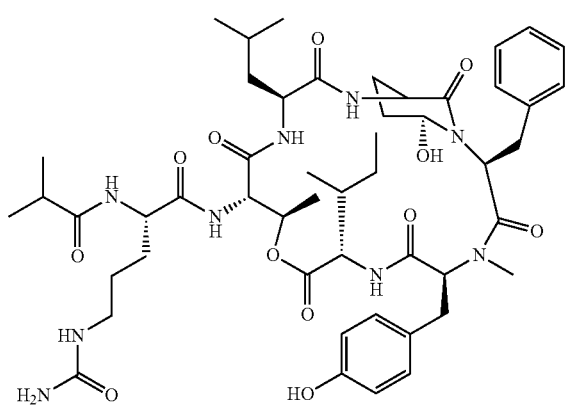

Formula (XVI)

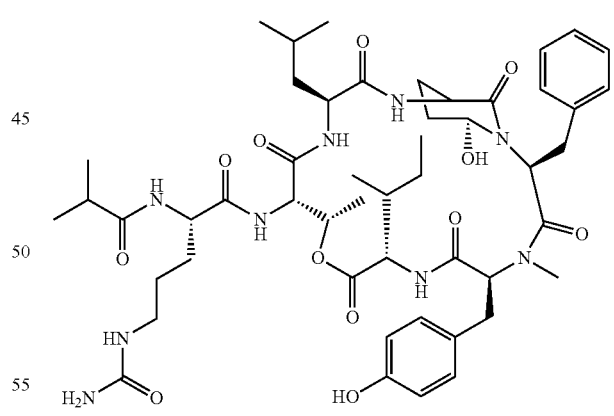

The cyclic depsipeptides of formula (XV)-(XVI) can be produced by the *Chondromyces apculatus* of the invention (DSM 21595).

LIST OF ABBREVIATIONS

Ahp 3-amino-6-hydroxy-2-piperidone
DSMZ Deutsche Sammlung von Mikroorganismen and Zellkulturen GmbH
hK7 Human kallikrein 7

HPLC High performance/pressure liquid chromatography
HTS High Throughput Screening
IC Intermediary culture
ID Identification
MB Myxobacteria
MC Main-culture
PC Pre-culture
$pO_2$ Partial pressure of oxygen in culture broth (100%=saturation with air)
rpm Rotations per minute
SCCE Stratum corneum chymotryptic enzyme
SPEX Solid phase extraction
vvm Aeration rate (Volume of air per culture volume and per minute)

A "chemical residue" can be any organic or anorganic chemical moiety. The expression "chemical residue" includes, but is not limited to substituted or unsubstituted aliphatic group, e.g. $C_1$-$C_3$ alkyl, $C_1$-$C_6$ alkyl, or $C_1$-$C_{12}$ alkyl, substituted or unsubstituted aryl, substituted or unsubstituted arylalkyl, substituted or unsubstituted heteroaryl, or halogen. For instance, a chemical residue as defined in the claims can be any of the chemical groups described herein-below.

The expression "chemical residue" includes, but is not limited to amino acids, peptides, polypeptides, proteins and the like.

Examples of anorganic chemical moiety are for instance halogens, such as Br or Cl.

An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted.

The terms "$C_1$-$C_3$ alkyl", "$C_1$-$C_6$ alkyl," or "$C_1$-$C_{12}$ alkyl," as used herein, refer to saturated, straight- or branched-chain hydrocarbon radicals containing between one and three, one and twelve, or one and six carbon atoms, respectively. Examples of $C_1$-$C_3$ alkyl radicals include methyl, ethyl, propyl and isopropyl radicals; examples of $C_1$-$C_6$ alkyl radicals include, but are not limited to, methyl, ethyl, propyl, isopropyl, n-butyl, ted-butyl, sec-butyl, n-pentyl, neopentyl and n-hexyl radicals; and examples of $C_1$-$C_{12}$ alkyl radicals include, but are not limited to, ethyl, propyl, isopropyl, hexyl, heptyl, octyl, nonyl, decyl, undecyl, dodecyl radicals and the like.

The term "substituted alkyl," as used herein, refers to an alkyl, such as a $C_1$-$C_{12}$ alkyl or $C_1$-$C_6$ alkyl group, substituted by one, two, three or more aliphatic substituents.

Suitable aliphatic substituents include, but are not limited to, —F, —Cl, —Br, —I, —OH, protected hydroxy, aliphatic ethers, aromatic ethers, oxo, —$NO_2$, —CN, —$C_1$-$C_{12}$-alkyl optionally substituted with halogen (such as perhaloalkyls), $C_2$-$C_{12}$-alkenyl optionally substituted with halogen, —$C_2$-$C_{12}$-alkynyl optionally substituted with halogen, —$NH_2$, protected amino, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-hetero aryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycl-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH-heteroaryl, —CONH-heterocycloalkyl, —$CO_2$—$C_1$-$C_{12}$-alkyl, —$CO_2$—$C_2$-$C_{12}$-alkenyl, —$CO_2$—$C_2$-$C_{12}$-alkynyl, —$CO_2$—$C_3$-$C_{12}$-cycloalkyl, —$CO_2$-aryl, —$CO_2$-heteroaryl, —$CO_2$-hetero cycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH-heteroaryl, —OCONH-heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_2$-$C_{12}$-cycloalkyl, —NHC(O)NH-aryl, —NHC(O)NH-heteroaryl, —NHC(O)NH-heterocycloalkyl, $NHC(S)NR_2$, NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S)NH-aryl, —$NHC(S)NR$-heteroaryl, —NHC(S)NH-heterocycloalkyl, —$NHC(NH)NH_2$, NHC(NH)NH—$C_1$-$C_{12}$-alkyl, —NHC(NH)NH—$C_2$-$C_{12}$-alkenyl, —NHC(NH)NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NR)NH—$C_1$-$C_{12}$-alkyl, —C(NH)NH—$C_2$-$C_{12}$— alkenyl, —C(NR)NH—$C_2$-$C_{12}$-alkynyl, —C(NH)NH—$C_3$-$C_{12}$-cycloalkyl, —C(NH)NH— aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -hetero arylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocyclo alkyl, or methylthiomethyl. It is understood that the aryls, heteroaryls, alkyls and the like can be further substituted.

The terms "$C_2$-$C_{12}$ alkenyl" or "$C_2$-$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, alkadienes and the like.

The term "substituted alkenyl," as used herein, refers to a "$C_2$-$C_{12}$ alkenyl" or "$C_2$-$C_6$ alkenyl" group as previously defined, substituted by one, two, three or more aliphatic substituents.

The terms "$C_2$-$C_{12}$ alkynyl" or "$C_2$-$C_6$ alkynyl," as used herein, denote a monovalent group derived from a hydrocarbon moiety containing from two to twelve or two to six carbon atoms having at least one carbon-carbon triple bond by the removal of a single hydrogen atom. Representative alkynyl groups include, but are not limited to, for example, ethynyl, 1-propynyl, 1-butynyl, and the like.

The term "substituted alkynyl," as used herein, refers to a "$C_2$-$C_{12}$ alkynyl" or "$C_2$-$C_6$ alkynyl" group as previously defined, substituted by one, two, three or more aliphatic substituents.

The term "$C_1$-$C_6$ alkoxy," as used herein, refers to a $C_1$-$C_6$ alkyl group, as previously defined, attached to the parent molecular moiety through an oxygen atom. Examples of $C_1$-$C_6$-alkoxy include, but are not limited to, methoxy, ethoxy, propoxy, isopropoxy, n-butoxy, sec-butoxy, tert-butoxy, n-pentoxy, neopentoxy and n-hexoxy.

The terms "halo" and "halogen," as used herein, refer to an atom selected from fluorine, chlorine, bromine and iodine.

The term "aryl," as used herein, refers to a mono- or bicyclic carbocyclic ring system having one or two aromatic rings including, but not limited to, phenyl, naphthyl, tetrahydronaphthyl, indanyl, idenyl and the like.

The term "substituted aryl," as used herein, refers to an aryl group, as previously defined, substituted by one, two, three or more aromatic substituents.

Aromatic substituents include, but are not limited to, —F, —Cl, —Br, —I, —OH, protected hydroxy, aliphatic ethers, aromatic ethers, oxo, —NO$_2$, —CN, —C$_1$-C$_{12}$-alkyl optionally substituted with halogen (such as perhaloalkyls), C$_2$-C$_{12}$-alkenyl optionally substituted with halogen, —C$_2$-C$_{12}$-alkynyl optionally substituted with halogen, —NH$_2$, protected amino, —NH—C$_1$-C$_{12}$-alkyl, —NH—C$_2$-C$_{12}$-alkenyl, —NH—C$_2$-C$_{12}$-alkenyl, —NH—C$_3$-C$_{12}$-cycloalkyl, —NH-aryl, —NH-heteroaryl, —NH-heterocycloalkyl, -dialkylamino, -diarylamino, -diheteroarylamino, —O—C$_1$-C$_{12}$-alkyl, —O—C$_2$-C$_{12}$-alkenyl, —O—C$_2$-C$_{12}$-alkynyl, —O—C$_3$-C$_{12}$-cycloalkyl, —O-aryl, —O-hetero aryl, —O-heterocycloalkyl, —C(O)—C$_1$-C$_{12}$-alkyl, —C(O)—C$_2$-C$_{12}$-alkenyl, —C(O)—C$_2$-C$_{12}$-alkynyl, —C(O)—C$_3$-C$_{12}$-cycloalkyl, —C(O)-aryl, —C(O)-heteroaryl, —C(O)-heterocycloalkyl, —CONH$_2$, —CONH—C$_1$-C$_{12}$-alkyl, —CONH—C$_2$-C$_{12}$-alkenyl, —CONH—C$_2$-C$_{12}$-alkynyl, —CONH—C$_3$-C$_{12}$-cycloalkyl, —CONH-aryl, —CONH-heteroaryl, —CONH-heterocycloalkyl, —CO$_2$—C$_1$-C$_{12}$-alkyl, —CO$_2$—C$_2$-C$_{12}$-alkenyl, —CO$_2$—C$_2$-C$_{12}$-alkynyl, —CO$_2$—C$_3$-C$_{12}$-cycloalkyl, —CO$_2$-aryl, —CO$_2$-heteroaryl, —CO$_2$-hetero cycloalkyl, —OCO$_2$—C$_1$-C$_{12}$-alkyl, —OCO$_2$—C$_2$-C$_{12}$-alkenyl, —OCO$_2$—C$_2$-C$_{12}$-alkynyl, —OCO$_2$—C$_3$-C$_2$-cycloallyl, —OCO$_2$-aryl, —OCO$_2$-heteroaryl, —OCO$_2$-heterocycloalkyl, —OCONH$_2$, —OCONH—C$_1$-C$_{12}$-alkyl, —OCONH C$_2$-C$_{12}$-alkenyl, —OCONH—C$_2$-C$_{12}$-alkynyl, —OCONH—C$_3$-C$_{12}$-cycloalkyl, —OCONH-aryl, —OCONH-heteroaryl, —OCONH-heterocycloalkyl, —NH C(O)—C$_1$-C$_{12}$-alkyl, —NHC(O)—C$_2$-C$_{12}$-alkenyl, —NHC(O)—C$_2$-C$_{12}$-alkynyl, —NHC(O)—C$_3$-C$_2$-cycloalkyl, —NHC(O)-aryl, —NHC(O)-heteroaryl, —NHC(O)-heterocycloalkyl, —NHCO$_2$—C$_1$-C$_{12}$-alkyl, —NHCO$_2$—C$_2$-C$_{12}$-alkenyl, —NHCO$_2$—C$_2$-C$_{12}$-alkynyl, —NHCO$_2$—C$_3$-C$_{12}$-cycloalkyl, —NHCO$_2$-aryl, —NHCO$_2$-heteroaryl, —NHCO$_2$-heterocycloalkyl, —NHC(O)NH$_2$, NHC(O)NH—C$_1$-C$_{12}$-alkyl, —NHC(O)NH—C$_2$-C$_{12}$-alkenyl, —NHC(O)NH—C$_2$-C$_{12}$-alkynyl, —NHC(O)NH—C$_3$-C$_{12}$-cycloalkyl, —NHC(O)NH-aryl, —NHC(O)NH-heteroaryl, —NHC(O)NH-heterocycloalkyl, NHC(S)NH$_2$, NHC(S)NH—C$_1$-C$_{12}$-alkyl, —NHC(S)NH—C$_2$-C$_{12}$-alkenyl, —NHC(S)NH—C$_2$-C$_{12}$-alkynyl, —NHC(S)NH—C$_3$-C$_{12}$-cycloalkyl, —NHC(S)NH-aryl, —NHC(S)NH-heteroaryl, —NHC(S)NH-heterocycloalkyl, —NHC(NH)NH$_2$, NHC(NH)NH—C$_1$-C$_{12}$-alkyl, —NHC(NH)NH—C$_2$-C$_{12}$-alkenyl, —NHC(NH)NH—C$_2$-C$_{12}$-alkynyl, —NHC(NH)NH—C$_3$-C$_{12}$-cycloalkyl, —NHC(NH)NH-aryl, —NHC(NH)NH-heteroaryl, —NHC(NH)NH-heterocycloalkyl, NHC(NH)—C$_1$-C$_{12}$-alkyl, —NHC(NH)—C$_2$-C$_{12}$-alkenyl, —NHC(NH)—C$_2$-C$_{12}$-alkynyl, —NHC(NH)—C$_3$-C$_{12}$-cycloalkyl, —NHC(NH)-aryl, —NHC(N$_H$)-heteroaryl, —NHC(N$_H$)-heterocycloalkyl, —C(NH)NH—C$_1$-C$_{12}$-alkyl, —C(NH)NH—C$_2$-C$_{12}$-alkenyl, —C(NH)NH—C$_2$-C$_{12}$-alkynyl, —C(NH)NH—C$_3$-C$_{12}$-cycloalkyl, —C(NH)NH-aryl, —C(NH)NH-heteroaryl, —C(NH)NH-heterocycloalkyl, —S(O)—C$_1$-C$_{12}$-alkyl, —S(O)—C$_2$-C$_{12}$-alkenyl, —S(O)—C$_2$-C$_{12}$-alkynyl, —S(O)—C$_3$-C$_{12}$-cycloalkyl, —S(O)-aryl, —S(O)-heteroaryl, —S(O)-heterocycloalkyl-SO$_2$NH$_2$, —SO$_2$NH—C$_2$-C$_{12}$-alkyl, —SO$_2$NH—C$_2$-C$_{12}$-alkenyl, —SO$_2$NH—C$_2$-C$_{12}$-alkynyl, —SO$_2$NH—C$_3$-C$_{12}$-cycloalkyl, —SO$_2$NH-aryl, —SO$_2$NH-heteroaryl, —SO$_2$NH-heterocycloalkyl, —NHSO$_2$—C$_1$-C$_{12}$-alkyl, —NHSO$_2$—C$_2$-C$_{12}$-alkenyl, —NHSO$_2$—C$_2$-C$_{12}$-alkynyl, —NHSO$_2$—C$_3$-C$_{12}$-cycloalkyl, —NHSO$_2$-aryl, —NHSO$_2$-heteroaryl, —NHSO$_2$-heterocycloalkyl, —CH$_2$NH$_2$, —CH$_2$SO$_2$ CH$_3$, -aryl, -arylalkyl, -heteroaryl, -hetero arylalkyl, -heterocycloalkyl, —C$_3$-C$_{12}$-cycloalkyl, polyalkoxyalkyl, polyalkoxy, -methoxymethoxy, -methoxyethoxy, —SH, —S—C$_1$-C$_{12\text{-}alkyl}$, —S—C$_2$-C$_{12}$-alkenyl, —S—C$_2$-C$_{12}$-alkynyl, —S—C$_3$-C$_{12}$-cycloalkyl, —S-aryl, —S-heteroaryl, —S-heterocycloalkyl, or methylthiomethyl. It is understood that the aryls, heteroaryls, alkyls and the like can be further substituted.

The term "arylalkyl," as used herein, refers to an aryl group attached to the parent compound via a $C_1$-$C_3$ alkyl or $C_1$-$C_6$ alkyl residue. Examples include, but are not limited to, benzyl, phenethyl and the like.

The term "substituted arylalkyl," as used herein, refers to an arylalkyl group, as previously defined, substituted by one, two, three or more aromatic substituents.

The term "heteroaryl," as used herein, refers to a mono-, bi-, or tri-cyclic aromatic radical or ring having from five to ten ring atoms of which at least one ring atom is selected from S, O and N; zero, one or two ring atoms are additional heteroatoms independently selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The heteroaromatic ring may be bonded to the chemical structure through a carbon or hetero atom.

The term "substituted heteroaryl," as used herein, refers to a heteroaryl group as previously defined, substituted by one, two, three or four aromatic substituents.

The term "$C_3$-$C_{12}$-cycloalkyl," as used herein, denotes a monovalent group derived from a monocyclic or bicyclic saturated carbocyclic ring compound by the removal of a single hydrogen atom. Examples include, but not limited to, cyclopropyl, cyclobutyl, cyclopentyl, cyclohexyl, bicyclo [2.2.1]heptyl, and bicyclo[2.2.2]octyl.

The term "substituted $C_3$-$C_{12}$-cycloalkyl," as used herein, refers to a $C_3$-$C_{12}$-cycloalkyl group as previously defined, substituted by one, two, three or more aliphatic substituents.

The term "heterocycloalkyl," as used herein, refers to a non-aromatic 5-, 6- or 7-membered ring or a bi- or tri-cyclic group fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, (iv) the nitrogen heteroatom may optionally be quaternized, (iv) any of the above rings may be fused to a benzene ring, and (v) the remaining ring atoms are carbon atoms which may be optionally oxo-substituted. Representative heterocycloalkyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl.

The term "substituted heterocycloalkyl," as used herein, refers to a heterocycloalkyl group, as previously defined, substituted by one, two, three or more aliphatic substituents. The term "heteroarylalkyl," as used herein, to an heteroaryl group attached to the parent compound via a $C_1$-$C_3$ alkyl or $C_1$-$C_6$ alkyl residue. Examples include, but are not limited to, pyridinylmethyl, pyrimidinylethyl and the like.

The term "substituted heteroarylalkyl," as used herein, refers to a heteroarylalkyl group, as previously defined, substituted by independent replacement of one, two, or three or more aromatic substituents.

The term "$C_1$-$C_3$-alkylamino," as used herein, refers to one or two $C_1$-$C_3$-alkyl groups, as previously defined, attached to the parent molecular moiety through a nitrogen atom. Examples of $C_1$-$C_3$-alkylamino include, but are not limited to, methylamino, dimethylamino, ethylamino, diethylamino, and propylamino.

The term "alkylamino" refers to a group having the structure —NH($C_1$-$C_{12}$ alkyl) where $C_1$-$C_{12}$ alkyl is as previously defined.

The term "dialkylamino" refers to a group having the structure —N($C_1$-$C_{12}$ alkyl) ($C_1$-$C_{12}$ alkyl), where $C_1$-$C_{12}$ alkyl is as previously defined. Examples of dialkylamino are, but not limited to, dimethylamino, diethylamino, methylethylamino, piperidino, and the like.

The term "alkoxycarbonyl" represents an ester group, i.e., an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$-$C_{12}$ alkyl) or —C(O)N($C_1$-$C_{12}$ alkyl) ($C_1$-$C_{12}$alkyl), —C(O)NH$_2$, NHC(O)($C_1$-$C_{12}$ alkyl), N($C_1$-$C_{12}$alkyl)C(O)($C_1$-$C_{12}$ alkyl) and the like.

The term "hydroxy protecting group" as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, 1,1-dimethyl-2-propenyl, 3-methyl-3-butenyl, allyl, benzyl, para-methoxybenzyldiphenylmethyl, triphenylmethyl (trityl), tetrahydrofuryl, methoxymethyl, methylthiomethyl, benzyloxymethyl, 2,2,2-triehloroethoxymethyl, 2-(trimethylsilyl)ethoxymethyl, methanesulfonyl, para-toluenesulfonyl, trimethylsilyl, triethylsilyl, triisopropylsilyl, and the like. Preferred hydroxyl protecting groups for the present invention are acetyl (Ac or —C(O)CH$_3$), benzoyl (Bn or —C(O)$C_6H_5$), and trimethylsilyl (TMS or —Si(CH$_3$)$_3$).

The term "protected hydroxy", as used herein, refers to a hydroxy group protected with a hydroxy protecting group, as defined above, including benzoyl, acetyl, trimethylsilyl, triethylsilyl, methoxymethyl groups, for example.

The term "amino protecting group", as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "protected amino", as used herein, refers to an amino group protected with an amino protecting group as defined above.

The term "acyl" includes residues derived from acids, including but not limited to carboxylic acids, carbamic acids, carbonic acids, sulfonic acids, and phosphorous acids. Examples include aliphatic carbonyls, aromatic carbonyls, aliphatic sulfonyls, aromatic sulfinyls, aliphatic sulfinyls, aromatic sulfonyls, aliphatic sulfamyls, aromatic sulfamyls, aromatic phosphates and aliphatic phosphates.

An "amino acid" is a molecule that contains both amine and carboxyl functional groups with the general formula NH2CHRCOOH. The term amino acid includes standard amino acids and nonstandard amino acids.

"Standard amino acids" are alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

A "standard amino acid which is not aspartic acid" is selected from the group consisting of alanine, arginine, asparagine, cysteine, glutamic acid, glutamine, glycine, histidine, isoleucine, leucine, lysine, methionine, phenylalanine, proline, serine, threonine, tryptophan, tyrosine, and valine. In the case of glutamine or glutamic acid, a "derivative thereof" is e.g. a nitrile or an ester, such as e.g. glutamine-nitrile, glutamic acid ester.

"Nonstandard amino acids" are amino acids (molecules that contains both amine and carboxyl functional groups) which are not one of the standard amino acids. Examples thereof are selenocysteine (incorporated into some proteins at a UGA codon), pyrrolysine (used by some methanogenic bacteria in enzymes to produce methane and coded for with the codon UAG), lanthionine, 2-aminoisobutyric acid, dehydroalanine, 3-amino-6-hydroxy-2-piperidone, gamma-aminobutyric acid, ornithine, citrulline, homocysteine, dopamine or hydroxyproline.

"Non-basic standard amino acids" are alanine, asparagine, aspartic acid, cysteine, glutamic acid, glutamine, glycine, isoleucine, leucine, methionine, phenylalanine, proline, serine, threonine, tryptophan, tyrosine, and valine.

"Ahp" (3-amino-6-hydroxy-piperidin-2-one) is a non-standard amino acid found for instance in cyanobacteria. "Ahp derivatives" include, but are not limited to 3-amino-3,4-dihydro-1H-pyridin-2-one (dehydro-AHP), 3-amino-piperidin-2-one and "ether and ester derivatives of AHP. Preferred Ahp derivatives are 3-amino-piperidin-2-one, or Ahp-I or Ahp-II as depicted below wherein R is selected from the group consisting of $(C_{1-12})$alkyl, $(C_{2-12})$alkenyl, $(C_{2-12})$alkynyl halo$(C_{1-12})$alkyl, $(C_{1-12})$alkoxy$(C_{1-12})$alkyl, $(C_{1-12})$alkoxy$(C_{1-12})$alkoxy$(C_{1-12})$alkyl, hydroxy$(C_{1-12})$alkyl, phenyl and phenyl$(C_{1-6})$alkyl.

Different members of this family of nonstandard amino acids are:

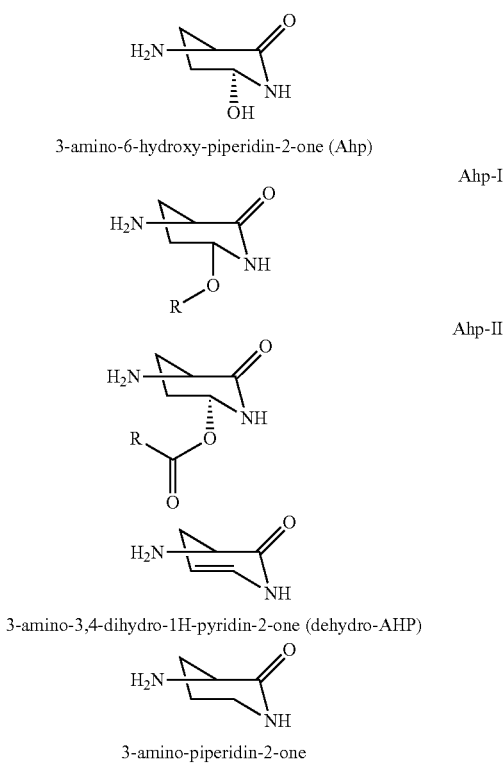

Proline derivative includes e.g. 5-hydroxyprolin.

"Amino acid derivatives" include, but are not limited to, O-alkyl, O-aryl, O-acyl, S-alkyl, S-aryl, S—S-alkyl, alkoxycarbonyl, O-carbonyl-alkoxy, carbonate, O-carbonyl-aryloxy, O-carbonyl-alkylamino, O-carbonyl-arylamino, N-alkyl, N-dialkyl, N-trialkylammonium, N-acyl, N-carbonyl-alkoxy, N-carbonyl-aryloxy, N-carbonyl-alkylamino, N-carbonyl-arylamino, N-sulfonylalkyl, or N-sulfonylaryl.

"Non-basic standard amino acid derivatives" include, but are not limited to, O-alkyl, O-aryl, O-acyl, S-alkyl, S-aryl, S—S-alkyl, alkoxycarbonyl, O-carbonyl-alkoxy, carbonate, O-carbonyl-aryloxy, O-carbonyl-alkylamino, O-carbonyl-arylamino, N-alkyl, N-dialkyl, N-trialkylammonium, N-acyl, N-carbonyl-alkoxy, N-carbonyl-aryloxy, N-carbonyl-alkylamino, N-carbonyl-arylamino, N-sulfonylalkyl, or N-sulfonylaryl.

"Tyrosine derivative" include, but are not limited to, —O-alkyl, O-aryl, O-heteroaryl, O-acyl, O—$PO_3H$ and O—$SO_3H$, as well as halogenation, in ortho or meta position.

The OH group of the tyrosine may be OR, wherein R is selected from the group consisting of
hydrogen, $(C_{1-12})$alkyl, $(C_{2-12})$alkenyl, $(C_{2-12})$alkynyl, halo$(C_{1-12})$alkyl,
halo$(C_{2-12})$alkenyl, halo$(C_{2-12})$alkynyl, $(C_{1-12})$alkoxycarbonyl,
$(C_{1-12})$alkoxycarbonyl$(C_{1-12})$alkyl,
$(C_{1-12})$alkylaminocarbonyl, unsubstituted or further substituted by aryl, arylalkyl, arylalkenyl or arylalkynyl, heterocyclyl and heterocyclylalkyl.

"Depsipeptide derivative" include but are not limited to, depsipeptides modified as described herein and to those specifically described in the examples below. Said derivatives can be prepared using methods well known in the art.

The invention further relates to pharmaceutically acceptable salts and derivatives of the compounds of the present invention and to methods for obtaining such compounds. One method of obtaining the compound is by cultivating a Chondromyces strain of the invention, or a mutant or a variant thereof, under suitable conditions, preferably using the fermentation protocol described herein-below.

"Salts" of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g., by treating the compounds with an acid or a suitable anion exchange reagent. Internal salts of compounds of the present invention containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g., using chromatographic methods, distribution methods, (re-) crystallization, and the like.

The cyclic depsipeptides of the invention can inhibit of chymotrypsin-like proteases. Examples of chymotrypsin-like proteases are elastases and kallikrein 7. In particular, the cyclic depsipeptides of the invention are excellent inhibitors of kallikrein 7.

An "inhibitor" is a cyclic depsipeptide that inhibits an enzymatic reaction with a measure $IC_{50}$ of less than 100 µM, for instance 50 µM, 30 µM, 20 µM or 10 µM. Particularly preferred are cyclic depsipeptides with an $IC_{50}$ of less than 30 µM for human kallikrein 7, for instance cyclic depsipeptides with an $IC_{50}$ of less than 10 µM, 1 µM, 100 nM, 50 nM, 40 nM, 30 nM, 20 nM, 10 nM, or less. E.g. compounds of examples 5, 19 and 33 show IC50 values of 0.009 µM, 0.007 µM, 0.005 µM, respectively. $IC_{50}$ for human kallikrein can be measured using the fluorescence-quenched substrate Ac-Glu-Asp (EDANS)-Lys-Pro-Ale-Leu-Phe^Arg-Leu-Gly-Lys(DAB-CYL)-Glu-NH$_2$ (where ^ indicates the scissile bond, identified by MS analysis) which can be purchased from Biosyntan (Berlin, Germany). Enzymatic reactions are conducted in 50 mM sodium citrate buffer at pH 5.6 containing 150 mM NaCl and 0.05% (w/v) CHAPS. For the determination of $IC_{50}$ values the assay is performed at room temperature in 384-well plates. All final assay volumes are 30 µl. Test compounds are dissolved in 90% (v/v) DMSO/water and diluted in water (containing 0.05% (w/v) CHAPS) to 3-times the desired assay concentration. The 11 final compound concentrations are: 0.3 nM, 1 nM, 3 nM, 10 nM, 30 nM, 100 nM, 300 nM, 1 µM, 3 µM, 10 µM and 30 µM. For each assay, 10 µl water/CHAPS (±test compound) are added per well, followed by 10 µl protease solution (diluted with 1.5× assay buffer). The protease concentration in final assay solution is 0.2 nM (according to the enzyme concentrations determined by the Bradford method). After 1 hour of incubation at room temperature, the reaction is started by addition of 10 µl substrate solution (substrate dissolved in 1.5× assay buffer, final concentration is 2 µM). The effect of the compound on the enzymatic activity is obtained from the linear progress curves and determined from two readings, the first one taken directly after the addition of substrate (t=0 min) and the second one after 1 hour (t=60 min). The $IC_{50}$ value is calculated from the plot of percentage of inhibition vs. inhibitor concentration using non-linear regression analysis software (XLfit, Vers. 4.0; ID Business Solution Ltd., Guildford, Surrey, UK).

"Diseases" and "disorders" which may hence be treated or prevented using the cyclic depsipeptides, are diseases known to be related with chymotrypsin-like proteases. More preferred are diseases known to be related to elastases or kallikrein 7 activity. Equally preferred are diseases known to be related to human neutrophil elastase. Diseases and disorders which may hence be treated or prevented using the cyclic depsipeptides of the invention include pain, acute inflammation, chronic inflammation, arthritis, inflamed joints, bursitis, osteoarthritis, rheumatoid arthritis, juvenile rheumatoid arthritis, septic arthritis, fibromyalgia, systemic lupus erythematosus, phlebitis, tendinitis, rash, psoriasis, acne, eczema, facial seborrheic eczema, eczema of the hands, face or neck, foreskin infections, athlete's foot, fistulae infections, infected topical ulcers, navel infections in newborns, wrinkles, scars, kelloids, boils, warts and allergic itch, hemorrhoids, wounds, wound infections, wounds from burns, a fungal infection and an immunogical disorder including an autoimmune disease. Preferred diseases which may be treated or prevented using the cyclic depsipeptides of the invention include chronic obstructive pulmonary disease (including pulmonary emphysema and chronic bronchitis), chronic and acute interstitial pneumonia, idiopathic interstitial pneumonia (IIP), diffuse panbronchiolitis, cystic lung fibrosis, acute lung injury (ALI)/acute respiratory distress syndrome (ARDS), bronchiectasis, asthma, pancreatitis, nephritis, hepatitis (hepatic failure), chronic rheumatoid arthritis, arthrosclerosis, osteroarthritis, psoriasis, periodontal disease, atherosclerosis, organ transplant rejection, tissue injury caused by ischemic/reperfusion, shock, septicemia, blood coagulopathy including disseminated intravascular coagulation (DIC) and deep vein-thrombosis, conjunctivitis, keratitis, corneal ulcer, Crohn's disease, systemic lupus erythematosus. More preferred diseases and disorders which may be treated or prevented using the cyclic depsipeptides of the invention are "epithelial dysfunction" or "epithelial disease" including, but are not limited to, inflammatory and/or hyperpoliferative and pruritic skin diseases such as keloids, hypertrophic scars, acne, atopic dermatitis, psoriasis, Netherton's syndrome or other pruritic dermatoses such as prurigo nodularis, unspecified itch of the elderly as well as other diseases with epithelial barrier dysfunction such as inflammatory bowel disease and Crohn's disease, cystic fibrosis (CF), chronic obstructive pulmonary disease (COPD), pulmonary fibrosis, adult respiratory distress syndrome, chronic bronchitis, hereditary emphysema, rheumatoid arthritis, IBD, psoriasis, asthma. In another preferred embodiment, the cyclic depsipeptides of the invention can be use to treat cancer, in particular ovarian cancer.

Diseases and disorders which may hence be preferably treated or prevented using the cyclic depsipeptides of the invention include inflammatory and/or hyperpoliferative and pruritic skin diseases such as keloids, hypertrophic scars, acne, atopic dermatitis, psoriasis, pustular psioriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer, cystic fibrosis (CF), chronic obstructive pulmonary disease (COPD), pulmonary fibrosis, adult respiratory distress syndrome, chronic bronchitis, hereditary emphysema, rheumatoid arthritis, IBD, psoriasis, and asthma.

Diseases and disorders which may hence be more preferably treated or prevented using the cyclic depsipeptides of the invention include keloids, hypertrophic scars, acne, atopic dermatitis, psoriasis, pustular psioriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer.

Diseases and disorders which may hence be equally preferably treated or prevented using the cyclic depsipeptides of the invention include cystic fibrosis (CF), chronic obstructive pulmonary disease (COPD), pulmonary fibrosis, adult respiratory distress syndrome, chronic bronchitis, hereditary emphysema, rheumatoid arthritis, IBD, psoriasis, asthma.

Diseases and disorders which may be even more preferably treated or prevented using the cyclic depsipeptides of the invention include keloids, hypertrophic scars, acne, atopic dermatitis, psoriasis, pustular psioriasis, rosacea, Netherton's syndrome or other pruritic dermatoses such as prurigo nodularis, unspecified itch of the elderly, as well as other diseases with epithelial barrier dysfunction such as aged skin.

Human kallikrein 7 (hK7) is an enzyme with serine protease activity located in the human skin. It was first described as stratum corneum chymotryptic enzyme (SCCE) and may play a role in desquamation of stratum corneum by cleaving proteins of the stratum corneum (e.g., corneodesmosin and plakoglobin). The stratum corneum is the barrier-forming outermost layer of the epidermis and consists of cornified epithelial cells surrounded by highly organized lipids. It is continuously being formed by epidermal differentiation and in normal epidermis the constant thickness of the stratum corneum is maintained by a balance between the proliferation of the keratinocytes and desquamation. Enhanced expression of SCCE in inflammatory skin disease may be of etiological significance (Hansson, et al. (2002)). Transgenic mice expressing human kallikrein 7 in epidermal keratinocytes were found to develop pathologic skin changes with increased epidermal thickness, hyperkeratosis, dermal inflammation, and severe pruritis. A genetic association between a 4 bp (AACC) insertion in the 3'UTR of the stratum corneum chymotryptic enzyme gene and atopic dermatitis has been reported (Vasilopoulos, et al. (2004)), suggesting that the enzyme could have an important role in the development of atopic dermatitis. Atopic dermatitis is a disease with an impaired skin barrier that affects 15%-20% of children.

Kallikrein 7 is a S1 serine protease of the kallikrein gene family displaying a chymotrypsin like activity. Human kallikrein 7 (hK7, KLK7 or stratum corneum chymotryptic enzyme (SCCE), Swissprot P49862) plays an important role in skin physiology (1, 2, 3). It is mainly expressed in the skin and has been reported to play an important role in skin physiology. hK7 is involved in the degradation of the intercellular cohesive structures in cornified squamous epithelia in the process of desquamation. The desquamation process is well regulated and delicately balanced with the de 120170 production of corneocytes to maintain a constant thickness of the stratum corneum, the outermost layer of the skin critically involved in skin barrier function. In this regard, hK7 is reported to be able to cleave the corneodesmosomal proteins corneodesmosin and desmocollin 1 (4, 5, 6). The degradation of both corneodesmosomes is required for desquamation. In addition, very recently it has been shown that the two lipid processing enzymes β-glucocerebrosidase and acidic sphingomyelinase can be degraded by hK7 (7). Both lipid processing enzymes are co-secreted with their substrates glucosylceramides and sphingomyelin and process these polar lipid precursors into their more non-polar products e.g. ceramides, which are subsequently incorporated into the extracellular lamellar membranes. The lamellar membrane architecture is critical for a functional skin barrier. Finally, hK7 has been shown to activate Interleukin-1β (IL-1β) precursor to its active form in vitro (8). Since keratinocytes express IL-1β but not the active form of the specific IL-1β converting enzyme (ICE or caspase 1), it is proposed that IL-1β activation in human epidermis occurs via another protease, a potential candidate being hK7.

Recent studies link an increased activity of hK7 to inflammatory skin diseases like atopic dermatitis, psoriasis or Netherton's syndrome. This might lead to an uncontrolled degradation of corneodesmosomes resulting in a miss-regulated desquamation, an enhanced degradation of lipid processing enzymes resulting in a disturbed lamellar membrane architecture or an uncontrolled activation of the proinflammatory cytokine IL-1β. The net result would be an impaired skin barrier function and inflammation (see also WO-A-20041108139).

Due to the fact that the hK7 activity is controlled at several levels, various factors might be responsible for an increased hK7 activity in inflammatory skin diseases. Firstly, the amount of protease being expressed might be influenced by genetic factors. Such a genetic link, a polymorphism in the 3'-UTR in the hK7 gene, was recently described (9). The authors hypothesise that the described 4 base pair insertion in the 3'-UTR of the kallikrein 7 gene stabilizes the hK7 mRNA and results in an overexpression of hK7. Secondly, since hK7 is secreted via lamellar bodies to the stratum corneum extracellular space as zymogen and it is not able to autoactivate, it needs to be activated by another protease e.g. hK5 (5). Uncontrolled activity of such an activating enzyme might result in an overactivation of hK7. Thirdly, activated hK7 can be inhibited by natural inhibitors like LEKTI, ALP or elafin (10, 11). The decreased expression or the lack of such inhibitors might result in an enhanced activity of hK7. Recently it was found, that mutations in the spink5 gene, coding for LEKTI, are causative for Netherton's syndrome (12) and a single point mutation in the gene is linked to atopic dermatitis (13, 14). Finally, another level of controlling the activity of hK7 is the pH. hK7 has a neutral to slightly alkaline pH optimum (2) and there is a pH gradient from neutral to acidic from the innermost to the outermost layers in the skin. Environmental factors like soap might result in a pH increase in the outermost layers of the stratum corneum towards the pH optimum of hK7 thereby increasing the hK7 activity.

An increased activity of hK7 is linked to skin diseases with an impaired skin barrier including inflammatory and hyperpoliferative skin diseases. Firstly, Netherton's syndrome patients show a phenotype dependent increase in serine protease activity, a decrease in corneodesmosomes, a decrease in the lipid processing enzymes β-glucocerebrosidase and acidic sphingomyelinase, and an impaired barrier function (15, 16). Secondly, a transgenic mice overexpressing human kallikrein 7 shows a skin phenotype similar to that found in patients with atopic dermatitis (17, 18, 19). Thirdly, in the skin of atopic dermatitis and psoriasis patients elevated levels of hK7 were described (17, 20). Furthermore, increased activity of K7 and thus epithelial barrier dysfunction may also play an important role in the pathology of other epithelial diseases such as inflammatory bowel disease and Crohn's disease.

Therefore, hK7 is considered to be a potential target for the treatment of diseases involved with epithelial dysfunction such as inflammatory and/or hyperpoliferative and pruritic skin diseases such as keloids, hypertrophic scars, acne, atopic dermatitis, psoriasis, pustular psioriasis, rosacea, Netherton's syndrome or other pruritic dermatoses such as prurigo nodularis, unspecified itch of the elderly as well as other diseases with epithelial barrier dysfunction such as aged skin, inflammatory bowel disease and Crohn's disease, as well as pancreatitis, or of cancer, in particular ovarian cancer, and there is a need for specific modulators (agonists or inhibitors) thereof.

Human neutrophil elastase (FINE, also know as human leukocyte elastase, FILE) belongs to the chymotrypsin family of serine proteinases. Its catalytic activity is optimal around pH 7, and the catalytic site is composed of three hydrogen-bonded amino acid residues: His57, Asp102, and Ser195 (in chymotrypsin numbering), which form the so-called catalytic triad. The enzyme is composed of a single peptide chain of 218 amino acid residues and four disulfide bridges. It shows 30 to 40% sequence identity with other elastinolytic or non-elastinolytic serine proteinases. FINE preferentially cleaves the oxidized insulin B chain with Val at the P1 position, but it also hydrolyzes bonds with Ala, Ser, or Cys in the P1 position.

HNE is located in the azurophilic granules of polymorphonuclear leukocytes (PMNLs), where the HNE concentration is rather high (3 μg of enzyme/$10_6$ cells). The major physiological function is to digest bacteria and immune complexes and to take part in the host defense process. HNE aids in the migration of neutrophils from blood to various tissues such as the airways in response to chemotactic factors. HNE also takes part in wound healing, tissue repair, and in the apoptosis of PMNLs.

In addition to elastin (highly flexible and highly hydrophobic component of lung connective tissue, arteries, skin, and ligaments), HNE cleaves many proteins with important biological functions, including different types of collagens, membrane proteins, and cartilage proteoglycans. HNE also indirectly favours the breakdown of extracellular matrix proteins by activating procollagenase, prostromelysin, and progelatinase. HNE inactivates a number of endogenous proteinase inhibitors such as $\alpha_2$-antiplasmin, $\alpha_1$-antichymotrypsin, antithrombin, and tissue inhibitor of metalloproteinases.

Extracellular elastase activity is tightly controlled in the pulmonary system by $\alpha 1$-protease inhibitor ($\alpha_1$PI), responsible for protection of the lower airways from elastolytic damage, whereas the secretory leukocyte proteinase inhibitor protects mainly the upper airways. In a number of pulmonary pathophysiological states, e.g., pulmonary emphysema, chronic bronchitis, and cystic fibrosis, endogenous elastase inhibitors are inefficient in regulating HNE activity.

HNE is considered to be the primary source of tissue damage associated with inflammatory diseases such as pulmonary emphysema, adult respiratory distress syndrome (ARDS), chronic bronchitis, chronic obstructive pulmonary disease (COPD), pulmonary hypertension, and other inflammatory diseases as well as bronchopulmonary dysplasia in premature neonates. HNE is involved in the pathogenesis of increased and abnormal airway secretions commonly associated with airway inflammatory diseases. Thus, bronchoalveolar lavage (BAL) fluid from patients with chronic bronchitis and cystic fibrosis has increased HNE activity. Furthermore, excessive elastase has been proposed to contribute not only to these chronic inflammatory diseases but also to acute inflammatory diseases such as ARDS and septic shock.

Therefore, HNE is considered to be a potential target for the treatment of diseases involved with HNE activity such as inflammatory diseases such as pulmonary emphysema, adult respiratory distress syndrome (ARDS), chronic bronchitis, chronic obstructive pulmonary disease (COPD), pulmonary hypertension, and other inflammatory diseases as well as bronchopulmonary dysplasia in premature neonates, and diseases involved with increased and abnormal airway secretions as well as acute inflammatory diseases. Thus there is a need for specific modulators (agonists or inhibitors) if HNE.

Treatment can be by local or systemic application such a creams, ointments and suppositories or by oral or se or iv application or by inhalation, respectively, in a manner well known in the art.

In one aspect the depsipeptides according to the invention are obtained by cultivating a *Chondromyces crocatus* strain which was deposited on 24 Apr. 2007 with the DSMZ (DSM 19329) or are obtained by cultivating a *Chondromyces robustus* strain which was deposited on 24 Apr. 2007 with the DSMZ (DSM 19330) or are obtained by cultivating a *Chondromyces apiculatus* strain which was deposited on 23 Jun. 2008 with the DSMZ (DSM 21595).

The deposit of the strains was made under the terms of the Budapest Treaty on the International Recognition of the Deposit of Microorganisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement.

It is to be understood that the present invention is not limited to cultivation of the particular strains *Chondromyces crocatus* and *Chondromyces robustus* and *Chondromyces apiculatus*. Rather, the present invention contemplates the cultivation of other organisms capable of producing depsipeptides, such as mutants or variants of the strains that can be derived from this organism by known means such as X-ray irradiation, ultraviolet irradiation, treatment with chemical mutagens, phage exposure, antibiotic selection and the like.

The depsipeptides of the present invention may be biosynthesized by various microorganisms. Microorganisms that may synthesize the compounds of the present invention include but are not limited to bacteria of the order Myxococcales, also referred to as myxobacteria. Non-limiting examples of members belonging to the genera of myxobacteria include *Chondromyces, Sorangium, Polyangium, Byssophaga, Haploangium, Jahnia, Nannocystis, Koffleria, Myxococcus, Corallococcus, Cystobacter, Archangium, Stigmatella, Hyalangium, Melittangium, Pyxicoccus*. The taxonomy of myxobacteria is complex and reference is made to Garrity G M, Bell J Y, Lilburn TG (2004) Taxonomic outline of the prokaryotes, Bergey's manual of systematic bacteriology, $2^{nd}$ edition, release 5.0 May 2004. (http://141.150.157.80/bergeysoutline/main.htm).

The compounds of structural formulas (I-XVII) are produced by the aerobic fermentation of a suitable medium under controlled conditions via inoculation with a culture of *Chondromyces crocatus* or *Chondromyces robustus* or *Chondromyces apiculatus*. The suitable medium is preferably aqueous and contains sources of assimilable carbon, nitrogen, and inorganic salts.

Suitable media include, without limitation, the growth media mentioned below in examples 1 and 2. The fermentation is conducted for about 3 to about 20 days at temperatures ranging from about 10° C. to about 40° C.; however for optimum results it is preferred to conduct the fermentation at about 30° C. The pH of the nutrient medium during the fermentation can be about 6.0 to about 9.0. The culture media inoculated with the depsipeptides producing microorganisms may be incubated under aerobic conditions using, for example, a rotary shaker or a stifled tank fermentor Aeration may be achieved by the injection of air, oxygen or an appropriate gaseous mixture to the inoculated culture media during incubation. As soon as a sufficient amount of the depsipeptide compounds have accumulated, they may be concentrated and isolated from the culture in conventional and usual manner, for example by extraction- and chromatographic methods, precipitation or crystallization, and/or in a manner disclosed herein. As an example for extraction, the culture can be mixed and stirred with a suitable organic solvent such as n-butanol, ethyl acetate, cyclohexane, n-hexane, toluene, n-butyl acetate or 4-methyl-2-pentanone, the depsipeptide compounds in the organic layer can be recovered by removal of the solvent under reduced pressure. The resulting residue can optionally be reconstituted with for example water, ethanol, methanol or a mixture thereof, and re-extracted with a suitable organic solvent such as hexane, carbon tetrachloride, dichloromethane or a mixture thereof. Following removal of the solvent, the compounds may be further purified for example by chromatographic methods. As an example for chromatography, stationary phases such as silica gel or aluminia oxide can be applied, with organic eluting solvents or mixtures thereof, including ethers, ketones, esters, halogenated hydrocarbons or alcohols, or reversed-phase chromatography on modified silica gel having various functional groups and eluting with organic solvents or aqueous mixtures thereof, like acetonitrile, methanol or tetrahydrofuran at different pH. Another example is partition-chromatography, for example in the solid-liquid or in the liquid-liquid mode. Also size exclusion chromatography may be applied, for example using Sephadex LH-20 (Sigma-Aldrich) and eluting with different solvents, preferably with alcohols.

As it is usual in this field, the production as well as the recovery and purification process may be monitored by a variety of analytical methods, including bioassays, TLC, HPLC or a combination thereof, and applying different detection methods, for TLC typically UV light, iodine vapour or spraying colouring reagents, for HPLC typically UV light, mass sensitive or light scattering methods. For example a HPLC technique is represented by using a reversed-phase column with a functionalized silica gel and applying an eluent which is a linear gradient mixture of a polar water miscible solvent and water at a specific pH, and a detection method with UV light at different wavelengths and a mass sensitive detector.

The depsipetides biosynthesized by microorganisms may optionally be subjected to random and/or directed chemical modifications to form compounds that are derivatives or structural analogs. Such derivatives or structural analogs having similar functional activities are within the scope of the present invention. Depsipeptides may optionally be modified using methods well-known in the art and described herein.

For instance, derivatives of the depsipeptides of the invention may be prepared by derivatization of cyclic depsipeptides of formula

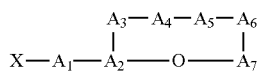

which comprises
a)—the preparation of compounds wherein A4 is

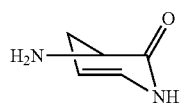

by treatment of a compound wherein A4 is

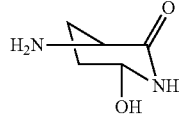

with an organic or inorganic acid, e.g. trifluoro acetic acid, sulphuric acid, hydrochloric acid, or a Lewis acid, e.g. borontrifluoride etherate in a solvent, e.g. dichloromethane, THF, or without a solvent at a temperature between −78° C. and 150° C., preferentially between −30° C. and room temperature.
b)—the preparation of compounds wherein A4 is

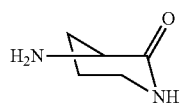

by treatment of a compound wherein A4 is

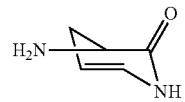

with molecular hydrogen or source thereof, e.g. cyclohexene, ammonium formate, in presence of a catalyst e.g. palladium in a solvent e.g. 2-propanol at a temperature between −50 and 100° C., preferentially at room temperature.

c)—the preparation of compounds wherein A4 is

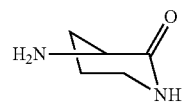

by treatment of a compound wherein A4 is

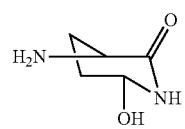

with an organic or inorganic acid, e.g. sulphuric acid, hydrochloric acid or a Lewis acid, e.g. borontrifluoride etherate in presence of an reducing agent, e.g. triethylsilane, a solvent, e.g. dichloromethane, THF, or without a solvent at a temperature between −78° C. and 150° C., preferentially between −50° C. and room temperature.

d)—the preparation of compounds wherein A4 is

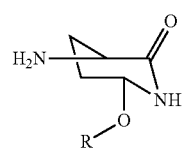

by treatment of a compound wherein A4 is

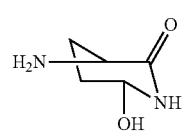

with an substituted or unsubstituted alkanol and an organic or inorganic acid, e.g. trifluoroacetic acid, sulphuric acid, hydrochloric acid, or a Lewis acid, e.g. metal salts in a solvent, e.g. substituted and unsubstituted alkanoles, THF, dichloromethane, preferentially substituted and unsubstituted alkanoles, or without a solvent at a temperature between −78° C. and 150° C., preferentially between −30° C. and 50° C.

e)—the preparation of compounds wherein A1 is

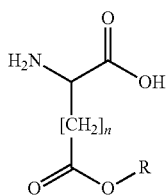

wherein n=1,2 and A4 is

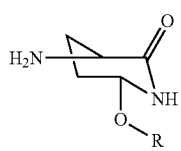

wherein R preferably is H, alkyl, substituted alkyl, by treatment of a compound wherein A1 is Gln or Asn and A4 is

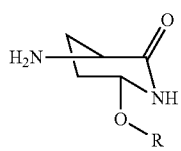

wherein R preferably is H, alkyl, substituted alkyl, with an substituted or unsubstituted alkanol and an organic or inorganic acid, e.g. trifluoroacetic acid, sulphuric acid, hydrochloric acid, or a Lewis acid, e.g. borontrifluoride etherate in a solvent, e.g. substituted and unsubstituted alkanols, THF, dichloromethane, preferentially substituted and unsubstituted alkanols, or without a solvent at a temperature between −78° C. and 150° C., preferentially between −30° C. and room temperature.

f)—the preparation of compounds wherein A1 is

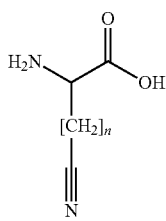

wherein n=1,2 and A4 is

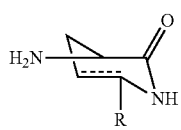

wherein R preferentially is H, OH, O-alkyl, substituted O-alkyl, O-acyl, by treatment of a compound wherein A1 is Gln or Asn and A4 is

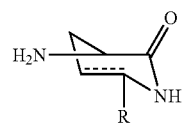

with an dehydrating agent e.g. trifluoroacetic acid anhydride in presence of a base e.g. diisopropylethylamine (DIPEA), in a solvent e.g. dichloromethane or without a solvent at a temperature between −78° C. and 150° C., preferably between −30° C. and room temperature.

g)—the preparation of compounds wherein A4 is

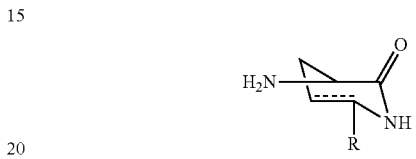

and A6 is

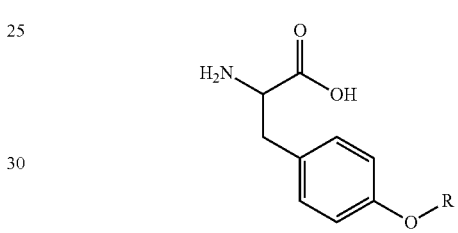

wherein R preferably is alkyl, substituted alkyl, acyl, alkoxycarbonyl by treatment of a compound wherein A4 is

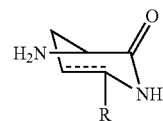

and A6 is Tyr
with an alkylating agent e.g. methyl iodide, benzyl bromide, proargyl bromide or an acylating agent e.g. ethyl chloroformate or an alkyl or aryl isocyanate in presence of a base e.g. sodium carbonate in a solvent e.g. MIT or without a solvent at a temperature between −78° C. and 150° C., preferentially between −30° C. and room temperature, preferably promoted by ultrasound.

Unless otherwise indicated, all numbers expressing quantities of ingredients, properties such as molecular weight, reaction conditions, $IC_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

Production of the Compounds

Example 1.1

Production of the Compounds of Formula (II)-(VII), (XI)-(XIV) and (XVII)

Strain: The *Chondromyces crocatus* strain was isolated from an environmental sample, rotten wood of a walnut tree, in our laboratories.

The strain has been unambiguously identified as a *Chondromyces crocatus* based on the morphology of the fruiting bodies as well as on the partial sequence of the 16S-RNA gene. *C. crocatus* was assigned to biological risk group 1 by the DSMZ (DSMZ (2007)). *Chondromyces* is a genus in the family Polyangiaceae, which belongs to the order Myxococcales within the Delta-proteobacteria. Bacteria of the order Myxococcales, also called myxobacteria, are gram-negative rod-shaped bacteria with two characteristics distinguishing them from most other bacteria. They swarm on solid surfaces using an active gliding mechanism and aggregate to form fruiting bodies upon starvation (Kaiser (2003)).

The *Chondromyces crocatus* strain of the invention has been deposited at the DSMZ under the accession number 19329.

The *Chondromyces crocatus* strain of the invention is not viable as a pure culture and cannot be maintained without a companion strain. The companion strain can be obtained and maintained as a pure culture by streaking an aliquot of a fermentation co-culture on agar plates (LB medium). A similar observation was made by the Reichenbach group (Jacobi, et al. (1996), Jacobi, et al. (1997)). Based on a partial DNA sequence of the 16S-rRNA gene of the companion strain of *Chondromyces crocatus* of this invention, the closest match is *Bosea thiooxidans* from the order Rhizobiales within the Alpha-proteobacteria. The 424 bp sequence fragment 16S-rRNA investigated has about 98% identity (at least 8 nucleotide exchanges) to sequence AF508112 (*B. thiooxidans*) from genebank. *B. thiooxidans* was isolated from soil samples collected from different agricultural fields around Calcutta, India. It is capable to oxidate reduced inorganic sulfur compounds in the presence of some organic substrates and was described as a novel species and a novel genus in 1996 (Das, et al. (1996)). A phylogenetic tree derived from the partial 16S-RNA sequences of all 5 described *Bosea* species indicates a separate position for the *Bosea* companion strain isolated from *C. crocatus*.

Cultivation: 100 L fermentor cultures were performed according to the following protocol: Precultures were started by inoculation of 5 ml (=10%) from a liquid culture of *Chondromyces crocatus* strain of the invention into 50 ml of medium MD1 (adapted after Bode et al. 2003, see table 6) in a 200-ml baffled shake flask. After 11 clays incubation at 30° C. and 120 rpm on a rotary shaker a 1st intermediate culture was started by inoculation of 10 ml each (=10%) from the preculture into 5×100 ml of medium MD1 in 500-ml baffled shake flasks. After 7 clays incubation at 30° C. and 120 rpm on a rotary shaker a 2nd intermediate culture was started by inoculation of 25 ml each (=5%) from the 1st intermediate culture into 19×500 ml of medium MD1 in 2-L nonbaffled shake flasks. After 6 days of incubation at 30° C. and 150 rpm on a rotary shaker the whole 2nd intermediate culture (9.5 liters=9.5%) was used to inoculate 100 liters of production medium POL1. (adapted after Kunze et al. 1995, see table 7)

This 100-L main culture was performed in a 100-L scale steel tank fermentor. Temperature was controlled at 30° C., aeration was 20 l/min (=0.2 vvm) and agitation speed was 50 rpm. A slight overpressure of 0.5 bar was maintained inside of the fermentor vessel. Culture pH was maintained at 6.9-7.1 by controlled addition of 3N $H_2SO_4$ or 3N NaOH. After a lag-phase of about 1 day oxygen consumption accelerated for about 4 days indicating exponential growth of the culture. During the last 2 days oxygen consumption was slightly reduced indicating a stationary phase of the culture. After 7 days the culture was harvested with a titer of 5.3 mg/l of a cyclic depsipeptide according to Formula II.

Extraction: The whole fermentation broth was transferred into a 1600 l steel vessel and decanted for 1 hour. The wet cell pellet (200 g) was harvested from the bottom fraction by filtration through a paper filter. The cell pellet was extracted 3 times by turaxing it 30 minutes each with 10 l ethyl acetate. Then the residual water was separated from the solvent phase. The solvent phase was washed with 5 l water and then evaporated to obtain a dry extract referred to as 'cell extract'. The culture filtrate was extracted with 200 l ethyl acetate. After 2 hours contact time, including 1 hour of turaxing, the organic phase was separated, washed with 20 l water and finally evaporated to obtain a dry extract referred to as 'culture filtrate extract'.

Compound isolation: The culture filtrate extract (4.4 g) was dissolved in 80 mL Methanol. The insoluble ingredients were removed by centrifugation and the supernatant was evaporated to dryness yielding in 3.3 g extract. The extract was dissolved in 7.5 mL MeOH, 3 mL DMSO and 0.5 mL dichloromethane and purified by reversed phase chromatography (Waters Sunfire RP18 10 μm, 30×150 mm) using 0.01% formic acid (solvent A), and acetonitrile containing 0.1% formic acid (solvent B) as solvents The flow rate was 50 mL/min. The gradient is shown in Table 1. The material was purified in 7 chromatographic runs. From each run the collected fractions were analyzed by HPLC, fractions containing the cyclic depsipeptide according to the invention were combined and evaporated in vacuum to dryness. The chromatography yielded in 134 mg cyclic depsipeptide according to formula (II) with a purity of >97% and 80 mg with a purity of 90%.

TABLE 1

HPLC gradient used for purification of the cyclic depsipeptide according to formula (II)

| time (min) | solvent A (%) | solvent B (%) |
|---|---|---|
| 0.0 | 90 | 10 |
| 1.0 | 90 | 10 |
| 23.0 | 50 | 50 |
| 23.1 | 0 | 100 |
| 27.0 | 0 | 100 |
| 27.1 | 90 | 10 |
| 30.0 | 90 | 10 |

TABLE 2

Gradient used for normal phase separation

| time (min) | cyclohexane (%) | ethyl acetate (%) | methanol (%) |
|---|---|---|---|
| 0 | 75 | 25 | 0 |
| 10 | 75 | 25 | 0 |
| 33 | 25 | 75 | 0 |
| 56 | 20 | 70 | 10 |
| 79 | 0 | 50 | 50 |
| 93 | 0 | 50 | 50 |

The cell extract (6.67 g) was dissolved in dichloromethane/methanol 4:1. The solution was filtered and the filtrate was adsorbed on diatom (2 g diatom/1 g extract, Isolute®, International Sorbent Technology Ltd., Hengoed Mid Glam, UK) followed by evaporation. The solid residue was loaded on a pre-packed silica gel column (4×18 cm, 90 g silica gel 40-63) and eluted with a gradient of cyclohexane, ethyl acetate and methanol. The gradient is shown in Table 2, the flow rate was 28 ml/min. Fractions volumes of 28 ml were collected. The fractions were combined according to the peaks visible in the UV-trace yielding in 12 pooled fractions (A-L). Fractions containing the depsipeptides (H-J) were further purified using reversed-phase chromatography. The chromatographic method and work up procedure is identical to the purification method described for the culture filtrate. In total 46.1 mg cyclic depsipeptide according to formula (II), 17.9 mg cyclic depsipeptide according to formula (III) and 6.1 mg of a 1:1 mixture of the depsipetides according to formula (VI) and (VII) have been isolated. The assignment of the structures of compound (VI) and (VII) is based on high resolution MS and the comparison of the $^1$H-NMR data of the mixture of compound (VI) and (VII) with the $^1$H-NMR data of compound (II).

Other cyclic depsipeptide according to formula (II) have also been found at a lesser concentration in the cell extract. Among these other cyclic depsipeptides were those according to formula (IV), (V) and (XI)-(XV) and (XVII).

Characterization of Compounds:

Physical Data of Compound of Formula (II)

IR (KBr pellet): 3337, 3297, 3062, 2966, 2936, 2877, 1736, 1659, 1533, 1519, 1464, 1445, 1410, 1385, 1368, 1249, 1232, 1205, 989, 832 cm$^{-1}$ FT-MS (9.4 T APEX-III): 951.5165; calc. for $C_{46}H_{72}N_5O_{12}$+Na: 951.5162

$^1$H NMR (600 MHz, d$_6$-DMSO) δ$_H$: −0.10 (3H, d, J=7.0 Hz), 0.65 (4H, m), 0.78 (3H, d, J=7.0 Hz), 0.82 (3H, t, J=7.2 Hz), 0.85 (3H, d, J=7.0 Hz), 0.89 (3H, d, J=7.0 Hz), 1.02 (1H, m), 1.03 (6H, 2×d, J=7.0 Hz), 1.10 (1H, m), 1.21 (3H, d, J=7.0 Hz), 1.25 (1H, m), 1.40 (1H, m), 1.52 (1H, m), 1.76 (6H, m), 1.84 (1H, m), 1.93 (1H, m), 2.15 (2H, m), 2.48 (1H, m), 2.59 (1H, m), 2.69 (1H, m), 2.72 (3H, s), 3.17 (1H, m), 4.32 (2H, m), 4.44 (2H, m), 4.64 (1H, d, J=9.5 Hz), 4.71 (1H, m), 4.94 (1H, s), 5.06 (1H, m), 5.49 (1H, m), 6.08 (1H, d, J=2.2 Hz), 6.65 (2H, d, J=8.4), 6.74 (1H, s), 7.00 (2H, d, J=8.4 Hz), 7.27 (1H, s), 7.36 (1H, d, J=9.5 Hz), 7.66 (1H, d, J=10.2 Hz), 7.74 (1H, d, J=8.8 Hz), 8.02 (1H, d, J=8.1 Hz), 8.43 (1H, d, J=8.1 Hz), 9.19 (1H, s).

$^{13}$C NMR (150 MHz) d$_6$-DMSO δ$_C$: 10.35, CH$_3$; 11.22, CH$_3$; 13.79, CH$_3$; 16.00, CH$_3$; 17.63, CH$_3$; 19.49, 2×CH$_3$; 20.83, CH$_3$; 21.72, CH$_2$; 23.30, CH$_3$; 23.70, CH$_2$; 24.16, CH; 24.41, CH$_2$; 27.35, CH$_2$; 29.74, CH$_2$; 30.07, CH$_3$; 31.44, CH$_2$; 33.13, CH; 33.19, CH$_2$; 33.68, CH; 37.39, CH; 39.05, CH$_2$; 48.75, CH; 50.59, CH; 52.01, CH; 54.11, CH; 54.65, CH; 55.24, CH; 60.60, CH; 71.86 CH; 73.89, CH; 115.28, 2×CH; 127.31, Cq; 130.35, 2×CH; 156.25, Cq; 169.09, Cq; 169.25, Cq; 169.34, Cq; 169.74, Cq; 170.60, Cq; 172.41, Cq; 172.52, Cq; 173.78, Cq; 176.32, Cq

Physical Data of Compound of Formula (III)

FT-MS (9.4 T APEX-III). Found: 965.5318; calc. for $C_{47}H_{74}N_8O_{12}$+Na: 965.5318

$^1$H NMR (600 MHz) d$_6$-DMSO δ$_H$: −0.10 (3H, d, J=7.0 Hz), 0.64 (4H, m), 0.78 (3H, d, J=7.0 Hz), 0.82 (3H, t, J=7.0 Hz), 0.83 (3H, t, J=7.3 Hz), 0.85 (3H, d, J=7.0 Hz), 0.89 (3H, d, J=7.0 Hz), 1.01 (3H, d, J=7.1 Hz), 1.04 (1H, m), 1.10 (1H, m), 1.21 (3H, d, J=7.0 Hz), 1.25 (1H, m), 1.32 (1H, m), 1.40 (1H, m), 1.53 (2H, m), 1.77 (6H, m), 1.84 (1H, m), 1.92 (1H, m), 2.12 (1H, m), 2.16 (1H, m), 2.28 (1H, m), 2.59 (1H, m), 2.68 (1H, m), 2.72 (3H, s), 3.17 (1H, m), 4.32 (1H, m), 4.38 (1H, m), 4.43 (1H, d, J=10.2 Hz), 4.46 (1H, m), 4.63 (1H, d, J=9.5 Hz), 4.71 (1H, m), 4.94 (1H, m), 5.06 (1H, m), 5.49 (1H, m), 6.11 (1H, s, broad), 6.65 (2H, d, J=8.8 Hz), 6.73 (1H, s), 7.00 (2H, d, J=8.8 Hz), 7.27 (1H, s), 7.37 (1H, d, J=9.5 Hz), 7.66 (1H, d, J=10.2 Hz), 7.75 (1H, d, J=9.7 Hz), 8.07 (1H, d, J=8.1 Hz), 8.45 (1H, d, J=8.8 Hz), 9.24 (1H, broad)

Physical Data of Compound of Formula (IV)

FT-MS (9.4 T APEX-III). Found: 947.5196; calc. for $C_{47}H_{72}N_8O_{11}$+Na: 947.5213

$^1$H NMR (600 MHz) d$_6$-DMSO δ$_H$: 0.08 (3H, d, J=7.0 Hz), 0.68 (3H, t, J=7.2 Hz), 0.71 (3H, d, J=7.0 Hz), 0.78 (3H, d, J=7.0 Hz), 0.83 (3H, t, J=7.3 Hz), 0.84 (1H, m), 0.87 (3H, t, J=7.2 Hz), 0.88 (3H, d, J=7.0 Hz), 0.99 (3H, d, J=7.1 Hz), 1.08 (1H, m), 1.17 (3H, d, J=6.7 Hz), 1.18 (1H, m), 1.31 (2H, m), 1.43 (1H, m), 1.51 (1H, m), 1.54 (1H, m), 1.76 (2H, m), 1.90 (1H, m), 1.94 (1H, m), 2.01 (1H, m), 2.10 (1H, m), 2.16 (1H, m), 2.26 (1H, m), 2.46 (2H, m), 2.73 (1H, m), 2.74 (3H, s), 3.19 (1H, m), 4.34 (1H, m), 4.36 (1H, m), 4.51 (1H, m), 4.55 (1H, m), 4.66 (1H, d, J=10.0 Hz), 4.79 (1H, d, J=11.0 Hz), 5.19 (1H, m), 5.28 (1H, m), 5.44 (1H, m), 6.25 (1H, d, J=7.3 Hz), 6.33 (1H, d, J=8.8 Hz), 6.68 (2H, d, J=8.8 Hz), 6.75 (1H, s), 7.04 (2H, d, J=8.8 Hz), 7.28 (1H, s), 7.32 (1H, d, J=8.8 Hz), 7.91 (1H, d, J=9.5 Hz), 8.05 (1H, d, J=8.1 Hz), 8.57 (1H, d, J=8.9 Hz), 9.38 (1H, broad)

Physical Data of Compound of Formula (V)

FT-MS (9.4 T APEX-III). Found: 933.5053; calc. for $C_{46}H_{70}N_8O_{11}$+Na: 953.5056

$^1$H NA/IR (600 MHz) d$_6$-DMSO δ$_H$: 0.08 (3H, d, J=7.0 Hz), 0.68 (3H, t, J=7.2 Hz), 0.71 (3H, d, J=7.0 Hz), 0.79 (3H, d, J=7.0 Hz), 0.83 (1H, m), 0.88 (3H, t, J=7.2 Hz), 0.89 (3H, d, J=7.0 Hz), 1.01 (3H, d, J=7.0 Hz), 1.03 (3H, d, J=7.0 Hz) 1.08 (1H, m), 1.17 (3H, d, J=6.7 Hz), 1.20 (1H, m), 1.31 (1H, m), 1.42 (1H, m), 1.54 (1H, m), 1.74 (2H, m), 1.91 (2H, m), 2.02 (1H, m), 2.10 (1H, m), 2.15 (1H, m), 2.46 (3H, m), 2.75 (3H, s), 2.76 (1H, m), 3.19 (1H, m), 4.32 (1H, m), 4.34 (1H, m), 4.51 (1H, m), 4.55 (1H, m), 4.66 (1H, d, J=9.5 Hz), 4.79 (1H, d, J=11.0 Hz), 5.19 (1H, m), 5.28 (1H, m), 5.43 (1H, m), 6.25 (1H, d, J=7.0 Hz), 6.33 (1H, d, J=8.5 Hz), 6.68 (2H, d, J=8.8 Hz), 6.75 (1H, s), 7.04 (2H, d, J=8.8 Hz), 7.28 (1H, s), 7.31 (1H, d, J=8.8 Hz), 7.90 (1H, d, J=9.5 Hz), 7.99 (1H, d, J=8.1 Hz), 8.52 (1H, d, J=8.8 Hz), 9.30 (1H, broad)

Physical Data of Compound of Formula (XI)

ESI-MS: pos. mode: m/z=951.5 (M+Na), neg. Mode: m/z=927.5 (M−H); monoisotopic MW 928.5, $C_{46}H_{72}N_8O_{12}$ $^1$H NMR (600 MHz) $d_6$-DMSO $\delta_H$: −0.11 (3H, d, J=6.6 Hz), 0.64 (4H, m), 0.77 (3H, d, J=6.6 Hz), 0.83 (3H, m), 0.85 (3H, m), 0.87 (3H, m), 0.89 (3H, m), 1.01 (3H, m), 1.10 (1H, m), 1.21 (3H, d, J=5.9 Hz), 1.32 (1H, m), 1.40 (1H, m), 1.52 (2H, m), 1.75 (5H, m), 1.84 (1H, m), 1.91 (1H, m), 2.05 (1H, m), 2.15 (2H, m), 2.27 (1H, m), 2.59 (1H, m), 2.68 (1H, m), 2.73 (3H, s), 3.16 (1H, m), 4.31 (1H, m), 4.37 (1H, m), 4.43 (1H, m), 4.45 (1H, m), 4.63 (1H, d, J=8.8 Hz), 4.69 (1H, m), 4.94 (1H, m), 5.05 (1H, m), 5.50 (1H, m), 6.15 (1H, s, broad), 6.65 (2H, d, J=8.1 Hz), 6.75 (1H, s), 7.00 (2H, d, J=8.1 Hz), 7.29 (1H, s), 7.37 (1H, d, J=9.5 Hz), 7.64 (1H, d, J=9.5 Hz), 7.78 (1H, d, J=8.8 Hz), 8.09 (1H, d, J=8.1 Hz), 8.49 (1H, d, J=9.5 Hz), (OH of tyrosine not visible)

Physical Data of Compound of Formula (XII)

ESI-MS: pos. mode: m/z=923.5 (M+Na), neg. Mode: m/z=899.5 (M−H); monoisotopic MW 900.5, $C_{44}H_{68}N_8O_{12}$.

$^1$H NMR (500 MHz) $d_6$-DMSO $\delta_H$: −0.11 (3H, d, J=6.4 Hz), 0.63 (4H, m), 0.75 (3H, d, J=6.4 Hz), 0.83 (6H, d, J=7.0 Hz), 0.87 (3H, d, J=6.4 Hz), 1.03 (1H, m), 1.10 (1H, m), 1.20 (3H, d, J=6.4 Hz), 1.25 (1H, m), 1.38 (1H, m), 1.50 (1H, m), 1.73 (1H, m), 1.75 (2H, m), 1.77 (1H, m), 1.79 (3H, m), 1.85 (3H, s), 1.85 (1H, m), 2.12 (1H, m), 2.16 (1H, m), 2.55 (1H, m), 2.67 (1H, m), 2.70 (3H, s), 3.13 (1H, m), 4.30 (1H, m), 4.40 (1H, m), 4.43 (2H, m), 4.59 (1H, d, J=9.5 hz), 4.71 (1H, m), 4.92 (1H, m), 5.02 (1H, m), 5.46 (1H, m), 6.08 (1H, s, broad), 6.62 (2H, d, J=8.5 Hz), 6.71 (1H, s), 6.97 (2H, d, J=8.5 Hz), 7.22 (1H, s), 7.34 (1H, d, J=9.2 Hz), 7.64 (1H, d, J=9.5 Hz), 7.93 (1H, d, J=9.2 Hz), 8.06 (1H, d, J=7.6 Hz), 8.39 (1H, d, J=8.5 Hz), 9.06 (1H, s, broad)

Physical Data of Compound of Formula (XIII)

FT-MS (9.4 T APEX-III). Found: 961.5039; calc. for $C_{49}H_{70}N_8O_{12}$+Na: 985.5005

$^1$H NMR (500 MHz) $d_6$-DMSO $\delta_H$: −0.12 (3H, d, J=6.4 Hz), 0.62 (4H, m), 0.75 (3H, d, J=6.4 Hz), 0.81 (4H, m), 0.87 (3H, d, J=6.4 Hz), 1.08 (1H, m), 1.20 (3H, m), 1.22 (3H, m), 1.38 (1H, m), 1.46 (1H, m), 1.50 (1H, m), 1.71 (1H, m), 1.73 (2H, m), 1.76 (2H, m), 1.82 (1H, m), 1.94 (1H, m), 2.01 (1H, m), 2.23 (2H, m), 2.56 (1H, m), 2.66 (1H, m), 2.69 (3H, s), 3.13 (1H, m), 4.30 (1H, m), 4.41 (2H, m), 4.55 (1H, m), 4.65 (1H, d, J=9.5 Hz), 4.70 (1H, m), 4.92 (1H, m), 5.04 (1H, m), 5.48 (1H, m), 6.09 (1H, s, broad), 6.64 (2H, d, J=8.5 Hz), 6.81 (1H, s), 6.97 (2H, d, J=8.5 Hz), 7.33 (1H, s), 7.35 (1H, d, J=9.2 Hz), 7.46 (2H, t, J=7.3 Hz), 7.53 (1H, t, J=7.3 Hz), 7.66 (1H, d, J=9.5 Hz), 7.88 (2H, d, J=7.3 Hz), 7.95 (1H, d, J=9.5 Hz), 8.46 (1H, d, J=8.5 Hz), 8.71 (1H, d, J=7.3 Hz); (OH of tyrosine not visible)

Physical Data of Compound of Formula (XIV)

ESI-MS: pos. mode: m/z=927.5 (M+H), neg. Mode: m/z=925.5 (M−H); monoisotopic MW 926.5, $C_{47}H_{74}N_8O_{11}$ $^1$H NMR (500 MHz) $d_6$-DMSO $\delta_H$: 0.00 (1H, m), 0.48 (3H, t, J=7.5 Hz), 0.70 (3H, d, J=7.0 Hz), 0.73 (3H, t, J=7.0 Hz), 0.76 (3H, d, J=7.3 Hz), 0.79 (3H, t, J=7.3 Hz), 0.83 (6H, d, J=6.4 Hz), 0.89 (1H, m), 0.95 (1H, m), 0.98 (3H, d, J=7.0 Hz), 1.04 (3H, d, J=6.1 Hz), 1.09 (1H, m), 1.17 (1H, m), 1.28 (1H, m), 1.31 (1H, m), 1.36 (1H, m), 1.38 (1H, m), 1.55 (1H, m), 1.61 (1H, m), 1.68 (1H, m), 1.79 (1H, m), 1.82 (1H, m), 1.95 (2H, m), 2.15 (3H, m), 2.25 (1H, m), 2.66 (3H, s), 2.76 (1H, m), 3.14 (1H, m), 3.40 (1H, m), 3.42 (1H, m), 4.33 (1H, m), 4.36 (1H, m), 4.45 (1H, m), 4.55 (2H, m), 4.69 (1H, m), 5.06 (1H, m), 6.63 (2H, d, J=8.2 Hz), 6.71 (1H, s, broad), 7.01 (2H, d, J=8.2 Hz), 7.27 (1H, s, broad), 7.36 (1H, d, J=9.5 Hz), 8.00 (1H, d, J=9.5 Hz), 8.17 (1H, d, J=4.00 Hz), 8.22 (1H, d, J=7.3 Hz), 8.53 (1H, d, J=9.5 Hz), 9.14 (1H, s, broad)

Physical Data of Compound of Formula (XVII)

ESI-MS: pos. mode: m/z=985.4 (M+Na), neg. Mode: m/z=961.5 (M−H); monoisotopic MW 962.5, $C_{45}H_{70}N_8O_{13}S$ $^1$H NMR (600 MHz) $d_6$-DMSO $\delta_H$:). $\delta_H$: no assignment of chemical shifts (mixture of two diastereomers, structure assignment trough comparison with other related compounds, e.g. compound (II)

Example 1.2

Production of Compound of Formula (VIII, IX, X)

Strain: The *Chondromyces robustus* strain was isolated from a dung sample. The *Chondromyces robustus* strain of the invention has been identified as a *Chondromyces robustus* based on the morphology of the fruiting bodies as well as on the partial sequence of the 16S-RNA gene. *C. robustus* was assigned to biological risk group 1 by the DSMZ (DSMZ (2007)). *Chondromyces* is a genus in the family Polyangiaceae, which belongs to the order Myxococcales within the Delta-proteobacteria. Bacteria of the order Myxococcales, also called myxobacteria, are gram-negative rod-shaped bacteria with two characteristics distinguishing them from most other bacteria. They swarm on solid surfaces using an active gliding mechanism and aggregate to form fruiting bodies upon starvation (Kaiser (2003)).

The *Chondromyces robustus* strain of the invention has been deposited at the DSMZ under the accession number 19330.

Cultivation: 100 L fermentor cultures were performed according to the following protocol:

Precultures were started by inoculation of 20 ml each (=20%) from a liquid culture of the *Chondromyces robustus* strain of the invention into 6×100 ml of medium MD1 (adapted after Bode et al. 2003) in 500-ml baffled shake flasks. After 1 day of incubation at 30° C. and 120 rpm on a rotary shaker a 1$^{st}$ intermediate culture was started by inoculation of 100 ml each (=25%) from the preculture into 6×400 ml of medium MD1 in 2-L baffled shake flasks. After 3 days incubation at 30° C. and 120 rpm on a rotary shaker a 2$^{nd}$ intermediate culture was started by inoculation of 3 liters (=20%) from the 1$^{st}$ intermediate culture into a 20-L steel tank fermentor containing 15 liters of medium MD1. Temperature was controlled at 30° C., aeration was 20 l/min (=1.0 vvm) and agitation speed was 80 rpm. A slight overpressure of 0.5 bar was maintained inside of the fermentor vessel. Although there was no pH control the pH of the culture decreased only slightly from pH 6.95 at start to pH 6.88 on day 7. After 7 days the whole 2$^{nd}$ d intermediate culture (18 liters=20%) was used to inoculate 90 liters of production medium POL1 (adapted after Kunze et al. 1995) (starting volume=108 liters). The main culture was performed in a 100-L scale steel tank fermentor. Temperature was controlled at 30° C., aeration was 30 l/min (=0.3 vvm) and agitation speed was in the beginning 50 rpm and after 4 days 80 rpm. A slight overpressure of 0.5 bar was maintained inside of the fermentor vessel. Culture pH was maintained at 6.8-7.2 by controlled addition of 2N $HSO_4$ or 1.5N NaOH. After 14 days the culture was harvested with a titer of 3 mg/l Extraction: The whole fermentation broth was transferred into a 1600 l steel vessel and decanted for 1 hour. The wet cell pellet (about 200 g) was harvested from the bottom fraction by filtration through a paper filter. The cell pellet was extracted 3 times by turaxing it 30 minutes each with 10 l ethyl acetate. Then the residual water was separated from the solvent phase. The solvent phase was washed with 5 l water and then evaporated to obtain 11.9 g dry extract referred to as 'cell extract'.

The culture filtrate was extracted with 200 l ethyl acetate. After 2 hours contact time, including 1 hour of turaxing, the organic phase was separated, washed with 20 l water and finally evaporated to obtain 12.5 g of dry extract referred to as 'culture filtrate extract'.

Compound isolation: Each extract (from mycelium and culture filtrate) was dissolved in dichloromethane/methanol 4:1. The solution was filtered and the filtrate was adsorbed on diatom (2 g diatom/1 g extract, Isolute®, International Sorbent Technology Ltd., Hengoed Mid Glam, UK) followed by evaporation. The solid residue was loaded on a pre-packed silica gel column (4×18 cm, 100 g silica gel 40-63) and eluted with a gradient of cyclohexane, ethyl acetate and methanol. The gradient is shown in Table 4, the flow rate was 28 ml/min. Fractions volumes of 28 ml were collected. The fractions were combined according to the peaks visible in the UV-trace. The fraction containing the cyclic depsipeptide of the invention was further purified using reversed-phase chromatography (Waters Sunfire RP18 10 μm, 30×150 mm) using 0.01% formic acid (solvent A), and acetonitrile containing 0.1% formic acid (solvent B) as solvents. The flow rate was 50 mL/min. The gradient is shown in Table 5. For injection the material was dissolved in MeOH/DMSO 1:1 (concentration 200 mg/mL). The collected fractions were analyzed by HPLC, fractions containing the cyclic depsipeptide of the invention were combined and evaporated in vacuum to dryness. The chromatography of the extract yielded in 52 mg pure (>97%) cyclic depsipeptide according to formula (VIII) A total of 85 mg pure cyclic depsipeptide according to formula (VIII) could be isolated from the combined extracts.

Other cyclic depsipeptide according to formula (VIII) have also been found at a lesser concentration in the cell extract. Among these other cyclic depsipeptides were those according to formula (IX) and (X).

TABLE 4

Gradient used for normal phase separation

| time (min) | cyclohexane (%) | ethyl acetate (%) | methanol (%) |
|---|---|---|---|
| 10 | 75 | 25 | 0 |
| 33 | 25 | 75 | 0 |
| 56 | 20 | 70 | 10 |
| 79 | 0 | 50 | 50 |
| 93 | 0 | 50 | 50 |

TABLE 5

HPLC gradient used for purification of cyclic depsipeptide according to formula (VIII)

| time (min) | solvent A (%) | solvent B (%) |
|---|---|---|
| 0.0 | 75 | 25 |
| 1.0 | 75 | 25 |
| 23.0 | 55 | 45 |
| 23.1 | 0 | 100 |
| 27.0 | 0 | 100 |
| 27.1 | 75 | 25 |
| 30.0 | 75 | 25 |

Media (Adjusted to pH 7.0 with 50 mM HEPES)

TABLE 6

MD1 (pre-culture medium)

| Substance | Concentration [g/L] |
|---|---|
| Casitone | 3 |
| $CaCl_2 \times 2\,H_2O$ | 0.5 |
| $MgSO_4 \times 7\,H_2O$ | 2 |
| D(+)-Glucose water free | 1 |
| Cyanocobalamine | 0.5 mg |
| Antifoam B | 0.2 mL |
| Ferrioxamine solution [100 ng/mL] | 1 mL |

TABLE 7

POL1 (production medium)

| Substance | Concentration [g/L] |
|---|---|
| Potato protein | 4 |
| Soluble starch | 3 |
| $CaCl_2 \times 2\,H_2O$ | 0.5 |
| $MgSO_4 \times 7\,H_2O$ | 2 |
| Cyanocobalamine | 0.25 mg |
| HEPES | 12 |
| Standard Trace Element Solution 1901 | 1 mL |
| XAD16 | 35 |

Characterization of Compounds:
Physical Data of Compound of Formula (VIII)
FT-MS (9.4 T APEX-III). Found: 985.5007; calc. for $C_{49}H_{70}N_8O_{12}$+Na: 985.5005.

$^1$H NMR (600 MHz) $d_6$-DMSO $\delta_H$: 0.74 (6H, d, J=7.0 Hz), 0.85 (3H, d, J=7.0 Hz), 0.88 (3H, d, J=7.0 Hz), 0.89 (6H, d, J=7.0 Hz), 1.18 (3H, d, J=6.7 Hz), 1.32 (1H, m), 1.46 (1H, m), 1.57 (2H, m), 1.72 (3H, m), 1.81 (1H, m), 1.88 (1H, m), 1.98 (1H, m), 2.02 (2H, m), 2.11 (3H, m), 2.42 (1H, m), 2.73 (1H, m), 2.77 (3H, s), 2.87 (1H, m), 3.12 (1H, m), 3.64 (1H, m), 4.23 (1H, m), 4.40 (1H, m), 4.58 (1H, d, J=9.5 Hz), 4.75 (2H, m), 4.93 (1H, m), 5.07 (1H, s), 5.40 (1H, m), 6.03 (1H, s), 6.74 (1H, s), 6.79 (2H, d, J=8.4 Hz), 6.84 (2H, d, J=7.8 Hz), 7.02 (2H, d, J=8.4 Hz), 7.10 (1H, d, J=9.3 Hz), 7.14 (1H, t, J=7.8 Hz), 7.19 (2H, t, J=7.8 Hz), 7.26 (1H, s), 7.42 (1H, d, J=9.8 Hz), 7.89 (1H, d, J=9.2 Hz), 8.03 (1H, d, J=7.9 Hz), 8.38 (1H, d, J=8.9 Hz), 9.40 (1H, s)

$^{13}$C NMR (150 MHz) $d_6$-DMSO $\delta_C$: 17.13, $CH_3$; 17.63, $CH_3$; 19.32, $CH_3$; 20.90, $CH_3$; 21.64, $CH_2$; 22.34, $CH_3$; 22.34, $CH_3$; 23.32, $CH_3$; 24.10, CH; 25.63, CH; 27.63, $CH_2$; 29.30, $CH_2$; 30.37, $CH_3$; 30.86, CH; 31.52, $CH_2$; 32.83, $CH_2$; 35.33, $CH_2$; 38.98, $CH_2$; 44.42, $CH_2$; 48.52, CH; 50.19, CH; 50.24, CH; 51.99, CH; 54.62, CH; 55.63, CH; 60.90, CH; 71.86 CH; 73.70, CH; 115.32, 2×CH; 126.21, CH; 127.50, Cq; 127.74, 2×CH; 129.42, 2×CH; 130.43, 2×CH; 136.72, Cq; 156.23, Cq; 168.93, Cq; 169.18, Cq; 169.18, Cq; 170.18, Cq; 170.39, Cq; 171.72, Cq; 171.96, Cq; 172.50, Cq; 173.82, Cq Physical Data of Compound of Formula (IX)
FT-MS (9.4 T APEX-III). Found: 969.5058; calc. for $C_{49}H_{70}N_8O_{11}$+Na; 969.5056.

$^1$H NMR (600 MHz) $d_6$-DMSO $\delta_H$:): 0.53 (3H, d, J=6.6 Hz), 0.73 (3H, d, J=6.6 Hz), 0.74 (3H, d, J=6.6 Hz), 0.81 (3H, d, J=6.6 Hz), 0.86 (6H, d, J=6.6 Hz), 1.08 (3H, d, J=6.5 Hz), 1.20 (1H, m), 1.33 (3H, m), 1.52 (1H, m), 1.64 (1H, m), 1.80 (2H, m), 2.01 (1H, m), 2.04 (2H, m), 2.15 (4H, m), 2.25 (1H, m), 2.30 (1H, m), 2.74 (3H, s), 2.83 (1H, m), 3.12 (1H, m), 3.32 (1H, m), 3.38 (1H, m), 4.14 (1H, m), 4.27 (1H, m), 4.40 (1H, m), 4.59 (1H, m), 4.61 (1H, m), 4.94 (1H, m), 4.99 (1H, m), 5.10 (1H, m), 6.42 (2H, d, J=8.8 Hz), 6.75 (1H, s), 7.04 (2H, d, J=8.8 Hz), 7.10 (1H, t, J=7.3 Hz), 7.15 (2H, t, J=7.3 Hz), 7.23 (2H, d, J=7.3 Hz), 7.30 (1H, s), 7.41 (1H, d, J=9.5 Hz), 8.05 (1H, d, J=9.5 Hz), 8.23 (1H, d, J=8.1 Hz), 8.47 (1H, d, J=4.4 Hz), 8.71 (1H, d, J=10.2 Hz). (signal of proton of hydroxy group of tyrosine not visible)

Physical Data of Compound of Formula (X)

FT-MS (9.4 T APEX-III). Found: 955.4896; calc. for $C_{48}H_{68}N_8O_{11}$+Na: 955.4900.

$^1$H NMR (600 MHz) d$_6$-DMSO $\square_H$:). $\square_H$: no assignment of chemical shifts (mixture of rotameres, assignment of structure based on comparison of NMR data (missing N-methyl-group) with NMR data of compound (IX).

Example 1.3

Production of Compounds of Formula (XV-XVI)

Strain: The *Chondromyces apiculatus* strain was isolated from a soil sample. The *Chondromyces* strain of the invention has been identified as a *Chondromyces apiculatus* based on the partial sequence of the 16S-RNA gene. *C. apiculatus* was assigned to biological risk group 1 by the DSMZ (DSMZ (2007)). *Chondromyces* is a genus in the family Polyangiaceae, which belongs to the order Myxococcales within the Delta-proteobacteria. Bacteria of the order Myxococcales, also called myxobacteria, are gram-negative rod-shaped bacteria with two characteristics distinguishing them from most other bacteria. They swarm on solid surfaces using an active gliding mechanism and aggregate to form fruiting bodies upon starvation (Kaiser (2003)).

The *Chondromyces robustus* strain of the invention has been deposited at the DSMZ under the accession number DSM 21595.

Cultivation:

Precultures were started by inoculation of 20 ml each (=20%) from a liquid culture of the *Chondromyces apiculatus* strain of the invention into 10×100 ml of medium MD1 (adapted after Bode et al. 2003) in 500-ml baffled shake flasks. After 6 days of incubation at 30° C. and 120 rpm on a rotary shaker the cultures with total volume of 1 L were transferred into a 50 L Wave® bag together with 5 L of medium MD1. After 7 days of incubation in a BioWave 200 SPS reactor (Wave Biotec AG, Switzerland) 40 L of medium M7/14 were added to the bag to start the production. The culture was harvested after 19 days.

Extraction:

For harvesting the air in the headspace of the wave bag was removed with vacuum and the bag was hang up to allow sedimentation of the resin and the cells. After 1 hour of sedimentation 43 l of supernatant were removed and discarded. The residual 71 containing the cells and the resin were frozen overnight. After thawing, cells and resin were gained by filtration through a paper filter. The filtrate was discarded. The cell/resin pellet (wet weight approximately 3 kg) was transferred into a metal vessel and extracted two times with 15 l ethyl acetate, with 5 minutes turaxing during the first extraction. The mixtures of both batches were separated through a paper filtration and the filtrates then unified. After separating the organic solvent phase from the water phase the solvent phase was washed with 2 l of pure water and then evaporated until dry. The water phases were discarded.

Compound isolation: The extract (5 g) was dissolved in dichloromethane/methanol 4:1. The solution was filtered and the filtrate was adsorbed on diatom (2 g diatom/1 g extract, Isolute®, International Sorbent Technology Ltd., Hengoed Mid Glam, UK) followed by evaporation. The solid residue was loaded on a pre-packed silica gel column (4×18 cm, 100 g silica gel 40-63) and eluted with a gradient of cyclohexane, ethyl acetate and methanol. The gradient is shown in Table 2, the flow rate was 28 ml/min. Fractions volumes of 28 ml were collected. The fractions were combined according to the peaks visible in the UV-trace. The fraction containing the cyclic depsipeptides of the invention were further purified using reversed-phase chromatography (Waters Sunfire RP18 10 µm, 30×150 mm) using 0.01% formic acid (solvent A), and acetonitrile containing 0.1% formic acid (solvent B) as solvents. The flow rate was 50 mL/min. The gradient is shown in Table 1. For injection the material was dissolved in 1.6 mL MeOH/DMSO 1:1. The collected fractions were analyzed by HPLC, fractions containing the cyclic depsipeptides of the invention were combined and evaporated in vacuum to dryness. The chromatography of the extract yielded in 7 mg pure cyclic depsipeptide according to formula (XV) and 1.2 g pure cyclic depsipeptide according to formula (XVI)

Media

TABLE 8

MD1 (pre-culture medium)

| Substance | Concentration [g/L] |
|---|---|
| Casitone | 3 |
| $CaCl_2 \times 2\,H_2O$ | 0.5 |
| $MgSO_4 \times 7\,H_2O$ | 2 |
| D(+)-Glucose water free | 1 |
| Cyanocobalamine | 0.5 mg |
| Antifoam B | 0.2 mL |
| Ferrioxamine solution [100 ng/mL] | 1 mL |

(Adjusted to pH 7.0 with 50 mM HEPES)

TABLE 9

M7/14 (production medium)

| Substance | Concentration [g/L] |
|---|---|
| Yeast extract | 1 |
| $CaCl_2 \times 2\,H_2O$ | 1 |
| $MgSO_4 \times 7\,H_2O$ | 1 |
| Potato starch | 5 |
| HEPES | 12 |
| Potato protein | 5 |
| D(+)-Glucose water free | 2 |
| Cyanocobalamine | 0.1 mg |
| Antifoam B | 0.2 mL |
| Ferrioxamine solution [100 ng/mL] | 3 mL |
| XAD-16 resin | 35 |

(Adjusted to pH 7.4)

Characterization of Compounds:

Physical Data of Compound of Formula (XV)

FT-MS (9.4 T APEX-III). Found: 1014.5272; calc. for $C_{50}H_{73}N_9O_{12}$+Na: 1014.5276.

$^1$H NMR (600 MHz) d$_6$-DMSO δ$_H$: 0.72 (3H, d, J=6.6 Hz), 0.82 (3H, d, J=6.6 Hz), 0.85 (6H, d, J=6.6 Hz), 1.01 (1H, m), 1.02 (6H, d, J=6.6 Hz), 1.17 (3H, d, J=6.6 Hz), 1.21 (1H, m), 1.31 (1H, m), 1.36 (2H, m), 1.42 (1H, m), 1.49 (1H, m), 1.54 (1H, m), 1.56 (1H, m), 1.69 (3H, m), 1.79 (1H, m), 1.81 (1H, m), 2.40 (1H, m), 2.48 (1H, m), 2.73 (1H, m), 2.76 (3H, s), 2.87 (1H, m), 2.91 (1H, m), 2.98 (1H, m), 3.10 (1H, m), 3.63 (1H, m), 4.22 (1H, m), 4.42 (1H, td, J=8.1, 5.1 Hz), 4.58 (1H, m), 4.75 (2H, m), 4.90 (1H, m), 5.06 (1H, m), 5.38 (1H, m), 5.42 (2H, broad), 5.96 (1H, t, J=5.5 Hz), 6.06 (1H, s, broad), 6.78 (2H, d, J=8.1 Hz), 6.83 (21-1, d, J=7.3 Hz), 7.00 (2H, d, J=8.1 Hz), 7.10 (1H, d, J=9.5 Hz), 7.14 (1H, t, J=7.3 Hz), 7.19 (2H, t, J=7.3 Hz), 7.46 (1H, d, J=9.5 Hz), 7.77 (1H, d, J=9.5 Hz), 7.97 (1H, d, J=8.1 Hz), 8.37 (1H, d, J=8.8 Hz), 9.50 (1H, s, broad)

Physical Data of Compound of Formula (XVI)

ESI-MS: pos. mode: m/z=1004.4 (M+Na), neg. Mode: m/z=976.5 (M−H); monoisotopic MW 977.5, $C_{49}H_{71}N_9O_{12}$ $^1$H NMR (600 MHz) $d_6$-DMSO $\delta_H$: 0.72 (6H, d, J=6.6 Hz), 0.85 (3H, d, J=6.6 Hz), 0.87 (3H, d, J=6.6 Hz), 1.01 (6H, d, J=6.6 Hz), 1.17 (3H, d, J=6.6 Hz), 1.30 (1H, m), 1.35 (2H, m), 1.43 (1H, m), 1.48 (1H, m), 1.56 (1H, m), 1.57 (1H, m), 1.69 (1H, m), 1.71 (2H, m), 1.79 (1H, m), 2.08 (1H, m), 2.41 (1H, m), 2.48 (1H, m), 2.77 (3H, s), 2.87 (1H, m), 2.92 (1H, m), 2.98 (1H, m), 3.09 (1H, m), 3.63 (1H, m), 4.22 (1H, m), 4.42 (1h, td, J=8.1, 5.1 Hz), 4.57 (1H, m), 4.74 (1, m), 4.76 (1H, m), 491 (1H, m), 5.06 (1H, s), 5.39 (1H, m), 5.43 (2H, s, broad), 5.96 (1H, t, J=5.5 Hz), 6.07 (1H, s, broad), 6.78 (2H, d, J=8.1 Hz), 6.84 (2H, d, J=7.3 Hz), 7.00 (21-1, d, J=8.1 Hz), 7.11 (1H, d, J=9.5 Hz), 7.15 (1H, t, J=7.3 Hz), 7.19 (2H, t, J=7.3 Hz), 7.42 (1H, d, J=9.5 Hz), 7.78 (1H, d, J=9.5 Hz), 7.98 (1H, d, J=8.1 Hz), 8.39 (1H, d, J=8.8 Hz), 9.52 (1H, s, broad)

Example 2

Determination of Biological Activity In Vitro

The compounds of the present invention, e.g. including a compound of formula II-X, exhibit pharmacological activity and are therefore useful as pharmaceuticals. E.g., the compounds of the present invention are found to inhibit Kallikrein-7 activity and HNE activity.

Compounds of the present invention have $IC_{50}$ values between 1 nM and 10 μM as determined in the following assay:

Example 2.1

Kallikrein-7 Inhibitory Activity In Vitro

Materials and Buffers

The fluorescence-quenched substrate Ac-Glu-Asp (EDANS)-Lys-Pro-Ale-Leu-Phe^Arg-Leu-Gly-Lys(DAB-CYL)-Glu-NH$_2$ (where ^ indicates the scissile bond, identified by MS analysis) is purchased from Biosyntan (Berlin, Germany) and kept as a 5 mM stock solution in DMSO at −20° C. All other chemicals are of analytical grade.

Enzymatic reactions are conducted in 50 mM sodium citrate buffer at pH 5.6 containing 150 mM NaCl and 0.05% (w/v) CHAPS.

All protein and peptide containing solutions are handled in siliconized tubes (Life Systems Design, Merenschwand, Switzerland). The compound solutions as well as the enzyme and the substrate solutions are transferred to the 384-well plates (black Cliniplate; cat. no. 95040020 Labsystems Oy, Finland) by means of a CyBi-Well 96-channel pipettor (Cy-Bio AG, Jena, Germany).

Instrumentation for FI Measurements

For fluorescence intensity (FI) measurements an Ultra Evolution reader (TECAN, Maennedorf, Switzerland) is used. The instrument is equipped with a combination of a 350 nm (20 nm bandwidth) and a 500 nm (25 nm bandwidth) bandpass filter for fluorescence excitation and emission acquisition, respectively. To increase the signal:background ratio, an appropriate dichroic mirror is employed. The optical filters and the dichroic mirror are purchased from TECAN. The fluorophores in each well are excited by three flashes per measurement.

Determination of $IC_{50}$ Values

For the determination of $IC_{50}$ values the assay is performed at room temperature in 384-well plates. All final assay volumes were 30 μl. Test compounds are dissolved in 90% (v/v) DMSO/water and diluted in water (containing 0.05% (w/v) CHAPS) to 3-times the desired assay concentration. The 11 final compound concentrations are: 0.3 nM, 1 nM, 3 nM, 10 nM, 30 nM, 100 nM, 300 nM, 1 μM, 3 μM, 10 μM and 30 μM. For each assay, 10 μl water/CHAPS (±test compound) are added per well, followed by 10 μl protease solution (diluted with 1.5× assay buffer). The protease concentration in final assay solution is 0.2 nM (according to the enzyme concentrations determined by the Bradford method). After 1 hour of incubation at room temperature, the reaction is started by addition of 10 μl substrate solution (substrate dissolved in 1.5× assay buffer, final concentration was 2 μM). The effect of the compound on the enzymatic activity is obtained from the linear progress curves and determined from two readings, the first one taken directly after the addition of substrate and the second one after 1 hour. The $IC_{50}$ value is calculated from the plot of percentage of inhibition vs. inhibitor concentration using non-linear regression analysis software (XLfit, Vers. 4.0; ID Business Solution Ltd., Guildford, Surrey, UK).

The cyclic depsipeptides inhibited hKallikrein7 with IC50 values as indicated in table 11.

TABLE 10

| | Cyclic depsipeptide according to formula (II) | Cyclic depsipeptide according to formula (III) |
|---|---|---|
| Enzyme | IC50 μM | IC50 μM |
| hKallikrein7 | 0.001 | 0.0004 |

TABLE 11

| Cyclic depsipeptide according to formula: | human neutrophile elastase IC 50 [μM] | hKallikrein7 IC 50 [μM] |
|---|---|---|
| formula II | 0.01 | 0.001 |
| formula III | 0.01 | 0.0004 |
| formula IV | 0.07 | 0.005 |
| formula V | 0.06 | 0.006 |
| formula IX | 0.01 | 0.001 |
| formula X | 0.2 | 0.02 |
| formula XII | 0.05 | 0.004 |
| formula XIII | 0.03 | 0.0007 |
| formula XIV | 2.7 | 0.2 |
| formula XV | 0.08 | 0.004 |
| example 4 | 0.055 | 0.006 |
| example 5 | 0.005 | 0.008 |
| example 6 | 0.055 | 0.095 |
| example 7 | 0.006 | 0.050 |
| example 9 | 0.003 | 0.002 |
| example 10 | 0.009 | 0.0035 |
| example 11 | 0.012 | 0.006 |
| example 12 | 0.006 | 0.0085 |
| example 13 | 0.004 | 0.006 |
| example 14 | 0.005 | 0.01 |
| example 15 | 0.005 | 0.015 |
| example 16 | 0.005 | 0.015 |
| example 17 | 0.0075 | 0.003 |
| example 18 | 0.0025 | 0.005 |
| example 19 | 0.0135 | 0.0065 |
| example 20 | 0.008 | 0.0015 |
| example 21 | 0.009 | 0.0025 |
| example 22 | 0.04 | 0.006 |
| example 23 | 0.003 | 0.005 |
| example 24 | 0.004 | 0.007 |

TABLE 11-continued

| Cyclic depsipeptide according to formula: | human neutrophile elastase IC 50 [µM] | hKallikrein7 IC 50 [µM] |
|---|---|---|
| example 25 | 0.0025 | 0.00375 |
| example 26 | 0.0045 | 0.00085 |
| example 27 | 0.02 | 0.003 |
| example 28 | 0.03 | 0.0025 |
| example 29 | 0.025 | 0.003 |
| example 30 | 4.55 | 1.05 |
| example 31 | 0.3 | 0.2 |
| example 32 | 0.03 | 0.1 |
| example 33 | 0.035 | 0.0045 |
| example 34 | 0.005 | 0.004 |
| example 35 | 0.003 | 0.0085 |
| example 36 | 0.0035 | 0.0085 |
| example 37 | 0.0025 | 0.0045 |
| example 38 | 0.0015 | 0.004 |
| example 39 | 0.0035 | 0.0085 |
| example 40 | 0.0025 | 0.0065 |
| example 41 | 0.001 | 0.002 |
| example 42 | 0.001 | 0.001 |
| example 43 | 0.001 | 0.0002 |
| example 44 | 0.009 | 0.0035 |
| example 45 | 0.003 | 0.002 |
| example 46 | 0.1 | 0.01 |
| example 47 | 0.01 | 0.1 |

Example 2.2

HNE Inhibitory Activity In Vitro

Materials and Buffers

Human neutrophil elastase (cat. no. SE563) is purchased from Elastin Products Company, Inc. (EPC, Owensville, USA). The dry powder (purity >95% stated by the supplier) was dissolved in 20 mM sodium acetate buffer, pH 5.0, 50% (v/v) glycerol, and frozen at −80° C. in aliquots.

The fluorescence-quenched substrate (DABCYL-Ser-Glu-Val^Asn-Leu-Asp-Ala-Glu-Phe-EDANS, where ^ indicates the scissile bond, identified by MS analysis) was purchased from Bachem AG (Bubendorf, Switzerland), and kept as a 5 mM stock solution in DMSO at −20° C. All other chemicals were of analytical grade.

Enzymatic reactions were conducted in 100 mM Tris/HCl buffer at pH 7.5, containing 500 mM NaCl, and 0.05% (w/v) CHAPS.

All protein and peptide containing solutions are handled in siliconized tubes (Life Systems Design, Merenschwand, Switzerland).

The compound solutions as well as the enzyme and the substrate solutions are transferred to the 384-well plates (black Cliniplate; cat. no. 95040020 Labsystems Oy, Finland) by means of a CyBi-Well 96-channel pipettor (CyBio AG, Jena, Germany).

Instrumentation for FI Measurements

For fluorescence intensity (FI) measurements an Ultra Evolution reader (TECAN, Maennedorf, Switzerland) is used. The instrument is equipped with a combination of a 350 nm (20 nm bandwidth) and a 500 nm (25 nm bandwidth) bandpass filter for fluorescence excitation and emission acquisition, respectively. To increase the signal:background ratio, an appropriate dichroic mirror is employed. The optical filters and the dichroic mirror are purchased from TECAN. The fluorophores in each well are excited by three flashes per measurement.

The cyclic depsipeptides inhibited human neutrophile elastase with IC50 values as indicated in table 11.

In addition the cyclic depsipeptides inhibited human chymotrypsin with an IC50 ranging from 0.001 µM to 0.02 µM.

The biological activity of the cyclic depsipeptide according to formula (VIII) was determined with kallikrein 7. This cyclic depsipeptide of the invention inhibits human kallikrein 7 with an $IC_{50}$ of less than 3 nM. This cyclic depsipeptide inhibited human chymotrypsin and human neutrophile elastase with an IC50 around 0.004 µM and around 0.0025 µM, respectively.

Example 3

Determination of Kallikrein-7 Inhibitory Activity In Vivo

A) Test on Recovery of Skin Barrier Disruption in Mice

Method: Skin barrier disruption was achieved in groups of hairless SKH1 mice with repeated stripping of the skin with S-Sqame® skin sampling disks. The procedure was completed when transepidermal water loss (TEWL) achieved ≥40 mg/cm²/h. TEWL was assessed with a Tewameter TM210 (Courage Khazaka, Cologne, Del.). Immediately after barrier disruption 30 µl the test compound was applied at 10 mM concentration. Control animals were treated similarly with the solvent (ethanol/propylene glycol, 3/7 (v/v)) alone. TEWL was measured before, immediately after, and at 3 hrs after barrier disruption. In each animal, the percentage recovery was calculated using the formula: (1−[TEWL at 3 hrs−base line TEWL]/[TEWL immediately after stripping−base line TEWL])×100%.

Results:

A single application of the test compound (the Cyclic depsipeptide according to formula II) accelerated barrier repair by 57% compared to repair in mice treated with the solvent alone (p<0.05), Table 12.

TABLE 12

| Animals | % Recovery in barrier disruption Mean (SD values), n: 4 animals per group) |
|---|---|
| Treated with test compound (the Cyclic depsipeptide according to formula II) at 10 mM | 72.0 (9.1) |
| Treated with solvent alone | 45.8 (8.0) |

B) Test on Anti-Inflammatory Activity in Murine Model of Allergic Contact Dermatitis (ACD)

Method: Crl:NMRI mice were sensitized on the shaved abdomen with 50 µl of 2% oxazolone on day 1 and challenged with 10 µl oxazolone on the inner surface of the right ear on day 8. The unchallenged left ears served as normal controls and dermatitis was evaluated from the difference in auricular weight (taken as a measure of inflammatory swelling) on day 9. The animals were treated topically with 10 µl test compound or the solvent only 30 min after the challenge. The efficacy of the treatment was calculated as the percentage inhibition of inflammatory auricular swelling relative to animals treated with the vehicle alone.

Results: A single application of the test compound (the Cyclic depsipeptide according to formula II) inhibited inflammatory swelling in ACD by 40% at 10 mM) and by 46% at 30 mM concentration (p<0.001 vs solvent-treated animals (Table 13/14).

TABLE 13

| Animals | Δ Auricular weights Mean (SD), n: 8 animals per group | % Inhibition of inflammatory swelling Mean ± SE |
|---|---|---|
| Treated with test compound (the Cyclic depsipeptide according to formula II) at 30 mM | 15.3 (5.4) | 46 ± 7.5 |
| Treated with test compound (the Cyclic depsipeptide according to formula II) at 10 mM | 17.0 (4.8) | 40 ± 6.9 |
| Treated with solvent[+] alone | 28.1 (4.6) | — |

[+] mixture of dimethylacetamide/ethanol/acetone (1/2/2)

TABLE 14

| Compound according to formula | % Inhibition of inflammatory swelling concentration of test compound 30 mM | % Inhibition of inflammatory swelling concentration of test compound 10 mM |
|---|---|---|
| example 9 | 38 | 42 |
| example 10 | 25 | 22 |
| example 23 | 40 | 48 |
| example 25 | 38 | 39 |
| example 43 | 55 | 42 |

C) Test on Anti-Inflammatory Activity in Swine Model of Allergic Contact Dermatitis (ACD)

Eight days before the elicitation of the ACD, 500 µl of 10% 2,4-dinitrofluorobenzene (DNFB, dissolved in DMSO/acetone/olive oil [1/5/3, v/v/v]) were applied epicutaneously in divided volumes onto the basis of both ears and onto both groins (100 µl/site) for sensitization. The challenge reactions were elicited with 15 µl of DNFB (1.0%) on contralateral test sites (each 7 cm² in size) of the shaved dorsolateral back. For treatment, the test compound and the placebo (solvent only) were applied contralaterally to 2 test sites in each animal 0.5 and 6 hrs after the challenge. The test sites were clinically examined 24 hrs after the challenge when inflammation peaked. The changes were scored on a scale from 0 to 4 (Table 15), allowing a combined maximal score of 12 per designated site. Skin reddening was measured reflectometrically using a* values.

TABLE 15

Scoring of clinical signs of test sites affected with ACD

| Score | Erythema/ Intensity | Erythema/ Extent | Induration |
|---|---|---|---|
| 0 | absent | absent | absent |
| 1 | scarcely visible | small spotted | scarcely palpable |
| 2 | mild | large spotted | mild hardening |
| 3 | pronounced | confluent | pronounced hardening |
| 4 | severe (or livid discoloring) | homogenous redness | pronounced and elevated hardening |

Results: Treatment of test sites affected with ACD twice with a 1% solution of the test compound (the Cyclic depsipeptide according to formula II) inhibited clinical inflammatory changes by 30% (p<0.01) and measured skin redness by 27% (p<0.05) (Table 16)

TABLE 16

| Test sites | Clinical score (Mean, SD, n: 8+) | A* value (Mean, SD, n: 8+) |
|---|---|---|
| Treated with 1% test compound (the Cyclic depsipeptide according to formula II) | 5.1 (1.7) | 8.6 (1.4) |
| Treated with placebo (solvent) | 7.2 (1.9) | 12.0 (2.5) |
| Inhibition vs placebo-treated sites | 29.9 (11.7) | 27.0 (2.5) |

+2 test sites each in 4 animals

Example 4

Derivatisation of a Cyclic Depsipeptide of the Invention a) One-step procedure: To a solution of 20 mg of cyclic depsipeptide according to formula (II) and 0.027 mL triethylsilane in 2 mL of dichloromethane/acetonitrile (1:1) at −50° C. 0.014 mL of boron trifluoride etherate were slowly added. The reaction mixture was allowed to warm up to −5° C. and kept at this temperature for additional 30 minutes, poured into a saturated NaHCO₃ solution, and was extracted with EtOAc. The organic layer was dried over sodium sulfate and the solvent was removed in vacuo. Purification of the residue obtained by HPLC(XTerra [5 cm]; acetonitrile/ammonium carbonate buffer pH10 gradient) provided 9.8 mg of a derivative of the cyclic depsipeptide according to formula (II) wherein the Ahp has been converted into 3-amino-piperidin-2-one. ESI MS: 935.36 [M+Na]⁺.

b) Two-step procedure: To a solution of 1 g of cyclic depsipeptide according to formula (II) in 300 mL of dichloromethane/acetonitrile (1:1) at −50° C. 0.68 mL of boron trifluoride etherate were slowly added. The reaction mixture was allowed to warm up to −20° C. Then additional 0.68 mL of boron trifluoride etherate were slowly added the reaction mixture kept at this temperature until no more starting material could be observed (HPLC). Then the reaction mixture was poured into a saturated NaHCO₃ solution, and was extracted with EtOAc. The organic layer was dried over sodium sulfate and the solvent was removed in vacuo providing a derivative of the cyclic depsipeptide according to formula (II) wherein the Ahp has been converted into 3-amino-3,4-dihydro-1H-pyridin-2-one. ESI MS: 933.28 [M+Na]⁺.

The crude material was dissolved in 400 mL of 2-propanol, 115 mg of Pd/C (10%) were added and the mixture was hydrogenated under atmospheric pressure until the starting material was consumed (HPLC). The residue obtained was purified by chromatography (SiO₂; cHex/EtOAc (1:1)+10% MeOH) providing 684 mg of the cyclic depsipeptide according to formula (II) wherein the Ahp has been converted into 3-amino-piperidine-2-one.

Example 5

Derivatisation of a Cyclic Depsipeptide of the Invention

To a solution of 75 mg (0.081 mmol) of cyclic depsipeptide according to formula (II) in 5 mL of 1-PrOH 30 µL of sulfuric acid were added and the reaction mixture was stirred at r.t. for 48 hours. For workup the reaction mixture was diluted with dichloromethane and washed with sat. bicarbonate solution. After drying of the organic layer over sodium sulfate the solvent was removed and the residue obtained purified by chromatography on silica gel (cHex/EtOAc (1:1)+10%

MeOH). Yield: 65 mg (83%) of a derivative of the cyclic depsipeptide according to formula (II) wherein the Ahp has been converted into 3-amino-6-propoxy-piperidin-2-one. ESI MS: 993.37 [M+Na]+.

Similarly, treatment with the corresponding alcohol provided the following compounds:

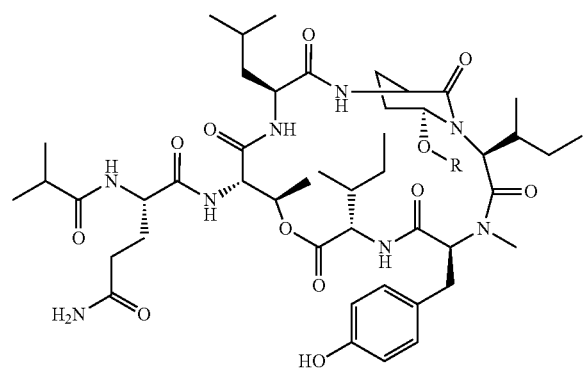

TABLE 17

| Example | R | ESI MS [M + Na]+ |
|---|---|---|
| 6 | 1-octyl | 1063.41 |
| 7 | 2,2,2-trifluoroethyl | 1033.30 |
| 8 | 2-propyl | 993.43 |
| 9 | benzyl | 1041.16 |
| 10 | ethyl | 979.22 |
| 11 | 1-butyl | 1007.29 |
| 12 | isobutyl | 1007.35 |
| 13 | 2-methoxyethyl | 1009.31 |
| 14 | 2-hydroxyethyl | 995.28 |
| 15 | 2-(2-hydroxyethoxypethyl | 1039.31 |
| 16 | 2-(2-methoxyethoxy)ethyl | 1053.33 |
| 17 | methyl | 965.27 |
| 18 | propargyl | 989.21 |

Simultaneously, compounds of the following type were obtained under the same conditions:

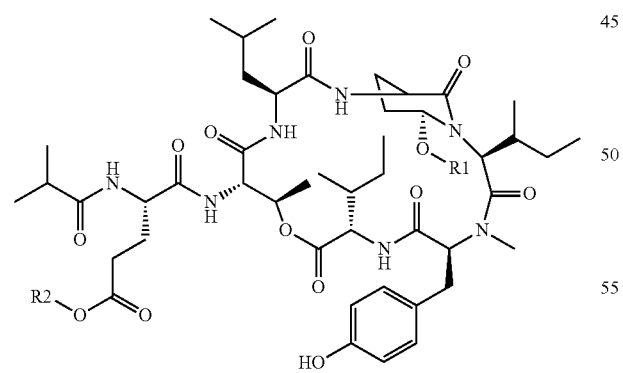

TABLE 18

| Example | R1, R2 | ESI MS [M + Na]+ |
|---|---|---|
| 19 | 1-propyl | 1136.33 |
| 20 | methyl | 980.21 |

Example 21

Derivatisation of a Cyclic Depsipeptide of the Invention

A solution of 25 mg (0.027 mmol) of cyclic depsipeptide according to formula (II) in 2 mL of dichloromethane was cooled to 0° C. Then DIPEA and trifluoroacetic acid anhydride (TFAA) was added. The reaction mixture was slowly warmed up to room temperature and stirred for additional 4 hours. For workup the reaction mixture was diluted with dichloromethane and washed with hydrochloric acid and sat. bicarbonate solution. After drying over sodium sulfate the solvent was removed and the residue obtained purified by chromatography on silica gel (cHex/EtOAc (1:1)+10% MeOH). Yield: 14 mg (57%) of a derivative of the cyclic depsipeptide according to formula (II) wherein the amide in the sidechain of A1 has been converted into a nitrile. ESI MS: 933.30 [M+Na]+.

Similarly, compounds of the following type was obtained:

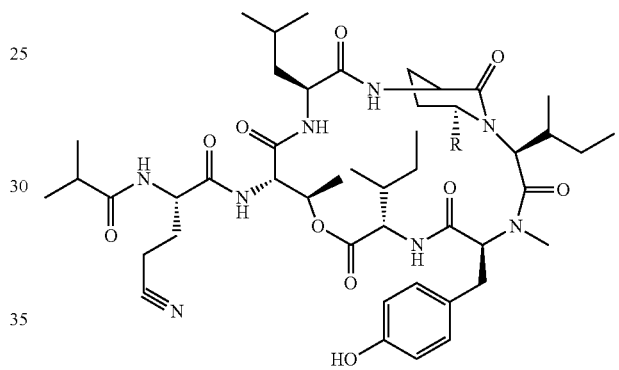

TABLE 19

| Example | R | ESI MS [M + Na]+ |
|---|---|---|
| 22 | H | 917.30 |
| 23 | ethyl | 961.20 |
| 24 | 1-propyl | 975.29 |
| 25 | benzyl | 1023.14 |

Example 26

Derivatisation of a Cyclic Depsipeptide of the Invention

A solution of 25 mg (0.027 mmol) of a cyclic depsipeptide according to formula (II) in 2 mL of dichloromethane (MC) was cooled to 0° C. Then 24 µL of DIPEA and 14 µL of hexyl chloroformate was slowly added. The reaction mixture was allowed to warm up to rt and stirred for additional 4 hours. For workup the reaction mixture was diluted with dichloromethane and washed with hydrochloric acid and sat. bicarbonate solution, and brine. After drying over sodium sulfate the solvent was removed and the residue obtained purified by chromatography on silica gel (cHex/EtOAc (1:1)+10% MeOH). Yield: 20 mg (70%) of a derivative of the cyclic depsipeptide according to formula (II) wherein the phenol moiety of A6 has been transformed into the corresponding carbonic acid hexyl ester. ESI MS: 1079.41 [M+Na]+.

Analogously, using a compound described in Example 4 as starting material the following compounds were obtained:

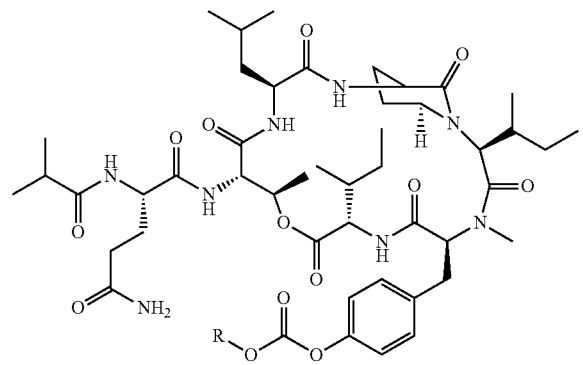

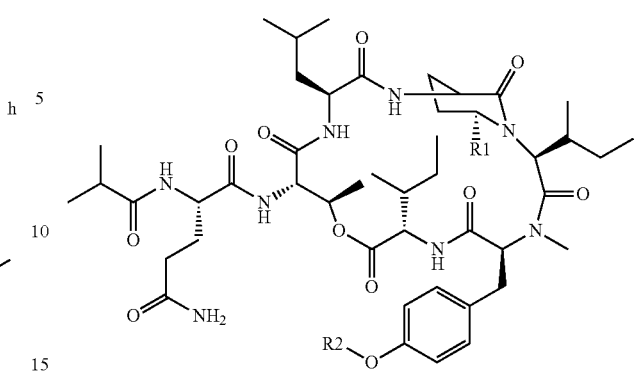

TABLE 20

| Example | R | ESI MS [M + Na]+ |
|---|---|---|
| 27 | isobutyl | 1035.38 |
| 28 | 2-methoxyethyl | 1037.36 |
| 29 | ethyl | 1007.35 |
| 30 | (steroid structure) | 1347.63 |
| 31 | 1-octyl | 1091.42 |

TABLE 21

| Example | R1 | R2 | ESI MS [M + Na]+ |
|---|---|---|---|
| 33 | H | t-buthoxycarbonylnethyl | 1049.33 |
| 34 | propoxy | t-buthoxycarbonylmethyl | 1107.33 |
| 35 | propoxy | 1-(E)-pent-2-enyl | 1061.36 |
| 36 | propoxy | 1-(E)-4,4,4-trifluoro-but-2-enyl | 1101.25 |
| 37 | propoxy | methyl | 1007.29 |
| 38 | propoxy | 3-methyl-but-2-enyl | 1061.36 |
| 39 | propoxy | benzyl | 1083.38 |
| 40 | propoxy | allyl | 1033.37 |
| 41 | propoxy | propargyl | 1031.25 |

Example 32

Derivatisation of a Cyclic Depsipeptide of the Invention

To a mixture of 200 mg (0.21 mmol) of cyclic depsipeptide according Example 5, 57.5 mg (0.41 mmol) of $K_2CO_3$ in 2 mL of dry acetone 60.5 mg (0.31 mmol) of (E)-3-phenyl-2-propenyl bromide was added and treated with ultrasound overnight (temperature raises to about 50° C.). For workup the reaction mixture was diluted with dichloromethane and washed with water. After drying of the organic layer over sodium sulfate the solvent was removed and the residue obtained purified by HPLC (15 cm Zorbax; acetonitrile/aqu. $NH_4OAc$ buffer: 20→95%). Yield: 100 mg (45%) of a derivative of cyclic depsipeptide according Example 5 featuring O-((E)-3-phenyl-2-propen-1-yl)-L-tyrosine in A6. ESI MS: 1109.37 [M+Na]+.

Analogously, treatment of cyclic depsipeptides according Example 4 or 5 with the appropriate alkylating agent provide the following compounds:

Example 42

Derivatisation of a Cyclic Depsipeptide of the Invention

To a mixture of 200 mg (0.21 mmol) of cyclic depsipeptide according Example 5, 46.5 mg (0.31 mmol) of sodium iodide, and 57.5 mg (0.41 mmol) of $K_2CO_3$ in 2 mL of dry acetone 44 mg (0.31 mmol) of 3-(chloromethyl)-1,5-dimethyl-1H-pyrazole was added and treated with ultrasound overnight (temperature raises to about 50° C.). For workup the reaction mixture was diluted with dichloromethane and washed with water. After drying of the organic layer over sodium sulfate the solvent was removed and the residue obtained purified by HPLC (15 cm Zorbax; acetonitrile/aqu. $NH_4OAc$ buffer: 20→95%). Yield: 90 mg (40.5%) of a derivative of cyclic depsipeptide according Example 5 featuring O-(1,5-dimethyl-1H-pyrazol-3-yl)methyl-L-tyrosine in A6. ESI MS: 1101.39 [M+Na]+.

Example 43

Analogously, treatment of cyclic depsipeptide of cyclic depsipeptide according to formula (II) with 3-(chloromethyl)-1,5-dimethyl-1H-pyrazole provides a compound featuring O-(1,5-dimethyl-1H-pyrazol-3-yl)methyl-L-tyrosine in A6. ESI MS: 1059.19 [M+Na]+.

Example 44

Derivatisation of a Cyclic Depsipeptide of the Invention

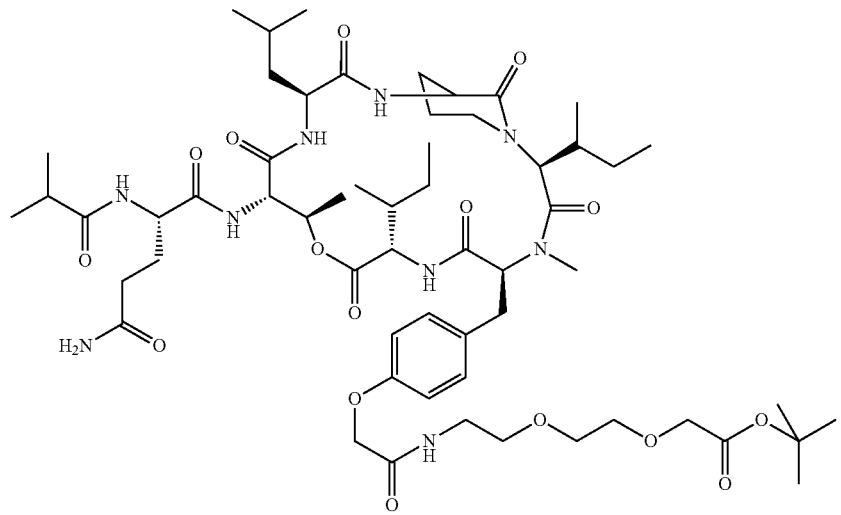 [SMILES: CCC(C)[C@@H]1NC(=O)[C@H](Cc2ccc(OCC(=O)NCCOCCOCC(=O)OC(C)(C)C)cc2)N(C)C(=O)[C@H](C(C)CC)N2CCCC(NC(=O)[C@H](CC(C)C)NC(=O)[C@@H](NC(=O)[C@H](CCC(N)=O)NC(=O)C(C)C)[C@@H](C)OC1=O)C2=O]

To a solution of 17 mg (0.0165 mmol) of cyclic depsipeptide according Example 33 in 2 mL of dichloromethane 845 µL of trifluoroacetic acid was added and stirred at r.t. for 4 hours. The reaction mixture was diluted with toluene and the solvent was removed in vacuo providing 22.5 mg of the corresponding crude acid.

20 mg of the aforementioned acid, 6.81 mg (0.031 mmol) of 8-amino-3,6-dioxaoctanoic acid tert-butylester, and 15.8 mg (0.041 mmol) of HATU were dissolved in 2 mL of dry DMF and 11 µL of DIEPA were added and stirred at r.t. overnight. For workup, the reaction mixture was diluted with EtOAc and washed with sat. NaHSO$_4$ and NaHCO$_3$ solutions and brine. After drying of the organic layer over sodium sulfate the solvent was removed and the residue obtained purified by HPLC (15 cm Zorbax; acetonitrile/aqu. NH$_4$OAc buffer: 20→95%). Yield: 7 mg (29%) of the title compound. ESI MS: 1194.32 [M+Na]$^+$.

8-Amino-3,6-dioxaoctanoic acid tert-butylester 100 mg (0.226 mmol) of 8-(9-Fluorenylmethoxycarbonylamino)-3,6-dioxaoctanoic acid tert-butylester in 1 mL of dry DMF were treated with piperidine (89.5 µL; 0.862 mmol) at r.t. for 3 hours. The solvent was evaporated and the residue purified by chromatography on silica gel with a gradient cHex→EtOAc→EtOAc/MeOH (1:1)+3%. MeOH. Yield: 12 mg (24%) of the title compound. ESI MS: 220.08 [M+H]$^+$.

8-(9-Fluorenylmethoxycarbonylamino)-3,6-dioxaoctanoic acid tert-butylester

A solution of 150 mg (0.389 mmol) of 8-(9-Fluorenylmethoxycarbonylamino)-3,6-dioxaoctanoic acid, 546 mg (9.73 mmol) isobutylene, and 4.3 µL of 95-98% H$_2$SO$_4$ was stirred at r.t. for 3 days. For workup the reaction solution was diluted with dichloromethane and washed with sat. bicarbonate solution. After drying over sodium sulfate the solvent was removed and the residue obtained purified by chromatography on silica gel with a cHex/EtOAc gradient providing 145 mg (84.4%) of the title compound. ESI MS: 464.12 [M+Na]$^+$.

Example 45

Derivatisation of a Cyclic Depsipeptide of the Invention

To a mixture of 101 mg (0.1 mmol) of a compound of Example 41 and 40 mg CuI in 11 ml of toluene/DMF (10:1) 50 L of DIEPA and 1 mL of a 1M solution of 1-azido-2-[2-(2-azido-ethoxy)-ethoxy]-ethane was added and stirred at 45° C. for 6 hours. Then the reaction mixture was washed with a sat. NaH$_2$PO$_4$ solution, dried over sodium sulfate, and the solvent was evaporated. The residue obtained was purified by chromatography (SiO$_2$; cHex/EtOAc (1:1)+20% MeOH) providing 14 mg (11.7%) of the title compound. ESI MS: 1231.34 [M+Na]$^+$.

Example 46

Derivatisation of a Cyclic Depsipeptide of the Invention

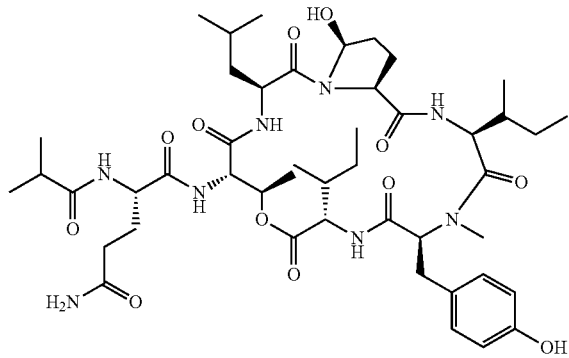 [SMILES: CCC(C)[C@@H]1NC(=O)[C@H](Cc2ccc(O)cc2)N(C)C(=O)[C@H](C(C)CC)NC(=O)[C@@H]2CC[C@H](O)N2C(=O)[C@H](CC(C)C)NC(=O)[C@@H](NC(=O)[C@H](CCC(N)=O)NC(=O)C(C)C)[C@@H](C)OC1=O]

A solution of 25 mg of depsipeptide according to formula (II) in 25 mL water was stirred at room temperature. In this solution an additional peak was observed in HPLC analysis, which forms an equilibrium with the depsipeptide according to formula (II). After 20 days the solution was dried using lyophilization and the additional peak was isolated using reversed phase chromatography as described in example 1. This provided 0.75 mg cyclic depsipeptide according to example 46, wherein Ahp has been converted into 5-hydroxyproline.

ESI-MS: pos. mode: m/z=951.5 (M+Na), neg. Mode: m/z=927.4 (M−H); monoisotopic MW 928.5, $C_{46}H_{72}N_8O_{12}$ $^1$H NMR (600 MHz) $d_5$-DMSO $\delta_H$: 0.00 (1H, m), 0.50 (3H, t, J=7.3 Hz), 0.71 (3H, m), 0.76 (3H, t, J=7.0 Hz), 0.76 (3H, d, J=7.3 Hz), 0.85 (6H, d, J=6.6 Hz), 0.88 (1H, m), 1.00 (1H, m), 1.03 (3H, d, J=6.6 Hz), 1.06 (6H, d, J=6.6 Hz), 1.10 (1H, m), 1.16 (1H, m), 1.26 (1H, m), 1.36 (1H, m), 1.43 (1H, m), 1.51 (2H, m), 1.79 (1H, m), 1.83 (1H, m), 1.97 (1H, m), 1.99 (1H, m), 2.17 (2H, t, J=7.7 Hz), 2.39 (1H, m), 2.48 (1H, m), 2.67 (3H, s), 2.78 (1H, m), 3.43 (1H, m), 4.32 (1H, m), 4.33 (1H, m), 4.45 (1H, m), 4.48 (1H, m), 4.58 (1H, m), 4.61 (1H, m), 4.67 (1H, m), 5.09 (1H, m), 5.47 (1H, m), 6.66 (2H, d, J=8.1 Hz), 6.74 (1H, s, broad), 7.03 (2H, d, J=8.1 Hz), 7.31 (1H, s, broad), 7.33 (1H, d, J=9.5 Hz), 8.04 (1H, d, J=9.5 Hz), 8.17 (1H, d, J=8.1 Hz), 8.23 (1H, d, J=2.9 Hz), 8.43 (1H, d, J=9.5 Hz), 9.25 (1H, s, broad), (OH group of hydroxyproline not visible).

Example 47

Derivatisation of a Cyclic Depsipeptide of the Invention

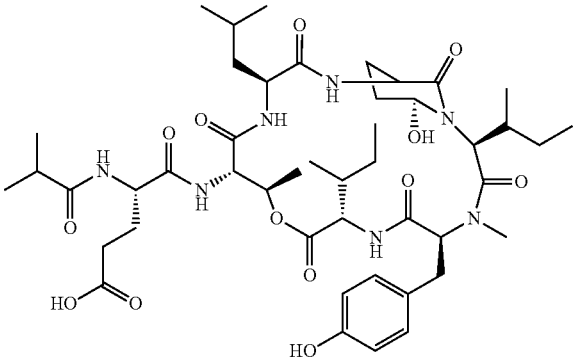 [SMILES: CCC(C)[C@@H]1NC(=O)[C@H](Cc2ccc(O)cc2)N(C)C(=O)[C@H](C(C)CC)N2C(=O)C(CC[C@@H]2O)NC(=O)[C@H](CC(C)C)NC(=O)[C@@H](NC(=O)[C@H](CCC(=O)O)NC(=O)C(C)C)[C@@H](C)OC1=O]

A solution of 100 mg of depsipeptide according to formula (II) in 25 mL 0.5 N HCl was stirred at 50° C. for 24 h. For workup the pH of the reaction mixture was adjusted to pH 7 with 5 N NaOH and was extracted with ethyl acetate. The organic layer was dried over sodium sulfate and the solvent was removed in vacuo. The residue obtained was purified by reversed phase chromatography (same conditions as described example 1) providing 17 mg of cyclic depsipeptide according to example 47, wherein glutamine in A1 has been replaced by glutamic acid.

ESI-MS: pos. mode: m/z=952.8 (M+Na), neg. Mode: m/z=928.5 (M−H); monoisotopic MW 929.5, $C_{46}H_{71}N_7O_{13}$ $^1$H NMR (600 MHz, $d_6$-DMSO) $\delta_H$: −0.11 (3H, d, J=6.6 Hz), 0.64 (4H, m), 0.77 (3H, d, J=6.6 Hz), 0.81 (3H, t, J=7.3 Hz), 0.84 (3H, d, J=6.6 Hz), 0.88 (3H, d, J=6.6 Hz), 1.02 (6H, m), 1.05 (1H, m), 1.10 (1H, m), 1.19 (3H, d, J=5.9 Hz), 1.24 (1H, m), 1.40 (1H, m), 1.51 (1H, m), 1.75 (1H, m), 1.78 (5H, m), 1.85 (2H, m), 2.10 (2H, m), 2.45 (1H, m), 2.60 (1H, m), 2.67 (1H, m), 2.71 (3H, s), 3.20 (1H, m), 4.28 (1H, m), 4.29 (1H, m), 4.44 (2H, m), 4.63 (1H, d, J=9.5 Hz), 4.69 (1H, m), 4.93 (1H, m), 5.04 (1H, m), 5.47 (1H, m), 6.24 (1H, s, broad), 6.64 (2H, d, J=8.8), 6.99 (2H, d, J=8.8 Hz), 7.37 (1H, d, J=9.5 Hz), 7.69 (1H, d, J=9.5 Hz), 7.80 (1H, d, J=9.5 Hz), 8.51 (1H, d, J=8.8 Hz), 8.57 (1H, d, J=5.1 Hz), OH group of Tyrosine and glutamic acid not visible)

REFERENCES

[Bode H B, Zeggel B, Silakowski B, Wenzel S C, Reichenbach H, Müller R (2003)] Steroid biosynthesis in prokaryotes: identification of myxobacterial steroids and cloning of the first bacterial 2,3(S)-oxidosqualene cyclase from the myxobacterium *Stigmatella aurantiaca*. Mol Microbiol 47:471-481

[Das S K, Mishra A K, Tindall B J, Rainey F A, Stackebrandt E (1996)] Oxidation fo thiosulfate by a new bacterium, *Bosea thiooxidans* (strain BI-42) gen. nov., sp. nov.: Analysis of phylogeny based on chemotaxonomy and 16S ribosomal DNA sequencing. hit J Syst Bacteriol 46:981-987

[Dictionary of Natural Products (2007)] Dictionary of Natural products on CD-ROM, version 15.2, 2007, Hampen Data services Ltd.

[DSMZ (2007)] Description of biological risk group fo *Chondromyces* strains available on the website http://www.dsmz.de/

[Gerth K, Pradell A, Perlova O, et al. (2003)] Myxobacteria: proficient producers fo novel natural products with various biological activities—past and future biotechnological aspects with the focus on the genus *Sorangiurn*. J Biotechnol 106:233-253

[Hansson L, Backman A, Ny A, Edlund M, Ekholm E, Ekstrand Hammarstrom B, Tornell J, Wallbrandt P, Wennbo F L Egelrud T (2002)] Epidermal overexpression of stratum corneum chymotryptic enzyme in mice: a model for chronic itchy dermatitis. J Invest Dermatol 118:444-449

[Ishida K, Matsuda H, Murakami Ni, Yamaguchi K (1996)] The Absolute Stereochemistry of micropeptin 90. Tetrahedron letters 37:51-52.

[Jacobi C A, Reichenback F L Tindall B J, Stackebrandt E (1996)] "*Candidatus* comitans," a bacterium living in cocculture with *Chondromyces crocatus* (Myxobacteria). Int J Syst Bacteriol 46:119-122

[Jacobi C A, Assmus B, Reichenbach F L Stackebrandt E (1997)] Molecular evidence for association between the Sphingobacterium-like organism "*Candidatus* comitans"

and the myxobacterium *Chondromyces crocatus*. Appl Environ Microbiol 63:719-723

[Jansen R, Kunse B, Reichenbach H, Höfle G (2002)] The ajudazols A and B, novel isochromanones from *Chondromyces crocatus* (Myxobacteria): Isolation and structure elucidation. Eur J Org Chem 2002:917-921

[Kaiser D (2003)] Coupling cell movement to multicellular development in myxobacteria. Nature Reviews Micobiol 1:45-54

[Kunze B, Jansen R, Sasse F, et al. (1995)] Chondramides A~D, new antifungal and cytostatic depsipeptides from *Chondromyces crocatus* (Myxobacteria): Production, physicochemical and biological properties. J Antibiotics 48:1262-1266

[La Scola B, Mallet M-N, Grimont P A D, Raoult D (2003)] *Bosea eneae* sp. nov., *Bosea massiliensis* sp. nov. and *Bosea vestrisii* sp. nov., isolated from hospital water supplies, and emendation of the genus *Bosea* (Das et al. 1996). Int J Syst Evol Microbiol 53:15-20

[Lee A Y, Smitka T A, Bonjouklian R, Clardy J (1994)] Atomic structure of the trypsin-A90720A complex: a unified approach to structure and function. Chemistry & Biology 1:113-117

[Matern U, Schleberger C, Jelakovic S, Weckesser J, Schulz G E (2003)] Binding structure of elastase inhibitor scyptolin A Chemistry & Biology 10:997-1001

[Rahid S, et al. (2006)] Molecular and biochemical studies of chondramide formation—highly cytotoxic natural products from *Chondromyces crocatus* Cm c5. Chem & Biol 14:667-681

[Rouhiainen L, Paulin L, Suomalainen S, Hyytiäinen H, Buikema W, Haselkorn R, Sivonen K (2000)] Genes encoding for synthetases of cyclic depsipetides, anabaenopeptilides, in Anabaena strain 90. Molecular Microbiology 37:156-167.

[Vasilopoulos Y, Cork M J, Murphy R, et al. (2004)] Genetic association between an AACC insertion in the 3'UTR of the stratum corneum chymotryptic enzyme gene and atopic dermatitis. J Invest Dermatol 123:62-66

The invention claimed is:

1. A method of treating a subject suffering from psoriasis comprising administering to said subject a therapeutically effective amount of a cyclic depsipeptide, having the structure of formula (I):

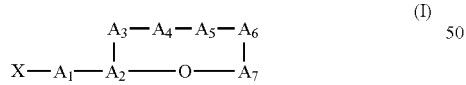

wherein an ester bond is formed between the carboxy group of $A_7$ and the hydroxy group of $A_2$,
wherein X and $A_1$ are each independently optional,
and wherein
X is H or an amino group modifying moiety selected from an aryl carbonyl residue or from an acyl residue,
$A_1$ is glutamine, ornithine, glutamic acid or a derivative thereof selected from glutamic nitrile, glutamic acid $C_{1-12}$alkyl ester or glutamic acid $C_{6-24}$aryl ester;
$A_2$ is threonine or serine,
$A_3$ is leucine,
$A_4$ is Ahp, 3-amino-piperidine-2-one, dehydro-AHP, Ahp-I, Ahp-II, proline, 5-hydroxy-proline, wherein the point of fusion (with $A_3$ and $A_5$) are at the nitrogen atom and the carboxyl oxygen (by virtue of the replacement of a hydrogen atom by a bond) of the proline, and 5-hydroxyproline,
wherein Ahp, 3-amino-piperidine-2-one, dehydro-AHP, Ahp-I, and Ahp-II, are as defined below, and wherein the points of fusion (with $A_3$ and $A_5$) are at the nitrogen atoms of the said compounds (by virtue of the replacement of a hydrogen atom by a bond):

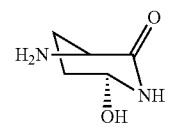

3-amino-6-hydroxy-piperidin-2-one (Ahp)

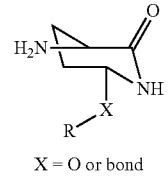

X = O or bond

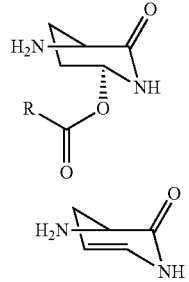

3-amino-3,4-dihydro-1H-pyridin-2-one (dehydro-AHP)

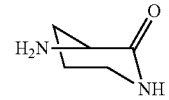

3-amino-piperidine-2-one wherein X is O or a bond, and R is an organic moiety or is a radical selected from the group consisting of hydrogen, $(C_{1-12})$alkyl, $(C_{2-12})$alkenyl, $(C_{2-12})$alkynyl, halo$(C_{1-12})$alkyl, halo$(C_{2-12})$ alkenyl, halo$(C_{2-12})$alkynyl, $(C_{1-12})$alkoxycarbonyl, $(C_{1-12})$alkoxy-carbonyl$(C_{1-12})$alkyl, $(C_{1-12})$ alkylaminocarbonyl, unsubstituted or further substituted by aryl, arylalkyl, arylalkenyl or arylalkynyl, heterocyclyl and heterocyclylalkyl, $A_5$ is isoleucine, phenylalanine or valine, $A_6$ is tyrosine, N-Me-tyrosine or a derivative thereof selected from N-Me-tyrosine where the OH group of the tyrosine or N-Me-tyrosine is OR, wherein R is selected from the group consisting of $(C_{1-12})$alkyl, $(C_{2-12})$alkenyl, $(C_{2-12})$alkynyl, halo$(C_{1-12})$alkyl, halo$(C_{2-12})$alkenyl, halo$(C_{2-12})$alkynyl, $(C_{1-12})$alkoxycarbonyl, $(C_{1-12})$alkoxy-carbonyl$(C_{1-12})$alkyl, $(C_{1-12})$ alkylaminocarbonyl, wherein the alkyl, alkenyl and alkinyl moieties of groups R can be unsubstituted or further substituted by aryl, aryl$(C_{1-6})$alkyl, aryl$(C_{2-12})$alkenyl or aryl $(C_{2-12})$ alkynyl, heterocyclyl and heterocyclyl$(C_{1-12})$ alkyl, $A_7$ is leucine, isoleucine or valine, or a pharmaceutically acceptable salt thereof.

2. The method of claim 1 wherein X is CH$_3$CH$_2$CH(CH$_3$)CO, (CH$_3$)$_2$CHCH$_2$CO, (CH$_3$)$_2$CHCO, CH$_3$CO or Phenyl-CO, or a pharmaceutically acceptable salt thereof.

3. The method of claim 1 wherein the nitrogen atom of the amide bond between A5 and A6 is substituted with a methyl and the OH group of the tyrosine is OR, wherein R is selected from the group consisting of hydrogen, (C$_{1-12}$)alkyl, (C$_{2-12}$)alkenyl, (C$_{2-12}$)alkynyl, halo(C$_{1-12}$)alkyl, halo(C$_{2-12}$)alkenyl, halo(C$_{2-12}$)alkynyl, (C$_{1-12}$)alkoxycarbonyl, (C$_{1-12}$)alkoxycarbonyl(C$_{1-12}$)alkyl, (C$_{1-12}$)alkylaminocarbonyl, unsubstituted or further substituted by aryl, arylalkyl, arylalkenyl or arylalkynyl, heterocyclyl and heterocyclylalkyl, or a pharmaceutically acceptable salt thereof.

4. The method of claim 1 wherein A4 is the Ahp derivative 3-amino-piperidin-2-one, Ahp-I or Ahp-II, wherein R is selected from the group consisting of of (C$_{1-12}$)alkyl, (C$_{2-12}$)al-kenyl, (C$_{2-12}$)alkynyl, halo(C$_{1-12}$)alkyl, (C$_{1-12}$)alkoxy(C$_{1-12}$)alkyl, (C$_{1-12}$)alkoxy(C$_{1-12}$)alkoxy(C$_{1-12}$)alkyl, hydroxy(C$_{1-12}$)alkyl, phenyl and phenyl(C$_{1-6}$)alkyl, or a pharmaceutically acceptable salt thereof.

5. The method of claim 1 wherein the acyl residue X is CH$_3$CH$_2$CH(CH$_3$)CO
or (CH$_3$)$_2$CHCO,
A$_1$ is glutamine, glutamic acid, or a derivative thereof selected from glutamic nitrile, glutamic acid C$_{1-12}$alkyl ester or glutamic acid C$_{6-24}$aryl ester,
A$_2$ is threonine,
A$_3$ is leucine,
A$_4$ is Ahp, 3-amino-piperidine-2-one, proline, 5-hydroxy-proline,
A$_5$ is isoleucine,
A$_6$ is tyrosine, N-Me-tyrosine or a derivative thereof selected from N-Me-tyrosine where the OH group of the tyrosine or N-Me-tyrosine is OR, wherein R is selected from the group consisting of (C$_{1-12}$)alkyl, (C$_{2-12}$)alkenyl, (C$_{2-12}$)alkynyl, halo(C$_{1-12}$)alkyl, halo(C$_{2-12}$)alkenyl, halo(C$_{2-12}$)alkynyl, (C$_{1-12}$)alkoxycarbonyl, (C$_{1-12}$)alkoxy-carbonyl(C$_{1-12}$)alkyl, (C$_{1-12}$) alkylaminocarbonyl, wherein the alkyl, alkenyl and alkinyl moieties of groups R can be unsubstituted or further substituted by aryl, aryl(C$_{1-6}$)alkyl, aryl(C$_{2-12}$)alkenyl or aryl (C$_{2-12}$) alkynyl, heterocyclyl and heterocyclyl(C$_{1-12}$)alkyl,
A$_7$ is isoleucine or valine, or a pharmaceutically acceptable salt thereof.

6. The method of claim 1 wherein A$_4$ is Ahp, Ahp-I, 3-amino-piperidine-2-one, proline, or 5-hydroxy-proline, or a pharmaceutically acceptable salt thereof.

7. The method of claim 1, wherein the cyclic depsipeptide is a compound in accordance with formulae A or B,

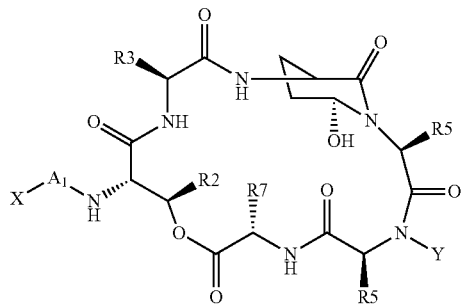

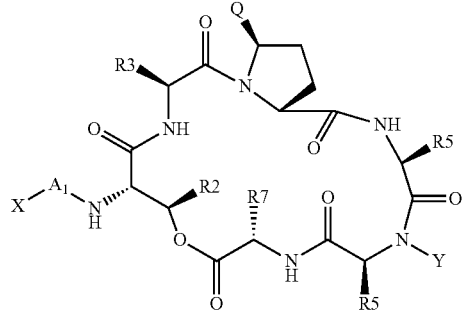

Q = H, OH wherein X and A$_1$ are as defined in claim 1, and wherein
R2 is methyl or hydrogen,
R3 is the side chain of leucine,
R5 is the side chain of the amino acid isoleucine or valine, in particular R5 stands for isoleucine,
R6 is the side chain of tyrosine which is optionally derivatized on its hydroxy group, wherein the hydroxyl group of the tyrosine is OR, and wherein R is selected from the group consisting of hydrogen, (C$_{1-12}$)alkyl, (C$_{2-12}$)alkenyl, (C$_{2-12}$)alkynyl, halo(C$_{1-12}$)alkyl, halo(C$_{2-12}$) alkenyl, halo(C$_{2-12}$)alkynyl, (C$_{1-12}$)alkoxycarbonyl, (C$_{1-12}$)alkoxy-carbonyl(C$_{1-12}$)alkyl, (C$_{1-12}$) alkylaminocarbonyl, unsubstituted or further substituted by aryl, arylalkyl, arylalkenyl or arylalkynyl, heterocyclyl and heterocyclylalkyl,
R7 is the side chain of the amino acid leucine, isoleucine or valine,
Y is either hydrogen or a methyl, or a pharmaceutically acceptable salt thereof.

8. The method of claim 1 wherein A1, A2, A3, A5, A6 and A7 are L-amino acids, or a pharmaceutically acceptable salt thereof.

9. The method of claim 1 wherein A4 is 3S,6R Ahp, or a pharmaceutically acceptable salt thereof.

10. The method of claim 1 wherein A1 is a glutamine, ornithine, or a glutamine derivative selected from glutamic nitrile, and glutamic acid ester, or a pharmaceutically acceptable salt thereof.

11. A process for producing the cyclic depsipeptide of Formula I:

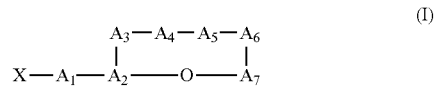

wherein the acyl residue X is CH$_3$CH$_2$CH(CH$_3$)CO or (CH$_3$)$_2$CHCO,
A$_1$ is glutamine, glutamic acid, or a derivative thereof selected from glutamic nitrile, glutamic acid C$_{1-12}$alkyl ester or glutamic acid C$_{6-24}$aryl ester,
A$_2$ is threonine,
A$_3$ is leucine,
A$_4$ is Ahp, 3-amino-piperidine-2-one, proline, 5-hydroxy-proline,
A$_5$ is isoleucine,
A$_6$ is tyrosine, N-Me-tyrosine or a derivative thereof selected from N-Me-tyrosine where the OH group of the tyrosine or N-Me-tyrosine is OR, wherein R is selected from the group consisting of $(C_{1-12})$alkyl, $(C_{2-12})$alkenyl, $(C_{2-12})$alkynyl, halo$(C_{1-12})$alkyl, halo$(C_{2-12})$alkenyl, halo$(C_{2-12})$alkynyl, $(C_{1-12})$alkoxycarbonyl, $(C_{1-12})$alkoxy-carbonyl$(C_{1-12})$alkyl, $(C_{1-12})$ alkylaminocarbonyl, wherein the alkyl, alkenyl and alkinyl moieties of groups R can be unsubstituted or further substituted by aryl, aryl$(C_{1-6})$alkyl, aryl$(C_{2-12})$alkenyl or aryl $(C_{2-12})$ alkynyl, heterocyclyl and heterocyclyl$(C_{1-12})$ alkyl, $A_7$ is isoleucine or valine;

or a pharmaceutically acceptable salt thereof;

comprising expressing the biosynthesis genes of a *Chondromyces crocatusa* (DSM 19329) in a heterologous microbial host strain for a time and under conditions effective to produce a first cyclic depsipeptide of Formula I, and optionally converting said first cyclic depsipeptide to a second cyclic depsipeptide of Formula I by means of one or more chemical reactions.

12. The method according to claim 1 wherein the cyclic depsipeptide is selected from the group consisting of Formula (II)

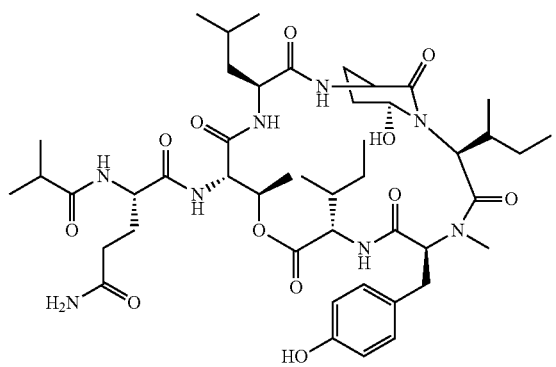

Formula (III)

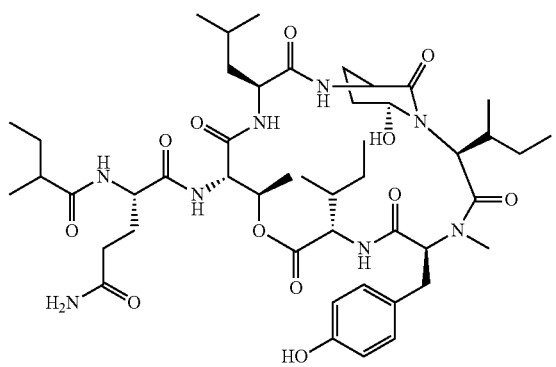

Formula (IV)

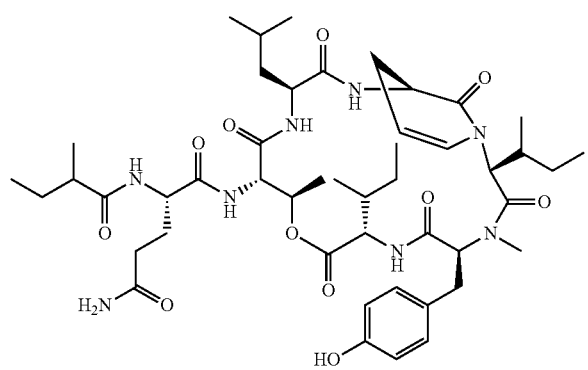

Formula (V)

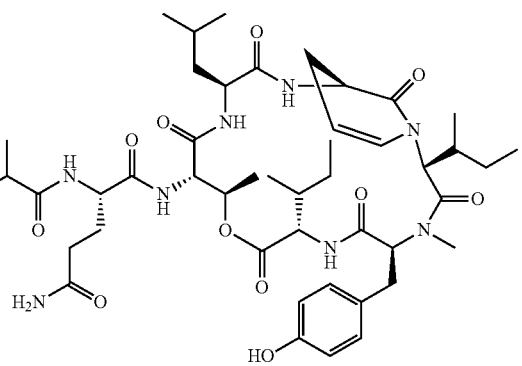

Formula (VI)

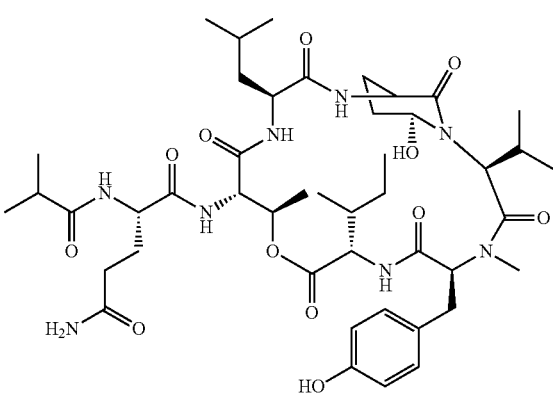

Formula (VII)

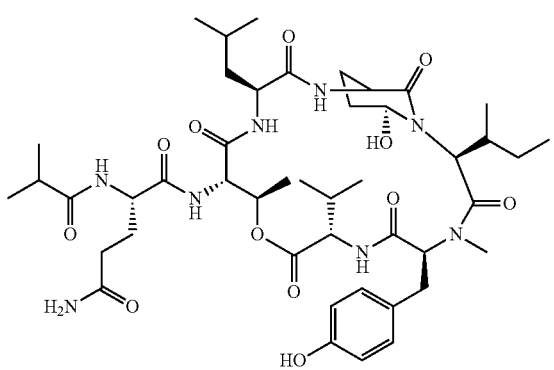

Formula (XI)

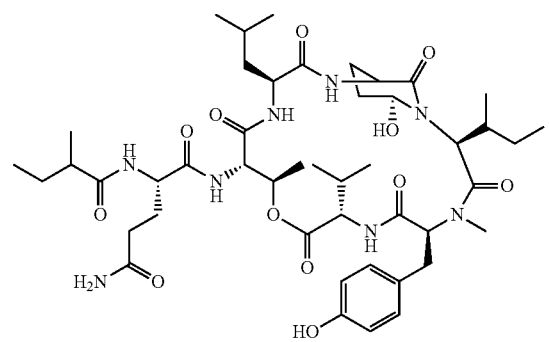

Formula (XII)
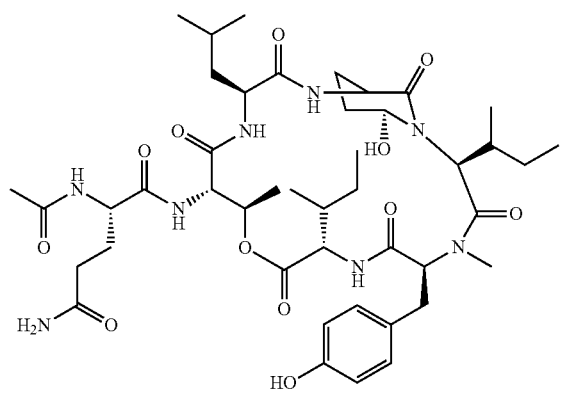
Formula (XIII)
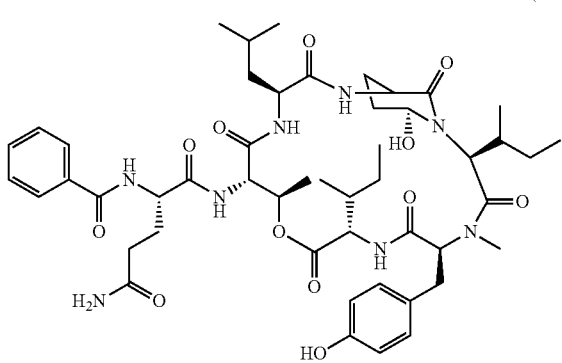
Formula (XIV)
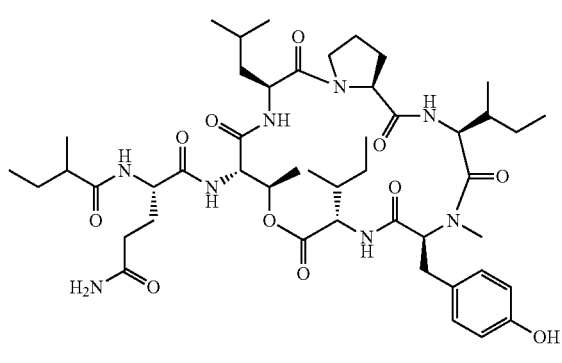
Formula (VIII)
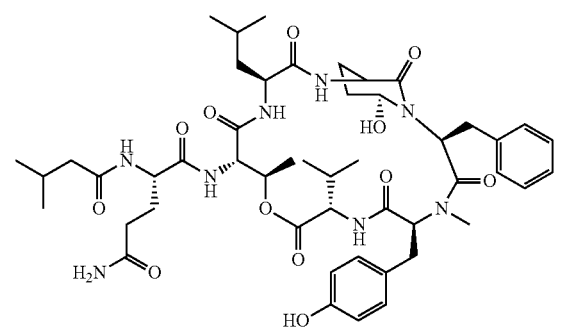
Formula (IX)
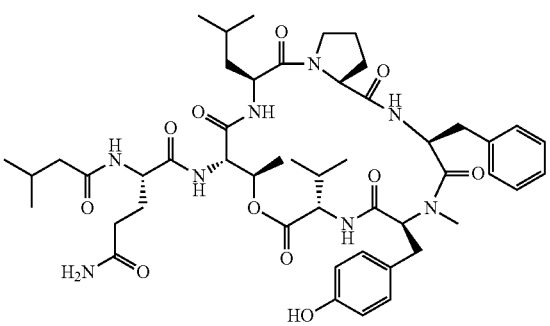
Formula (XVII)
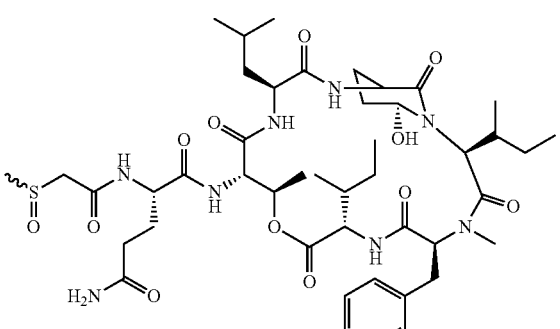
Formula (X)
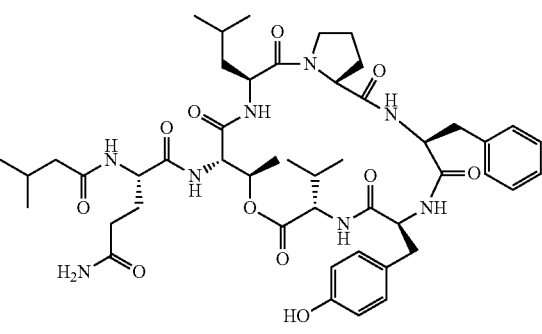

-continued

Formula (XV)

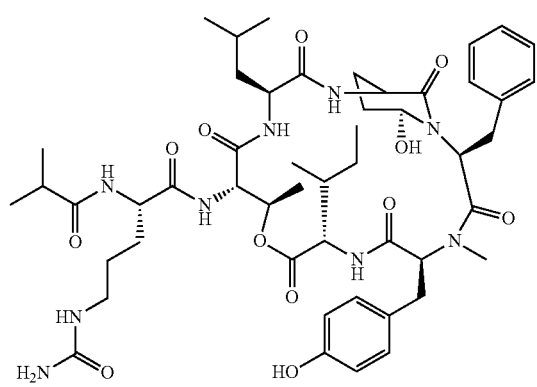

and

Formula (XVI)

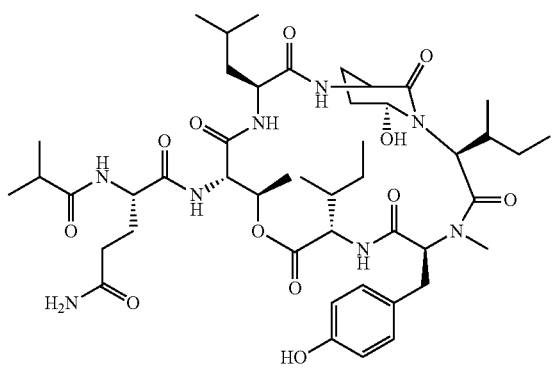

or a pharmaceutically acceptable salt thereof.

13. The method according to claim 1 wherein the cyclic depsipeptide is a compound of formula (II):

Formula (II)

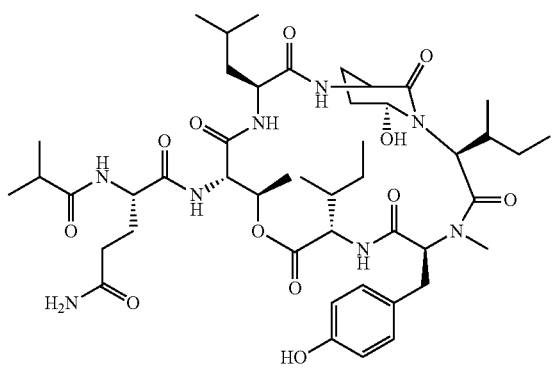

or a pharmaceutically acceptable salt thereof.

14. The method according to claim 12 wherein the cyclic depsipeptide is a compound of formula (III); or a pharmaceutically acceptable salt thereof.

15. The method according to claim 1 wherein the cyclic depsipeptide is a compound of formula (IV):

Formula (IV)

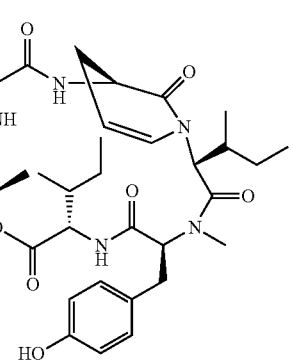

or a pharmaceutically acceptable salt thereof.

16. The method according to claim 1 wherein the cyclic depsipeptide is a compound of formula (V):

Formula (V)

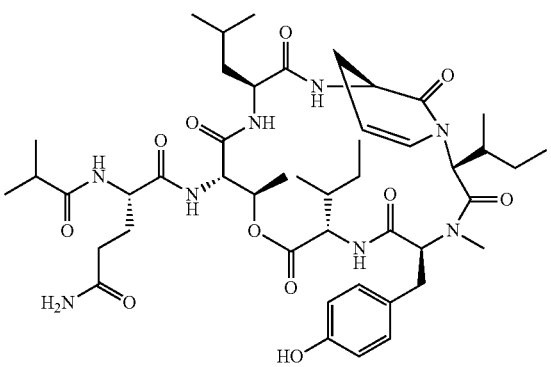

or a pharmaceutically acceptable salt thereof.

17. The method according to claim 1 wherein the cyclic depsipeptide is a compound of formula (XIV):

Formula (XIV)

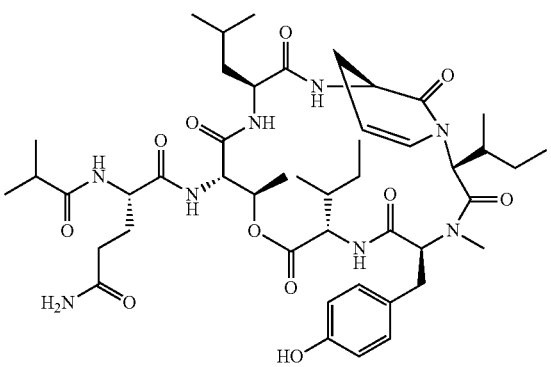

or a pharmaceutically acceptable salt thereof.

* * * * *